US008771969B2

(12) United States Patent
Van Eyk et al.

(10) Patent No.: US 8,771,969 B2
(45) **Date of Patent: *Jul. 8, 2014**

(54) PEPTIDE ANTIBODY DEPLETION AND ITS APPLICATION TO MASS SPECTROMETRY SAMPLE PREPARATION

(75) Inventors: Jennifer E. Van Eyk, Baltimore, MD (US); David Raymond Graham, Arbutus, MD (US); Rebekah Lynn Gunrdy, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/536,047

(22) Filed: Jun. 28, 2012

(65) Prior Publication Data

US 2012/0276570 A1 Nov. 1, 2012

Related U.S. Application Data

(63) Continuation of application No. 12/307,510, filed as application No. PCT/US2007/015390 on Jul. 3, 2007, now Pat. No. 8,232,066.

(60) Provisional application No. 60/818,363, filed on Jul. 3, 2006.

(51) Int. Cl.
*G01N 31/00* (2006.01)
*G01N 33/53* (2006.01)
*G01N 33/68* (2006.01)

(52) U.S. Cl.
CPC ........ *G01N 33/6842* (2013.01); *G01N 33/6848* (2013.01)
USPC ........... 435/7.21; 435/7.1; 436/501; 436/518; 424/130.1; 424/9.1; 530/300; 530/350

(58) Field of Classification Search
CPC ....................... G01N 33/6842; G01N 33/6848
See application file for complete search history.

(56) References Cited

U.S. PATENT DOCUMENTS

| | | | | |
|---|---|---|---|---|
| 8,232,066 | B2 * | 7/2012 | Van Eyk et al. | 435/7.21 |
| 2002/0055186 | A1 | 5/2002 | Barry et al. | |

FOREIGN PATENT DOCUMENTS

| | | |
|---|---|---|
| WO | WO2004/031730 | 4/2004 |
| WO | WO2005-049653 | 6/2005 |

OTHER PUBLICATIONS

Kuster B et al, "Scoring Proteomes with Proteotypic Peptide Probes" Nature Rev. Mol Cell Biol., vol. 6, No. 7, Jul. 2005, pp. 577-583.
Zhang F. et al., "Quantitation of Human Glutathione S-Transferases in Complex Matrices by Liquid Chromatography/Tandem Mass Spectrometry with Signature Peptides" RPAID Commun. Mass Spectrom., vol. 18, No. 4, Feb. 29, 2004, pp. 491-498.
Steel L. F. et al, "Efficient and Specific Removal of Albumin from Human Serum Samples" Mol. Cell Proteom., vol. 2, No. 4, 2003, pp. 262-270.
Doyen N. et al., "Study of the Antigenic Structure of Human Serum Albumin with Monoclonal Antibodies" Mol. Immunol., vol. 22, No. 1, Jan. 1985, pp. 1-10.

* cited by examiner

*Primary Examiner* — Lisa Cook
(74) *Attorney, Agent, or Firm* — Johns Hopkins Technology Transfer

(57) ABSTRACT

The present invention relates, e.g., to a method for pre-processing a sample for mass spectral analysis, comprising cleaving proteins in the sample to peptides and immunodepleting highly abundant and/or well-ionizing and/or proteotypic peptides from the sample. Also described are methods for identifying well-ionizing peptides for use in this and other methods; analytic (diagnostic) methods using antibodies against highly ionizable peptides from a protein target of interest; and compositions, kits and devices comprising antibodies of the invention.

15 Claims, 3 Drawing Sheets

SEQUENCE LISTING

```
<160> NUMBER OF SEQ ID NOS: 705

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Gly Glu His Asn Ile Asp Val Leu Glu Gly Asn Glu Gln Phe Ile
1               5                   10                  15

Asn Ala Ala Lys
            20


<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ile Thr His Pro Asn Phe Asn Gly Asn Thr Leu Asp Asn Asp Ile
1               5                   10                  15

Met Leu Ile Lys
            20


<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 3

Val Ala Thr Val Ser Leu Pro Arg
1 5

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Gly Gly Gly Gly Ser Phe Gly Tyr Ser Tyr Gly Gly Gly Ser Gly Gly
1 5 10 15

Gly Phe Ser Ala Ser Ser Leu Gly Gly Gly Phe Gly Gly Gly Ser Arg
20 25 30

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Asn Val Ser Thr Gly Asp Val Asn Val Glu Met Asn Ala Ala Pro Gly
1 5 10 15

Val Asp Leu Thr Gln Leu Leu Asn Asn Met Arg
20 25

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Gly Ser Leu Gly Gly Gly Phe Ser Ser Gly Gly Phe Ser Gly Gly Ser
1 5 10 15

Phe Ser Arg

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Leu Ala Leu Asp Leu Glu Ile Ala Thr Tyr Arg
1 5 10

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

```
Thr His Asn Leu Glu Pro Tyr Phe Glu Ser Phe Ile Asn Asn Leu Arg
1               5                   10                  15


<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Glu Glu Leu Gln Ile Thr Ala Gly Arg
1               5                   10


<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Ser Cys Arg Gln Phe Ser Ser Ser Tyr Leu Ser Arg Ser Gly Gly
1               5                   10                  15

Gly Gly Gly Gly Gly Leu Gly Ser Gly Gly Ser Ile Arg
            20                  25


<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Glu Leu Leu Gln Gln Val Asp Thr Ser Thr Arg
1               5                   10


<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ser Tyr Gly Ser Gly Gly Ser Ser Tyr Gly Ser Gly Gly Gly Ser
1               5                   10                  15

Tyr Gly Ser Gly Gly Gly Gly Gly Gly His Gly Ser Tyr Gly Ser Gly
            20                  25                  30

Ser Ser Ser Gly Gly Tyr Arg
        35


<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

-continued

```
Asn Gln Ile Leu Asn Leu Thr Thr Asp Asn Ala Asn Ile Leu Leu Gln
1               5                   10                  15

Ile Asp Asn Ala Arg
            20


<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Gly Gly Gly Gly Gly Gly Gly Cys Gly Gly Gly Gly Gly Val
1               5                   10                  15

Ser Ser Leu Arg
            20


<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Glu Met Glu Gln Asn Leu Arg
1               5


<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Met Gln Asp Met Val Glu Asp Tyr Arg
1               5                   10


<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Gln Tyr Glu Gln Leu Ala Glu Gln Asn Arg
1               5                   10


<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Glu Ile Ser Glu Leu Asn Arg
1               5
```

-continued

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

```
Gln Ile Ser Asn Leu Gln Gln Ser Ile Ser Asp Ala Glu Gln Arg
1               5                   10                  15
```

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

```
Ser Asp Leu Glu Met Gln Tyr Glu Thr Leu Gln Glu Glu Leu Met Ala
1               5                   10                  15

Leu Lys Lys
```

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

```
Leu Glu Asn Glu Ile Gln Thr Tyr Arg
1               5
```

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

```
Gly Gly Ser Gly Gly Ser Tyr Gly Gly Gly Gly Ser Gly Gly Gly Tyr
1               5                   10                  15

Gly Gly Gly Ser Gly Ser Arg
            20
```

<210> SEQ ID NO 23
<211> LENGTH: 31
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

```
Gly Gly Gly Gly Gly Gly Tyr Gly Ser Gly Gly Ser Ser Tyr Gly Ser
1               5                   10                  15

Gly Gly Gly Ser Tyr Gly Ser Gly Gly Gly Gly Gly Gly Gly Arg
            20                  25                  30
```

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Ser Gly Gly Gly Phe Ser Ser Gly Ser Ala Gly Ile Ile Asn Tyr Gln
1 5 10 15

Arg

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Asn Lys Pro Gly Val Tyr Thr Lys
1 5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Ser Leu Asn Asn Gln Phe Ala Ser Phe Ile Asp Lys
1 5 10

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Ala Glu Thr Glu Cys Gln Asn Thr Glu Tyr Gln Gln Leu Leu Asp Ile
1 5 10 15

Lys

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Val Thr Met Gln Asn Leu Asn Asp Arg
1 5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

His Gly Asn Ser His Gln Gly Glu Pro Arg
1 5 10

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

His Gly Val Gln Glu Leu Glu Ile Glu Leu Gln Ser Gln Leu Ser Lys
1 5 10 15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Asn Val Gln Ala Leu Glu Ile Glu Leu Gln Ser Gln Leu Ala Leu Lys
1 5 10 15

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Ser Leu Leu Glu Gly Glu Gly Ser Ser Gly Gly Gly Gly Arg
1 5 10

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Gln Glu Ile Glu Cys Gln Asn Gln Glu Tyr Ser Leu Leu Leu Ser Ile
1 5 10 15

Lys

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Phe Ser Ser Cys Gly Gly Gly Gly Gly Ser Phe Gly Ala Gly Gly Gly

-continued 1 5 10 15

Phe Gly Ser Arg
20

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Asn Tyr Ser Pro Tyr Tyr Asn Thr Ile Asp Asp Leu Lys
1 5 10

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Ser Glu Ile Asp Asn Val Lys
1 5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Ser Ile Ser Ile Ser Val Ala Arg
1 5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Thr Leu Leu Glu Gly Glu Glu Ser Arg
1 5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Gly Pro Ala Ala Ile Gln Lys
1 5

<210> SEQ ID NO 40
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 40

Leu Ala Ala Asp Asp Phe Arg
1 5

<210> SEQ ID NO 41
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Met Ser Gly Glu Cys Ala Pro Asn Val Ser Val Ser Val Ser Thr Ser
1 5 10 15

His Thr Thr Ile Ser Gly Gly Gly Ser Arg
20 25

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Met Thr Leu Asp Asp Phe Arg
1 5

<210> SEQ ID NO 43
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Ser His Cys Ile Ala Glu Val Glu Asn Asp Glu Met Pro Ala Asp Leu
1 5 10 15

Pro Ser Leu Ala Ala Asp Phe Val Glu Ser Lys
20 25

<210> SEQ ID NO 44
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Leu Val Arg Pro Glu Val Asp Val Met Cys Thr Ala Phe His Asp Asn
1 5 10 15

Glu Glu Thr Phe Leu Lys
20

<210> SEQ ID NO 45
<211> LENGTH: 21
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 45

Ala Leu Val Leu Ile Ala Phe Ala Gln Tyr Leu Gln Gln Cys Pro Phe
1 5 10 15

Glu Asp His Val Lys
20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Met Pro Cys Ala Glu Asp Tyr Leu Ser Val Val Leu Asn Gln Leu Cys
1 5 10 15

Val Leu His Glu Lys
20

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Glu Phe Asn Ala Glu Thr Phe Thr Phe His Ala Asp Ile Cys Thr Leu
1 5 10 15

Ser Glu Lys

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Val Phe Asp Glu Phe Lys Pro Leu Val Glu Glu Pro Gln Asn Leu Ile
1 5 10 15

Lys

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Val His Thr Glu Cys Cys His Gly Asp Leu Leu Glu Cys Ala Asp Asp
1 5 10 15

Arg

-continued

```
<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Pro Cys Phe Ser Ala Leu Glu Val Asp Glu Thr Tyr Val Pro Lys
1               5                   10                  15


<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Pro Tyr Phe Tyr Ala Pro Glu Leu Leu Phe Phe Ala Lys
1               5                   10


<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Val Phe Leu Gly Met Phe Leu Tyr Glu Tyr Ala Arg
1               5                   10


<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Asn Cys Glu Leu Phe Glu Gln Leu Gly Glu Tyr Lys
1               5                   10


<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Pro Gln Val Ser Thr Pro Thr Leu Val Glu Val Ser Arg
1               5                   10


<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55
```

Tyr Ile Cys Glu Asn Gln Asp Ser Ile Ser Ser Lys
1 5 10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Thr Cys Val Ala Asp Glu Ser Ala Glu Asn Cys Asp Lys
1 5 10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Cys Cys Ala Ala Ala Asp Pro His Glu Cys Tyr Ala Lys
1 5 10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Ala Val Met Asp Asp Phe Ala Ala Phe Val Glu Lys
1 5 10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Glu Thr Tyr Gly Glu Met Ala Asp Cys Cys Ala Lys
1 5 10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

His Pro Asp Tyr Ser Val Val Leu Leu Leu Arg
1 5 10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Ala Ala Phe Thr Glu Cys Cys Gln Ala Ala Asp Lys
1 5 10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Glu Cys Cys Glu Lys Pro Leu Leu Glu Lys
1 5 10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Leu Val Asn Glu Val Thr Glu Phe Ala Lys
1 5 10

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Cys Cys Thr Glu Ser Leu Val Asn Arg
1 5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Asn Glu Cys Phe Leu Gln His Lys
1 5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Ser Leu His Thr Leu Phe Gly Asp Lys
1 5

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Leu Val Ala Ala Ser Gln Ala Ala Leu Gly Leu
1 5 10

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Glu Thr Cys Phe Ala Glu Glu Gly Lys
1 5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Gln Thr Ala Leu Val Glu Leu Val Lys
1 5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Thr Tyr Glu Thr Thr Leu Glu Lys
1 5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Phe Gln Asn Ala Leu Leu Val Arg
1 5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Asp Leu Gly Glu Glu Asn Phe Lys
1 5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Asp Asp Asn Pro Asn Leu Pro Arg
1 5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Tyr Leu Tyr Glu Ile Ala Arg
1 5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Ala Glu Phe Ala Glu Val Ser Lys
1 5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Leu Cys Thr Val Ala Thr Leu Arg
1 5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Leu Val Thr Asp Leu Thr Lys
1 5

<210> SEQ ID NO 78
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 78

Ala Ala Cys Leu Leu Pro Lys
1 5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Ser Glu Val Ala His Arg
1 5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Asn Tyr Ala Glu Ala Lys
1 5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Thr Pro Val Ser Asp Arg
1 5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Ala Trp Ala Val Ala Arg
1 5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Gln Glu Pro Glu Arg
1 5

-continued

<210> SEQ ID NO 84
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Ile Pro Leu Cys Ala Asn Leu Val Pro Val Pro Ile Thr Asn Ala
1               5                   10                  15

Thr Leu Asp Gln Ile Thr Gly Lys
            20

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Val Gln Glu Ile Gln Ala Thr Phe Phe Tyr Phe Thr Pro Asn Lys
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Asp Gln Cys Ile Tyr Asn Thr Thr Tyr Leu Asn Val Gln Arg
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Val Gly Gly Gln Glu His Phe Ala His Leu Leu Ile Leu Arg
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asn Trp Gly Leu Ser Val Tyr Ala Asp Lys Pro Glu Thr Thr Lys
1               5                   10                  15

<210> SEQ ID NO 89
<211> LENGTH: 14
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 89

Glu Gln Leu Gly Glu Phe Tyr Glu Ala Leu Asp Cys Leu Arg
1               5                   10


<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Thr Tyr Met Leu Ala Phe Asp Val Asn Asp Glu Lys
1               5                   10


<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Phe Tyr Ile Ala Ser Ala Phe Arg
1               5


<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Asp Val Val Tyr Thr Asp Trp Lys
1               5


<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Glu Asp Thr Ile Phe Leu Arg
1               5


<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asn Glu Glu Tyr Asn Lys
1               5
```

```
<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu Asn Gly Thr Ile Ser Arg
1               5


<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Glu Pro Leu Glu Lys
1               5


<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Glu Tyr Gln Thr Arg
1               5


<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Glu Glu Gly Glu Ser
1               5


<210> SEQ ID NO 99
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Asp Thr His Asp Glu Ile Leu Glu Gly Leu Asn Phe Asn Leu Thr
1               5                   10                  15

Glu Ile Pro Glu Ala Gln Ile His Glu Gly Phe Gln Glu Leu Leu Arg
            20                  25                  30


<210> SEQ ID NO 100
<211> LENGTH: 30
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 100

Gln Leu Ala His Gln Ser Asn Ser Thr Asn Ile Phe Phe Ser Pro Val
1               5                   10                  15

Ser Ile Ala Thr Ala Phe Ala Met Leu Ser Leu Gly Thr Lys
            20                  25                  30


<210> SEQ ID NO 101
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Leu Asn Gln Pro Asp Ser Gln Leu Gln Leu Thr Thr Gly Asn Gly
1               5                   10                  15

Leu Phe Leu Ser Glu Gly Leu Lys
            20


<210> SEQ ID NO 102
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Thr Glu Ala Ala Gly Ala Met Phe Leu Glu Ala Ile Pro Met Ser
1               5                   10                  15

Ile Pro Pro Glu Val Lys
            20


<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Tyr His Ser Glu Ala Phe Thr Val Asn Phe Gly Asp Thr Glu Glu
1               5                   10                  15

Ala Lys


<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Thr Glu Glu Glu Asp Phe His Val Asp Gln Val Thr Thr Val Lys
1               5                   10                  15


<210> SEQ ID NO 105
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 105

Phe Asn Lys Pro Phe Val Phe Leu Met Ile Glu Gln Asn Thr Lys
1               5                   10                  15


<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Val Phe Ser Asn Gly Ala Asp Leu Ser Gly Val Thr Glu Glu Ala Pro
1               5                   10                  15

Leu Lys


<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Gln His Leu Glu Asn Glu Leu Thr His Asp Ile Ile Thr Lys
1               5                   10                  15


<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Thr Asp Thr Ser His His Asp Gln Asp His Pro Thr Phe Asn Lys
1               5                   10                  15


<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Tyr Leu Gly Asn Ala Thr Ala Ile Phe Phe Leu Pro Asp Glu Gly Lys
1               5                   10                  15


<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110
```

-continued

Ile Thr Pro Asn Leu Ala Glu Phe Ala Phe Ser Leu Tyr Arg
1 5 10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Asp Thr Val Phe Ala Leu Val Asn Tyr Ile Phe Phe Lys
1 5 10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Leu Gly Met Phe Asn Ile Gln His Cys Lys
1 5 10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Leu Ser Ile Thr Gly Thr Tyr Asp Leu Lys
1 5 10

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Trp Glu Arg Pro Phe Glu Val Lys
1 5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Leu Ser Ser Trp Val Leu Leu Met Lys
1 5

<210> SEQ ID NO 116
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 116

Glu Asp Pro Gln Gly Asp Ala Ala Gln Lys
1               5                   10


<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Val Leu Gly Gln Leu Gly Ile Thr Lys
1               5                   10


<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Ile Asn Asp Tyr Val Glu Lys
1               5


<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Phe Leu Glu Asn Glu Asp Arg
1               5


<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Val Leu Thr Ile Asp Glu Lys
1               5


<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Ala Ser Leu His Leu Pro Lys
1               5
```

-continued

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

```
Val Val Asn Pro Thr Gln Lys
1               5
```

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Ser Pro Leu Phe Met Gly Lys
1               5
```

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Phe Leu Glu Asp Val Lys
1               5
```

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
Ile Val Asp Leu Val Lys
1               5
```

<210> SEQ ID NO 126
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
Ser Phe Val His Leu Glu Pro Met Ser His Glu Leu Pro Cys Gly His
1               5                   10                  15

Thr Gln Thr Val Gln Ala His Tyr Ile Leu Asn Gly Gly Thr Leu Leu
            20                  25                  30

Gly Leu Lys
        35
```

<210> SEQ ID NO 127
<211> LENGTH: 35
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 127

```
Gly Asn Glu Ala Asn Tyr Tyr Ser Asn Ala Thr Thr Asp Glu His Gly
1               5                   10                  15

Leu Val Gln Phe Ser Ile Asn Thr Thr Asn Val Met Gly Thr Ser Leu
            20                  25                  30

Thr Val Arg
        35
```

<210> SEQ ID NO 128
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

```
Tyr Phe Pro Glu Thr Trp Ile Trp Asp Leu Val Val Val Asn Ser Ala
1               5                   10                  15

Gly Val Ala Glu Val Gly Val Thr Val Pro Asp Thr Ile Thr Glu Trp
            20                  25                  30

Lys
```

<210> SEQ ID NO 129
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Ile Ile Thr Ile Leu Glu Glu Glu Met Asn Val Ser Val Cys Gly Leu
1               5                   10                  15

Tyr Thr Tyr Gly Lys Pro Val Pro Gly His Val Thr Val Ser Ile Cys
            20                  25                  30

Arg
```

<210> SEQ ID NO 130
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

```
Ser Leu Gly Asn Val Asn Phe Thr Val Ser Ala Glu Ala Leu Glu Ser
1               5                   10                  15

Gln Glu Leu Cys Gly Thr Glu Val Pro Ser Val Pro Glu His Gly Arg
            20                  25                  30
```

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Pro Cys Tyr Gly Tyr Gln Trp Val Ser Glu Glu His Glu Glu Ala
1 5 10 15

His His Thr Ala Tyr Leu Val Phe Ser Pro Ser Lys
20 25

<210> SEQ ID NO 132
<211> LENGTH: 30
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Gly Gly Val Glu Asp Glu Val Thr Leu Ser Ala Tyr Ile Thr Ile Ala
1 5 10 15

Leu Leu Glu Ile Pro Leu Thr Val Thr His Pro Val Val Arg
20 25 30

<210> SEQ ID NO 133
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Ala Val Asp Gln Ser Val Leu Leu Met Lys Pro Asp Ala Glu Leu Ser
1 5 10 15

Ala Ser Ser Val Tyr Asn Leu Leu Pro Glu Lys
20 25

<210> SEQ ID NO 134
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Val Val Ser Met Asp Glu Asn Phe His Pro Leu Asn Glu Leu Ile Pro
1 5 10 15

Leu Val Tyr Ile Gln Asp Pro Lys
20

<210> SEQ ID NO 135
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

Ser Val Ser Gly Lys Pro Gln Tyr Met Val Leu Val Pro Ser Leu Leu
1 5 10 15

His Thr Glu Thr Thr Glu Lys
20

<210> SEQ ID NO 136

<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Val Tyr Asp Tyr Tyr Glu Thr Asp Glu Phe Ala Ile Ala Glu Tyr Asn
1 5 10 15

Ala Pro Cys Ser Lys
20

<210> SEQ ID NO 137
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Ser Leu Phe Thr Asp Leu Glu Ala Glu Asn Asp Val Leu His Cys Val
1 5 10 15

Ala Phe Ala Val Pro Lys
20

<210> SEQ ID NO 138
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Ala Tyr Ile Phe Ile Asp Glu Ala His Ile Thr Gln Ala Leu Ile Trp
1 5 10 15

Leu Ser Gln Arg
20

<210> SEQ ID NO 139
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Gln Gln Asn Ala Gln Gly Gly Phe Ser Ser Thr Gln Asp Thr Val Val
1 5 10 15

Ala Leu His Ala Leu Ser Lys
20

<210> SEQ ID NO 140
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Gly Cys Val Leu Leu Ser Tyr Leu Asn Glu Thr Val Thr Val Ser Ala
1 5 10 15

Ser Leu Glu Ser Val Arg
            20

<210> SEQ ID NO 141
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Glu Thr Thr Phe Asn Ser Leu Leu Cys Pro Ser Gly Gly Glu Val Ser
1               5                   10                  15

Glu Glu Leu Ser Leu Lys
            20

<210> SEQ ID NO 142
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Glu Glu Phe Pro Phe Ala Leu Gly Val Gln Thr Leu Pro Gln Thr Cys
1               5                   10                  15

Asp Glu Pro Lys
            20

<210> SEQ ID NO 143
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Leu Thr Gly Phe Pro Gly Pro Leu Asn Asp Gln Asp Asp Glu Asp
1               5                   10                  15

Cys Ile Asn Arg
            20

<210> SEQ ID NO 144
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Val Ser Asn Gln Thr Leu Ser Leu Phe Phe Thr Val Leu Gln Asp Val
1               5                   10                  15

Pro Val Arg

<210> SEQ ID NO 145
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

His Asn Val Tyr Ile Asn Gly Ile Thr Tyr Thr Pro Val Ser Ser Thr
1 5 10 15

Asn Glu Lys

<210> SEQ ID NO 146
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Leu His Thr Glu Ala Gln Ile Gln Glu Glu Gly Thr Val Val Glu Leu
1 5 10 15

Thr Gly Arg

<210> SEQ ID NO 147
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Val Asp Leu Ser Phe Ser Pro Ser Gln Ser Leu Pro Ala Ser His Ala
1 5 10 15

His Leu Arg

<210> SEQ ID NO 148
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Leu Leu Leu Gln Gln Val Ser Leu Pro Glu Leu Pro Gly Glu Tyr Ser
1 5 10 15

Met Lys

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Ala Phe Gln Pro Phe Phe Val Glu Leu Thr Met Pro Tyr Ser Val Ile
1 5 10 15

Arg

<210> SEQ ID NO 150
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Ala Gly Ala Phe Cys Leu Ser Glu Asp Ala Gly Leu Gly Ile Ser Ser
1 5 10 15

Thr Ala Ser Leu Arg
20

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Met Cys Pro Gln Leu Gln Gln Tyr Glu Met His Gly Pro Glu Gly Leu
1 5 10 15

Arg

<210> SEQ ID NO 152
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Tyr Ser Asp Ala Ser Asp Cys His Gly Glu Asp Ser Gln Ala Phe Cys
1 5 10 15

Glu Lys

<210> SEQ ID NO 153
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Val Ser Val Gln Leu Glu Ala Ser Pro Ala Phe Leu Ala Val Pro Val
1 5 10 15

Glu Lys

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Gln Phe Ser Phe Pro Leu Ser Ser Glu Pro Phe Gln Gly Ser Tyr Lys
1 5 10 15

<210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Leu Leu Ile Tyr Ala Val Leu Pro Thr Gly Asp Val Ile Gly Asp Ser
1 5 10 15

Ala Lys

<210> SEQ ID NO 156
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Phe Ser Gly Gln Leu Asn Ser His Gly Cys Phe Tyr Gln Gln Val Lys
1 5 10 15

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 157

Ala His Thr Ser Phe Gln Ile Ser Leu Ser Val Ser Tyr Thr Gly Ser
1 5 10 15

Arg

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Asp Thr Val Ile Lys Pro Leu Leu Val Glu Pro Glu Gly Leu Glu Lys
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Ser Ser Ser Asn Glu Glu Val Met Phe Leu Thr Val Gln Val Lys
1 5 10 15

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

Thr Glu His Pro Phe Thr Val Glu Glu Phe Val Leu Pro Lys 1 5 10

<210> SEQ ID NO 161
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Asp Asn Ser Val His Trp Glu Arg Pro Gln Lys Pro Lys
1 5 10

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Thr Glu Val Ser Ser Asn His Val Leu Ile Tyr Leu Asp Lys
1 5 10

<210> SEQ ID NO 163
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Ile Ala Gln Trp Gln Ser Phe Gln Leu Glu Gly Gly Leu Lys
1 5 10

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Ala Leu Leu Ala Tyr Ala Phe Ala Leu Ala Gly Asn Gln Asp Lys
1 5 10 15

<210> SEQ ID NO 165
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Leu Val His Val Glu Glu Pro His Thr Glu Thr Val Arg
1 5 10

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Thr Ala Gln Glu Gly Asp His Gly Ser His Val Tyr Thr Lys
1 5 10

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Ala Ala Gln Val Thr Ile Gln Ser Ser Gly Thr Phe Ser Ser Lys
1 5 10 15

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Val Thr Gly Glu Gly Cys Val Tyr Leu Gln Thr Ser Leu Lys
1 5 10

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Asn Gln Gly Asn Thr Trp Leu Thr Ala Phe Val Leu Lys
1 5 10

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Asp Met Tyr Ser Phe Leu Glu Asp Met Gly Leu Lys
1 5 10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

His Tyr Asp Gly Ser Tyr Ser Thr Phe Gly Glu Arg
1 5 10

<210> SEQ ID NO 172

<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 172

Met Val Ser Gly Phe Ile Pro Leu Lys Pro Thr Val Lys
1 5 10

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Asn Glu Asp Ser Leu Val Phe Val Gln Thr Asp Lys
1 5 10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 174

Glu Gln Ala Pro His Cys Ile Cys Ala Asn Gly Arg
1 5 10

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 175

Asn Ala Leu Phe Cys Leu Glu Ser Ala Trp Lys
1 5 10

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 176

Val Gly Phe Tyr Glu Ser Asp Val Met Gly Arg
1 5 10

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 177

-continued

Ala Ile Gly Tyr Leu Asn Thr Gly Tyr Gln Arg
1 5 10

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Leu Ser Phe Tyr Tyr Leu Ile Met Ala Lys
1 5 10

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Val Thr Ala Ala Pro Gln Ser Val Cys Ala Leu Arg
1 5 10

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Leu Pro Pro Asn Val Val Glu Glu Ser Ala Arg
1 5 10

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 181

Tyr Asp Val Glu Asn Cys Leu Ala Asn Lys
1 5 10

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 182

Gln Gly Ile Pro Phe Phe Gly Gln Val Arg
1 5 10

<210> SEQ ID NO 183
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 183

Ser Ala Ser Asn Met Ala Ile Val Asp Val Lys
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Ile Tyr Lys Pro Gly Gln Thr Val Lys
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gln Thr Val Ser Trp Ala Val Thr Pro Lys
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Ser Gly Ser Leu Leu Asn Asn Ala Ile Lys
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gly His Phe Ser Ile Ser Ile Pro Val Lys
1               5                   10

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Phe Glu Val Gln Val Thr Val Pro Lys
1               5

-continued

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 189

Ala Thr Val Leu Asn Tyr Leu Pro Lys
1               5

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 190

Phe Gln Val Asp Asn Asn Asn Arg
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 191

Thr Gly Thr His Gly Leu Leu Val Lys
1               5

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Ser Leu Asn Glu Glu Ala Val Lys
1               5

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 193

Tyr Gly Ala Ala Thr Phe Thr Arg
1               5

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 194

Asp Leu Lys Pro Ala Ile Val Lys
1 5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

Tyr Asn Ile Leu Pro Glu Lys
1 5

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Ser Asp Ile Ala Pro Val Ala Arg
1 5

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Gln Ser Ser Glu Ile Thr Arg
1 5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Gly Pro Thr Gln Glu Phe Lys
1 5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Gly Glu Ala Phe Thr Leu Lys
1 5

<210> SEQ ID NO 200
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 200

Val Asp Ser His Phe Arg
1 5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 201

Gly Val Pro Ile Pro Asn Lys
1 5

<210> SEQ ID NO 202
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 202

Asp Asn Gly Cys Phe Arg
1 5

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 203

Ser Asn His Val Ser Arg
1 5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 204

Glu Tyr Glu Met Lys
1 5

<210> SEQ ID NO 205
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 205

Thr Phe Ala Gln Ala Arg
1 5

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 206

Thr Thr Val Met Val Lys
1 5

<210> SEQ ID NO 207
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 207

Ala Phe Thr Asn Ser Lys
1 5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 208

Gln Leu Asn Tyr Lys
1 5

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 209

Gln Glu Asp Met Lys
1 5

<210> SEQ ID NO 210
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 210

Glu Gln Leu Gly Pro Val Thr Gln Glu Phe Trp Asp Asn Leu Glu Lys
1 5 10 15

<210> SEQ ID NO 211
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 211

Leu Leu Asp Asn Trp Asp Ser Val Thr Ser Thr Phe Ser Lys
1 5 10

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 212

Asp Tyr Val Ser Gln Phe Glu Gly Ser Ala Leu Gly Lys
1 5 10

<210> SEQ ID NO 213
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Val Ser Phe Leu Ser Ala Leu Glu Glu Tyr Thr Lys
1 5 10

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Thr His Leu Ala Pro Tyr Ser Asp Glu Leu Arg
1 5 10

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Trp Gln Glu Glu Met Glu Leu Tyr Arg
1 5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Val Gln Pro Tyr Leu Asp Asp Phe Gln Lys
1 5 10

<210> SEQ ID NO 217
<211> LENGTH: 11
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 217

Asp Leu Ala Thr Val Tyr Val Asp Val Leu Lys
1 5 10

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Gln Gly Leu Leu Pro Val Leu Glu Ser Phe Lys
1 5 10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 219

Asp Glu Pro Pro Gln Ser Pro Trp Asp Arg
1 5 10

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 220

Ala Thr Glu His Leu Ser Thr Leu Ser Glu Lys
1 5 10

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Leu Ser Pro Leu Gly Glu Glu Met Arg
1 5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Ala Lys Pro Ala Leu Glu Asp Leu Arg
1 5

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Leu His Glu Leu Gln Glu Lys
1               5

<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Glu Leu Gln Glu Gly Ala Arg
1               5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Leu Ala Glu Tyr His Ala Lys
1               5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ala His Val Asp Ala Leu Arg
1               5

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asp Leu Glu Glu Val Lys
1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Glu Thr Glu Gly Leu Arg
1 5

<210> SEQ ID NO 229
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Ala Gly Thr Glu Leu Val Asn Phe Leu Ser Tyr Phe Val Glu Leu Gly
1 5 10 15

Thr Gln Pro Ala Thr Gln
20

<210> SEQ ID NO 230
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 230

Glu Pro Cys Val Glu Ser Leu Val Ser Gln Tyr Phe Gln Thr Val Thr
1 5 10 15

Asp Tyr Gly Lys
20

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 231

Ser Pro Glu Leu Gln Ala Glu Ala Lys
1 5

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 232

Glu Gln Leu Thr Pro Leu Ile Lys
1 5

<210> SEQ ID NO 233
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

```
Ser Tyr Phe Glu Lys
1               5


<210> SEQ ID NO 234
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

His Leu Ile Val Thr Pro Ser Gly Cys Gly Glu Gln Asn Met Ile Gly
1               5                   10                  15

Met Thr Pro Thr Val Ile Ala Val His Tyr Leu Asp Glu Thr Glu Gln
            20                  25                  30

Trp Glu Lys
        35


<210> SEQ ID NO 235
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gln Asp Ser Leu Ser Ser Gln Asn Gln Leu Gly Val Leu Pro Leu Ser
1               5                   10                  15

Trp Asp Ile Pro Glu Leu Val Asn Met Gly Gln Trp Lys
            20                  25


<210> SEQ ID NO 236
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Leu Glu Ser Glu Glu Thr Met Val Leu Glu Ala His Asp Ala Gln Gly
1               5                   10                  15

Asp Val Pro Val Thr Val Thr Val His Asp Phe Pro Gly Lys
            20                  25                  30


<210> SEQ ID NO 237
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

His Tyr Leu Met Trp Gly Leu Ser Ser Asp Phe Trp Gly Glu Lys Pro
1               5                   10                  15

Asn Leu Ser Tyr Ile Ile Gly Lys
            20


<210> SEQ ID NO 238
<211> LENGTH: 26
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 238

Gly Asp Gln Asp Ala Thr Met Ser Ile Leu Asp Ile Ser Met Met Thr
1 5 10 15

Gly Phe Ala Pro Asp Thr Asp Asp Leu Lys
20 25

<210> SEQ ID NO 239
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 239

Tyr Phe Lys Pro Gly Met Pro Phe Asp Leu Met Val Phe Val Thr Asn
1 5 10 15

Pro Asp Gly Ser Pro Ala Tyr Arg
20

<210> SEQ ID NO 240
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

Tyr Tyr Gly Gly Gly Tyr Gly Ser Thr Gln Ala Thr Phe Met Val Phe
1 5 10 15

Gln Ala Leu Ala Gln Tyr Gln Lys
20

<210> SEQ ID NO 241
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 241

Thr Met Gln Ala Leu Pro Tyr Ser Thr Val Gly Asn Ser Asn Asn Tyr
1 5 10 15

Leu His Leu Ser Val Leu Arg
20

<210> SEQ ID NO 242
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Gln Lys Pro Asp Gly Val Phe Gln Glu Asp Ala Pro Val Ile His Gln
1 5 10 15

Glu Met Ile Gly Gly Leu Arg
20

<210> SEQ ID NO 243
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

```
Asp Thr Trp Val Glu His Trp Pro Glu Glu Asp Glu Cys Gln Asp Glu
1               5                   10                  15

Glu Asn Gln Lys
            20
```

<210> SEQ ID NO 244
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Asp Tyr Ala Gly Val Phe Ser Asp Ala Gly Leu Thr Phe Thr Ser Ser
1               5                   10                  15

Ser Gly Gln Gln Thr Ala Gln Arg
            20
```

<210> SEQ ID NO 245
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

```
Glu Pro Gly Gln Asp Leu Val Val Leu Pro Leu Ser Ile Thr Thr Asp
1               5                   10                  15

Phe Ile Pro Ser Phe Arg
            20
```

<210> SEQ ID NO 246
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

```
Gly Ile Cys Val Ala Asp Pro Phe Glu Val Thr Val Met Gln Asp Phe
1               5                   10                  15

Phe Ile Asp Leu Arg
            20
```

<210> SEQ ID NO 247
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

```
Ser Leu Tyr Val Ser Ala Thr Val Ile Leu His Ser Gly Ser Asp Met
1               5                   10                  15

Val Gln Ala Glu Arg
            20


<210> SEQ ID NO 248
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Val Gln Leu Ser Asn Asp Phe Asp Glu Tyr Ile Met Ala Ile Glu Gln
1               5                   10                  15

Thr Ile Lys


<210> SEQ ID NO 249
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Thr Val Leu Thr Pro Ala Thr Asn His Met Gly Asn Val Thr Phe Thr
1               5                   10                  15

Ile Pro Ala Asn Arg
            20


<210> SEQ ID NO 250
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Glu Asp Ile Pro Pro Ala Asp Leu Ser Asp Gln Val Pro Asp Thr Glu
1               5                   10                  15

Ser Glu Thr Arg
            20


<210> SEQ ID NO 251
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Val Pro Val Ala Val Gln Gly Glu Asp Thr Val Gln Ser Leu Thr Gln
1               5                   10                  15

Gly Asp Gly Val Ala Lys
            20


<210> SEQ ID NO 252
<211> LENGTH: 18
<212> TYPE: PRT
<213> ORGANISM: Artificial Sequence
```

<220> FEATURE:
<223> OTHER INFORMATION: Description of Artificial Sequence: Synthetic peptide

<400> SEQUENCE: 252

Ala Tyr Tyr Glu Asn Ser Pro Gln Gln Val Phe Ser Thr Glu Phe Glu
1 5 10 15

Val Lys

<210> SEQ ID NO 253
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 253

Val Phe Ser Leu Ala Val Asn Leu Ile Ala Ile Asp Ser Gln Val Leu
1 5 10 15

Cys Gly Ala Val Lys
20

<210> SEQ ID NO 254
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 254

Ile Leu Leu Gln Gly Thr Pro Val Ala Gln Met Thr Glu Asp Ala Val
1 5 10 15

Asp Ala Glu Arg
20

<210> SEQ ID NO 255
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Gln Leu Tyr Asn Val Glu Ala Thr Ser Tyr Ala Leu Leu Ala Leu Leu
1 5 10 15

Gln Leu Lys

<210> SEQ ID NO 256
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 256

Asp Ala Pro Asp His Gln Glu Leu Asn Leu Asp Val Ser Leu Gln Leu
1 5 10 15

Pro Ser Arg

<210> SEQ ID NO 257

<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Gln Cys Gln Asp Leu Gly Ala Phe Thr Glu Ser Met Val Val Phe Gly
1 5 10 15

Cys Pro Asn

<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 258

Val Val Leu Val Ser Leu Gln Ser Gly Tyr Leu Phe Ile Gln Thr Asp
1 5 10 15

Lys

<210> SEQ ID NO 259
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Leu Ser Ile Asn Thr His Pro Ser Gln Lys Pro Leu Ser Ile Thr Val
1 5 10 15

Arg

<210> SEQ ID NO 260
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 260

Glu Tyr Val Leu Pro Ser Phe Glu Val Ile Val Glu Pro Thr Glu Lys
1 5 10 15

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

Ser Glu Phe Pro Glu Ser Trp Leu Trp Asn Val Glu Asp Leu Lys
1 5 10 15

<210> SEQ ID NO 262
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 262

Thr Glu Leu Arg Pro Gly Glu Thr Leu Asn Val Asn Phe Leu Leu Arg
1 5 10 15

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 263

Val Glu Gly Thr Ala Phe Val Ile Phe Gly Ile Gln Asp Gly Glu Gln
1 5 10 15

Arg

<210> SEQ ID NO 264
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 264

Val His Gln Tyr Phe Asn Val Glu Leu Ile Gln Pro Gly Ala Val Lys
1 5 10 15

<210> SEQ ID NO 265
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 265

Ser Asn Leu Asp Glu Asp Ile Ile Ala Glu Glu Asn Ile Val Ser Arg
1 5 10 15

<210> SEQ ID NO 266
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Asp Ser Ile Thr Thr Trp Glu Ile Leu Ala Val Ser Met Ser Asp Lys
1 5 10 15

<210> SEQ ID NO 267
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Ser Gly Ile Pro Ile Val Thr Ser Pro Tyr Gln Ile His Phe Thr Lys 1 5 10 15

<210> SEQ ID NO 268
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Asp Met Ala Leu Thr Ala Phe Val Leu Ile Ser Leu Gln Glu Ala Lys
1 5 10 15

<210> SEQ ID NO 269
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Val Glu Leu Leu His Asn Pro Ala Phe Cys Ser Leu Ala Thr Thr Lys
1 5 10 15

<210> SEQ ID NO 270
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

Asp Ile Cys Glu Glu Gln Val Asn Ser Leu Pro Gly Ser Ile Thr Lys
1 5 10 15

<210> SEQ ID NO 271
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 271

Ser Tyr Thr Val Ala Ile Ala Gly Tyr Ala Leu Ala Gln Met Gly Arg
1 5 10 15

<210> SEQ ID NO 272
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

Phe Val Thr Val Gln Ala Thr Phe Gly Thr Gln Val Val Glu Lys
1 5 10 15

<210> SEQ ID NO 273
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 273

Ala Gly Asp Phe Leu Glu Ala Asn Tyr Met Asn Leu Gln Arg
1 5 10

<210> SEQ ID NO 274
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Thr Val Met Val Asn Ile Glu Asn Pro Glu Gly Ile Pro Val Lys
1 5 10 15

<210> SEQ ID NO 275
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Val Tyr Ala Tyr Tyr Asn Leu Glu Glu Ser Cys Thr Arg
1 5 10

<210> SEQ ID NO 276
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Val Phe Leu Asp Cys Cys Asn Tyr Ile Thr Glu Leu Arg
1 5 10

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Leu Val Ala Tyr Tyr Thr Leu Ile Gly Ala Ser Gly Gln Arg
1 5 10

<210> SEQ ID NO 278
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Ser Pro Met Tyr Ser Ile Ile Thr Pro Asn Ile Leu Arg
1 5 10

<210> SEQ ID NO 279

<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

Gly Gln Gly Thr Leu Ser Val Val Thr Met Tyr His Ala Lys
1 5 10

<210> SEQ ID NO 280
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Ala Ala Val Tyr His His Phe Ile Ser Asp Gly Val Arg
1 5 10

<210> SEQ ID NO 281
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 281

Ile Pro Ile Glu Asp Gly Ser Gly Glu Val Val Leu Ser Arg
1 5 10

<210> SEQ ID NO 282
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 282

Ser Ser Leu Ser Val Pro Tyr Val Ile Val Pro Leu Lys
1 5 10

<210> SEQ ID NO 283
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 283

Thr Ile Tyr Thr Pro Gly Ser Thr Val Leu Tyr Arg
1 5 10

<210> SEQ ID NO 284
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 284

Val Ser His Ser Glu Asp Asp Cys Leu Ala Phe Lys
1 5 10

<210> SEQ ID NO 285
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

Glu Val Val Ala Asp Ser Val Trp Val Asp Val Lys
1 5 10

<210> SEQ ID NO 286
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 286

Ala Pro Ser Thr Trp Leu Thr Ala Tyr Val Val Lys
1 5 10

<210> SEQ ID NO 287
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

Ser Gly Ser Asp Glu Val Gln Val Gly Gln Gln Arg
1 5 10

<210> SEQ ID NO 288
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 288

Glu Asn Glu Gly Phe Thr Val Thr Ala Glu Gly Lys
1 5 10

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 289

Gln Glu Leu Ser Glu Ala Glu Gln Ala Thr Arg
1 5 10

<210> SEQ ID NO 290
<211> LENGTH: 11
<212> TYPE: PRT
<213> ORGANISM: Artificial Sequence
<220> FEATURE:

<223> OTHER INFORMATION: Description of Artificial Sequence: Synthetic peptide

<400> SEQUENCE: 290

Ala Cys Glu Pro Gly Val Asp Tyr Val Tyr Lys
1 5 10

<210> SEQ ID NO 291
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 291

Gln Pro Val Pro Gly Gln Gln Met Thr Leu Lys
1 5 10

<210> SEQ ID NO 292
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 292

Val Thr Ile Lys Pro Ala Pro Glu Thr Glu Lys
1 5 10

<210> SEQ ID NO 293
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 293

Ile His Trp Glu Ser Ala Ser Leu Leu Arg
1 5 10

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 294

Tyr Tyr Thr Tyr Leu Ile Met Asn Lys
1 5

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 295

Asn Thr Met Ile Leu Glu Ile Cys Thr Arg
1 5 10

<210> SEQ ID NO 296
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 296

Asp Phe Asp Phe Val Pro Pro Val Val Arg
1 5 10

<210> SEQ ID NO 297
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 297

Cys Ala Glu Glu Asn Cys Phe Ile Gln Lys
1 5 10

<210> SEQ ID NO 298
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 298

Ala Glu Leu Gln Cys Pro Gln Pro Ala Ala Arg
1 5 10

<210> SEQ ID NO 299
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 299

Gln Pro Ser Ser Ala Phe Ala Ala Phe Val Lys
1 5 10

<210> SEQ ID NO 300
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 300

His Gln Gln Thr Val Thr Ile Pro Pro Lys
1 5 10

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 301

Phe Tyr Tyr Ile Tyr Asn Glu Lys
1 5

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 302

Val Leu Leu Asp Gly Val Gln Asn Pro Arg
1 5 10

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 303

Asn Thr Leu Ile Ile Tyr Leu Asp Lys
1 5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

Gly Tyr Thr Gln Gln Leu Ala Phe Arg
1 5

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 305

Asp Ser Cys Val Gly Ser Leu Val Val Lys
1 5 10

<210> SEQ ID NO 306
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

Ala Asp Ile Gly Cys Thr Pro Gly Ser Gly Lys
1 5 10

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 307

Thr Gly Leu Gln Glu Val Glu Val Lys
1 5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Phe Ile Ser Leu Gly Glu Ala Cys Lys
1 5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 309

Gly Leu Glu Val Thr Ile Thr Ala Arg
1 5

<210> SEQ ID NO 310
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 310

Ala Val Leu Tyr Asn Tyr Arg
1 5

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 311

Ile Trp Asp Val Val Glu Lys
1 5

<210> SEQ ID NO 312
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 312

Asn Glu Gln Val Glu Ile Arg
1 5

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 313

Ile Ser Leu Pro Glu Ser Leu Lys
1 5

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 314

Leu Met Asn Ile Phe Leu Lys
1 5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 315

Gln Leu Ala Asn Gly Val Asp Arg
1 5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 316

Gln Gly Ala Leu Glu Leu Ile Lys
1 5

<210> SEQ ID NO 317
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 317

Ile Phe Thr Val Asn His Lys
1 5

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 318

Ile Glu Gly Asp His Gly Ala Arg
1 5

<210> SEQ ID NO 319
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 319

Trp Leu Asn Glu Gln Arg
1 5

<210> SEQ ID NO 320
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 320

Val Val Leu Val Ala Val Asp Lys
1 5

<210> SEQ ID NO 321
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 321

Leu Pro Tyr Ser Val Val Arg
1 5

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 322

Ala Ser His Leu Gly Leu Ala Arg
1 5

<210> SEQ ID NO 323
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 323

Asp Gln Leu Thr Cys Asn Lys
1 5

<210> SEQ ID NO 324
<211> LENGTH: 6
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 324

Phe Tyr His Pro Glu Lys
1 5

<210> SEQ ID NO 325
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 325

Cys Cys Glu Asp Gly Met Arg
1 5

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 326

Thr Phe Ile Ser Pro Ile Lys
1 5

<210> SEQ ID NO 327
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 327

Ser Val Gln Leu Thr Glu Lys
1 5

<210> SEQ ID NO 328
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 328

Trp Leu Ile Leu Glu Lys
1 5

<210> SEQ ID NO 329
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 329

Ser Gly Gln Ser Glu Asp Arg
1 5

-continued

<210> SEQ ID NO 330
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 330

Gly Val Phe Val Leu Asn Lys
1 5

<210> SEQ ID NO 331
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 331

Leu Val Leu Ser Ser Glu Lys
1 5

<210> SEQ ID NO 332
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 332

Val Val Pro Glu Gly Ile Arg
1 5

<210> SEQ ID NO 333
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 333

Gln Asn Gln Glu Leu Lys
1 5

<210> SEQ ID NO 334
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 334

Val Thr Leu Glu Glu Arg
1 5

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic
peptide -continued

<400> SEQUENCE: 335

Ala Glu Asp Leu Val Gly Lys
1               5

<210> SEQ ID NO 336
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Trp Glu Asp Pro Gly Lys
1               5

<210> SEQ ID NO 337
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Thr Leu Asp Pro Glu Arg
1               5

<210> SEQ ID NO 338
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Arg Pro Gln Asp Ala Lys
1               5

<210> SEQ ID NO 339
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Phe Leu Thr Thr Ala Lys
1               5

<210> SEQ ID NO 340
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Tyr Glu Leu Asp Lys
1               5

<210> SEQ ID NO 341
<211> LENGTH: 6

<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Leu Leu Pro Val Gly Arg
1 5

<210> SEQ ID NO 342
<211> LENGTH: 30
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Glu Val Val Thr Ser Glu Asp Gly Ser Asp Cys Pro Glu Ala Met Asp
1 5 10 15

Leu Gly Thr Leu Ser Gly Ile Gly Thr Leu Asp Gly Phe Arg
20 25 30

<210> SEQ ID NO 343
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Gly Phe Gly Ser Leu Asn Asp Glu Gly Glu Gly Glu Phe Trp Leu Gly
1 5 10 15

Asn Asp Tyr Leu His Leu Leu Thr Gln Arg
20 25

<210> SEQ ID NO 344
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Ile Phe Ser Val Tyr Cys Asp Gln Glu Thr Ser Leu Gly Gly Trp Leu
1 5 10 15

Leu Ile Gln Gln Arg
20

<210> SEQ ID NO 345
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

Asp Cys Asp Asp Val Leu Gln Thr His Pro Ser Gly Thr Gln Ser Gly
1 5 10 15

Ile Phe Asn Ile Lys
20

<210> SEQ ID NO 346
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 346

Thr Phe Pro Gly Phe Phe Ser Pro Met Leu Gly Glu Phe Val Ser Glu
1 5 10 15

Thr Glu Ser Arg
20

<210> SEQ ID NO 347
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 347

Val Glu Leu Glu Asp Trp Ala Gly Asn Glu Ala Tyr Ala Glu Tyr His
1 5 10 15

Phe Arg

<210> SEQ ID NO 348
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 348

Asn Asn Ser Pro Tyr Glu Ile Glu Asn Gly Val Val Trp Val Ser Phe
1 5 10 15

Arg

<210> SEQ ID NO 349
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 349

Asn Pro Ser Ser Ala Gly Ser Trp Asn Ser Gly Ser Ser Gly Pro Gly
1 5 10 15

Ser Thr Gly Asn Arg
20

<210> SEQ ID NO 350
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 350

Asp Ser Asp Trp Pro Phe Cys Ser Asp Glu Asp Trp Asn Tyr Lys
1 5 10 15

<210> SEQ ID NO 351
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

```
Met Ala Asp Glu Ala Gly Ser Glu Ala Asp His Glu Gly Thr His Ser
1               5                   10                  15

Thr Lys
```

<210> SEQ ID NO 352
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

```
Glu Ser Ser Ser His His Pro Gly Ile Ala Glu Phe Pro Ser Arg
1               5                   10                  15
```

<210> SEQ ID NO 353
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

```
Asp Ser His Ser Leu Thr Thr Asn Ile Met Glu Ile Leu Arg
1               5                   10
```

<210> SEQ ID NO 354
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 354

```
His Pro Asp Glu Ala Ala Phe Phe Asp Thr Ala Ser Thr Gly Lys
1               5                   10                  15
```

<210> SEQ ID NO 355
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 355

```
Gly Gly Ser Thr Ser Tyr Gly Thr Gly Ser Glu Thr Glu Ser Pro Arg
1               5                   10                  15
```

<210> SEQ ID NO 356
<211> LENGTH: 13
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 356

Gly Leu Ile Asp Glu Val Asn Gln Asp Phe Thr Asn Arg
1 5 10

<210> SEQ ID NO 357
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 357

Met Glu Leu Glu Arg Pro Gly Gly Asn Glu Ile Thr Arg
1 5 10

<210> SEQ ID NO 358
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 358

Met Lys Pro Val Pro Asp Leu Val Pro Gly Asn Phe Lys
1 5 10

<210> SEQ ID NO 359
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 359

Gln Phe Thr Ser Ser Thr Ser Tyr Asn Arg
1 5 10

<210> SEQ ID NO 360
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 360

Gly Ser Glu Ser Gly Ile Phe Thr Asn Thr Lys
1 5 10

<210> SEQ ID NO 361
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 361

Val Gln His Ile Gln Leu Leu Gln Lys
1 5

<210> SEQ ID NO 362
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 362

Ala Leu Thr Asp Met Pro Gln Met Arg
1 5

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 363

Met Asp Gly Ser Leu Asn Phe Asn Arg
1 5

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 364

Asn Ser Leu Phe Glu Tyr Gln Lys
1 5

<210> SEQ ID NO 365
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 365

Val Thr Ser Gly Ser Thr Thr Thr Thr Arg
1 5 10

<210> SEQ ID NO 366
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 366

Gly Asp Phe Ser Ser Ala Asn Asn Arg
1 5

<210> SEQ ID NO 367
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 367

Leu Glu Val Asp Ile Asp Ile Lys
1 5

<210> SEQ ID NO 368
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 368

Gln Leu Glu Gln Val Ile Ala Lys
1 5

<210> SEQ ID NO 369
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 369

Asp Tyr Glu Asp Gln Gln Lys
1 5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 370

Thr Val Ile Gly Pro Asp Gly His Lys
1 5

<210> SEQ ID NO 371
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 371

Gly Asp Ser Thr Phe Glu Ser Lys
1 5

<210> SEQ ID NO 372
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 372

Gln His Leu Pro Leu Ile Lys
1 5

<210> SEQ ID NO 373
<211> LENGTH: 6
<212> TYPE: PRT
<213> ORGANISM: Artificial Sequence -continued
<220> FEATURE:
<223> OTHER INFORMATION: Description of Artificial Sequence: Synthetic
peptide

<400> SEQUENCE: 373

Thr Trp Gln Asp Tyr Lys
1 5

<210> SEQ ID NO 374
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 374

Ile Arg Pro Leu Val Thr Gln
1 5

<210> SEQ ID NO 375
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 375

Glu Tyr His Thr Glu Lys
1 5

<210> SEQ ID NO 376
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 376

Ala Gln Leu Val Asp Met Lys
1 5

<210> SEQ ID NO 377
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 377

Asp Asn Thr Tyr Asn Arg
1 5

<210> SEQ ID NO 378
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 378

Gly Ala Asp Tyr Ser Leu Arg
1 5

<210> SEQ ID NO 379
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 379

Val Pro Pro Glu Trp Lys
1 5

<210> SEQ ID NO 380
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 380

Val Ser Glu Asp Leu Arg
1 5

<210> SEQ ID NO 381
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 381

Asp Leu Leu Pro Ser Arg
1 5

<210> SEQ ID NO 382
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 382

His Gln Ser Ala Cys Lys
1 5

<210> SEQ ID NO 383
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 383

Ser Ser Ser Tyr Ser Lys
1 5

<210> SEQ ID NO 384
<211> LENGTH: 34
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 384

Tyr Gln Glu Asp Thr Cys Tyr Gly Asp Ala Gly Ser Ala Phe Ala Val
1 5 10 15

His Asp Leu Glu Glu Asp Thr Trp Tyr Ala Thr Gly Ile Leu Ser Phe
20 25 30

Asp Lys

<210> SEQ ID NO 385
<211> LENGTH: 31
<212> TYPE: PRT
<213> ORGANISM: Artificial Sequence
<220> FEATURE:
<223> OTHER INFORMATION: Description of Artificial Sequence: Synthetic peptide

<400> SEQUENCE: 385

Val Asp Ser Gly Asn Asp Val Thr Asp Ile Ala Asp Asp Gly Cys Pro
1 5 10 15

Lys Pro Pro Glu Ile Ala His Gly Tyr Val Glu His Ser Val Arg
20 25 30

<210> SEQ ID NO 386
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 386

Leu Pro Glu Cys Glu Ala Asp Asp Gly Cys Pro Lys Pro Pro Glu Ile
1 5 10 15

Ala His Gly Tyr Val Glu His Ser Val Arg
20 25

<210> SEQ ID NO 387
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 387

Met Val Ser His His Asn Leu Thr Thr Gly Ala Thr Leu Ile Asn Glu
1 5 10 15

Gln Trp Leu Leu Thr Thr Ala Lys
20

<210> SEQ ID NO 388
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 388

Ser Pro Val Gly Val Gln Pro Ile Leu Asn Glu His Thr Phe Cys Ala
1 5 10 15

Gly Met Ser Lys
20

<210> SEQ ID NO 389
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Val Val Leu His Pro Asn Tyr Ser Gln Val Asp Ile Gly Leu Ile Lys
1               5                   10                  15

<210> SEQ ID NO 390
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Tyr Val Met Leu Pro Val Ala Asp Gln Asp Gln Cys Ile Arg
1               5                   10

<210> SEQ ID NO 391
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Asn Leu Phe Leu Asn His Ser Glu Asn Ala Thr Ala Lys
1               5                   10

<210> SEQ ID NO 392
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Thr Glu Gly Asp Gly Val Tyr Thr Leu Asn Asn Glu Lys
1               5                   10

<210> SEQ ID NO 393
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Thr Glu Gly Asp Gly Val Tyr Thr Leu Asn Asp Lys
1               5                   10

<210> SEQ ID NO 394
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Asp Ile Ala Pro Thr Leu Thr Leu Tyr Val Gly Lys
1 5 10

<210> SEQ ID NO 395
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 395

Ser Cys Ala Val Ala Glu Tyr Gly Val Tyr Val Lys
1 5 10

<210> SEQ ID NO 396
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 396

Leu Pro Glu Cys Glu Ala Val Cys Gly Lys Pro Lys
1 5 10

<210> SEQ ID NO 397
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 397

Val Thr Ser Ile Gln Asp Trp Val Gln Lys
1 5 10

<210> SEQ ID NO 398
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 398

His Tyr Glu Gly Ser Thr Val Pro Glu Lys
1 5 10

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 399

Val Met Pro Ile Cys Leu Pro Ser Lys
1 5

<210> SEQ ID NO 400
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 400

Val Gly Tyr Val Ser Gly Trp Gly Arg
1 5

<210> SEQ ID NO 401
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 401

Ile Leu Gly Gly His Leu Asp Ala Lys
1 5

<210> SEQ ID NO 402
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 402

Gly Ser Phe Pro Trp Gln Ala Lys
1 5

<210> SEQ ID NO 403
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 403

Asn Pro Ala Asn Pro Val Gln Arg
1 5

<210> SEQ ID NO 404
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 404

Gln Leu Val Glu Ile Glu Lys
1 5

<210> SEQ ID NO 405
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 405

Asp Tyr Ala Glu Val Gly Arg
1 5

-continued

<210> SEQ ID NO 406
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 406

Phe Thr Asp His Leu Lys
1 5

<210> SEQ ID NO 407
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 407

Val Ser Val Asn Glu Arg
1 5

<210> SEQ ID NO 408
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 408

Gln Trp Ile Asn Lys
1 5

<210> SEQ ID NO 409
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 409

Gln Trp Ile Asn Lys
1 5

<210> SEQ ID NO 410
<211> LENGTH: 38
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 410

Ala Ile Ala Ala Asn Glu Ala Asp Ala Val Thr Leu Asp Ala Gly Leu
1 5 10 15

Val Tyr Asp Ala Tyr Leu Ala Pro Asn Asn Leu Lys Pro Val Val Ala
20 25 30

Glu Phe Tyr Gly Ser Lys
35

<210> SEQ ID NO 411
<211> LENGTH: 21

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 411

Gln Gln Gln His Leu Phe Gly Ser Asn Val Thr Asp Cys Ser Gly Asn
1 5 10 15

Phe Cys Leu Phe Arg
20

<210> SEQ ID NO 412
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 412

Ile Met Asn Gly Glu Ala Asp Ala Met Ser Leu Asp Gly Gly Phe Val
1 5 10 15

Tyr Ile Ala Gly Lys
20

<210> SEQ ID NO 413
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 413

Ser Ala Gly Trp Asn Ile Pro Ile Gly Leu Leu Tyr Cys Asp Leu Pro
1 5 10 15

Glu Pro Arg

<210> SEQ ID NO 414
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 414

Glu Asp Leu Ile Trp Glu Leu Leu Asn Gln Ala Gln Glu His Phe Gly
1 5 10 15

Lys

<210> SEQ ID NO 415
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 415

Ser Asp Asn Cys Glu Asp Thr Pro Glu Ala Gly Tyr Phe Ala Val Ala
1 5 10 15

Val Val Lys

<210> SEQ ID NO 416
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 416

Glu Gly Thr Cys Pro Glu Ala Pro Thr Asp Glu Cys Lys Pro Val Lys
1 5 10 15

<210> SEQ ID NO 417
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

Asp Cys His Leu Ala Gln Val Pro Ser His Thr Val Val Ala Arg
1 5 10 15

<210> SEQ ID NO 418
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 418

Glu Asp Pro Gln Thr Phe Tyr Tyr Ala Val Ala Val Val Lys
1 5 10

<210> SEQ ID NO 419
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 419

Ile Glu Cys Val Ser Ala Glu Thr Thr Glu Asp Cys Ile Ala Lys
1 5 10 15

<210> SEQ ID NO 420
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 420

Leu Cys Met Gly Ser Gly Leu Asn Leu Cys Glu Pro Asn Asn Lys
1 5 10 15

<210> SEQ ID NO 421
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 421

Thr Ala Gly Trp Asn Ile Pro Met Gly Leu Leu Tyr Asn Lys
1 5 10

<210> SEQ ID NO 422
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 422

Lys Pro Val Glu Glu Tyr Ala Asn Cys His Leu Ala Arg
1 5 10

<210> SEQ ID NO 423
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 423

Phe Asp Glu Phe Phe Ser Glu Gly Cys Ala Pro Gly Ser Lys
1 5 10

<210> SEQ ID NO 424
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 424

Asp Gln Tyr Glu Leu Leu Cys Leu Asp Asn Thr Arg
1 5 10

<210> SEQ ID NO 425
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 425

Met Tyr Leu Gly Tyr Glu Tyr Val Thr Ala Ile Arg
1 5 10

<210> SEQ ID NO 426
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 426

Cys Gly Leu Val Pro Val Leu Ala Glu Asn Tyr Asn Lys
1 5 10

<210> SEQ ID NO 427
<211> LENGTH: 13
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 427

Cys Ser Thr Ser Ser Leu Leu Glu Ala Cys Thr Phe Arg
1 5 10

<210> SEQ ID NO 428
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 428

Ser Val Ile Pro Ser Asp Gly Pro Ser Val Ala Cys Val Lys
1 5 10

<210> SEQ ID NO 429
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 429

Asp Tyr Glu Leu Leu Cys Leu Asp Gly Thr Arg
1 5 10

<210> SEQ ID NO 430
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 430

Glu Gly Tyr Tyr Gly Tyr Thr Gly Ala Phe Arg
1 5 10

<210> SEQ ID NO 431
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 431

Glu Phe Gln Leu Phe Ser Ser Pro His Gly Lys
1 5 10

<210> SEQ ID NO 432
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 432

His Ser Thr Ile Phe Glu Asn Leu Ala Asn Lys
1 5 10

<210> SEQ ID NO 433
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 433

Trp Cys Ala Val Ser Glu His Glu Ala Thr Lys
1 5 10

<210> SEQ ID NO 434
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 434

Ser Ala Ser Asp Leu Thr Trp Asp Asn Leu Lys
1 5 10

<210> SEQ ID NO 435
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 435

Cys Asp Glu Trp Ser Val Asn Ser Val Gly Lys
1 5 10

<210> SEQ ID NO 436
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 436

Asp Ser Gly Phe Gln Met Asn Gln Leu Arg
1 5 10

<210> SEQ ID NO 437
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 437

His Gln Thr Val Pro Gln Asn Thr Gly Gly Lys
1 5 10

<210> SEQ ID NO 438
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 438

Trp Cys Ala Leu Ser His His Glu Arg
1 5

<210> SEQ ID NO 439
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 439

Tyr Leu Gly Glu Glu Tyr Val Lys
1 5

<210> SEQ ID NO 440
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 440

Asp Gly Ala Gly Asp Val Ala Phe Val Lys
1 5 10

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 441

Ala Pro Asn His Ala Val Val Thr Arg
1 5

<210> SEQ ID NO 442
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 442

Ala Ser Tyr Leu Asp Cys Ile Arg
1 5

<210> SEQ ID NO 443
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 443

Lys Pro Val Asp Glu Tyr Lys
1 5

<210> SEQ ID NO 444
<211> LENGTH: 8

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 444

Asp Ser Ala His Gly Phe Leu Lys
1 5

<210> SEQ ID NO 445
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 445

Asp Asp Thr Val Cys Leu Ala Lys
1 5

<210> SEQ ID NO 446
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 446

Ser Cys His Thr Gly Leu Gly Arg
1 5

<210> SEQ ID NO 447
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 447

Ser Cys His Thr Ala Val Gly Arg
1 5

<210> SEQ ID NO 448
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 448

Asn Pro Asp Pro Trp Ala Lys
1 5

<210> SEQ ID NO 449
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 449

Gly Asp Val Ala Phe Val Lys

```
<210> SEQ ID NO 450
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Glu Ala Cys Val His Lys
1               5

<210> SEQ ID NO 451
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Asp Leu Leu Phe Arg
1               5

<210> SEQ ID NO 452
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Asn Thr Tyr Glu Lys
1               5

<210> SEQ ID NO 453
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Asp Ser Ser Leu Cys Lys
1               5

<210> SEQ ID NO 454
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Thr Ser Glu Ser Gly Glu Leu His Gly Leu Thr Thr Glu Glu Glu Phe
1               5                   10                  15

Val Glu Gly Ile Tyr Lys
            20

<210> SEQ ID NO 455
<211> LENGTH: 23
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 455

Ala Leu Gly Ile Ser Pro Phe His Glu His Ala Glu Val Val Phe Thr
1 5 10 15

Ala Asn Asp Ser Gly Pro Arg
20

<210> SEQ ID NO 456
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 456

Tyr Thr Ile Ala Ala Leu Leu Ser Pro Tyr Ser Tyr Ser Thr Thr Ala
1 5 10 15

Val Val Thr Asn Pro Lys
20

<210> SEQ ID NO 457
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 457

Ala Ala Asp Asp Thr Trp Glu Pro Phe Ala Ser Gly Lys
1 5 10

<210> SEQ ID NO 458
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 458

Gly Ser Pro Ala Ile Asn Val Ala Val His Val Phe Arg
1 5 10

<210> SEQ ID NO 459
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 459

Gly Pro Thr Gly Thr Gly Glu Ser Lys
1 5

<210> SEQ ID NO 460
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 460

Val Glu Ile Asp Thr Lys
1 5

<210> SEQ ID NO 461
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 461

Cys Pro Leu Met Val Lys
1 5

<210> SEQ ID NO 462
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 462

Val Leu Asp Ala Val Arg
1 5

<210> SEQ ID NO 463
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 463

Phe Leu Glu Gln Gln Asn Gln Val Leu Gln Thr Lys
1 5 10

<210> SEQ ID NO 464
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 464

Gln Ile Ser Asn Leu Gln Gln Ser Ile Ser Asp Ala Glu Gln Arg
1 5 10 15

<210> SEQ ID NO 465
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 465

Asp Ile Glu Asn Gln Tyr Glu Thr Gln Ile Thr Gln Ile Glu His Glu
1 5 10 15

Val Ser Ser Ser Gly Gln Glu Val Gln Ser Ser Ala Lys
20 25

<210> SEQ ID NO 466
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 466

Gly Ser Tyr Gly Ser Gly Gly Ser Ser Tyr Gly Ser Gly Gly Gly Ser
1 5 10 15

Tyr Gly Ser Gly Gly Gly Gly Gly Gly His Gly Ser Tyr Gly Ser Gly
20 25 30

Ser Ser Ser Gly Gly Tyr Arg
35

<210> SEQ ID NO 467
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 467

Gly Gly Ser Gly Gly Ser His Gly Gly Gly Ser Gly Phe Gly Gly Glu
1 5 10 15

Ser Gly Gly Ser Tyr Gly Gly Gly Glu Glu Ala Ser Gly Ser Gly Gly
20 25 30

Gly Tyr Gly Gly Gly Ser Gly Lys
35 40

<210> SEQ ID NO 468
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 468

Trp Glu Leu Leu Gln Gln Val Asp Thr Ser Thr Arg
1 5 10

<210> SEQ ID NO 469
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 469

Glu Leu Thr Thr Glu Ile Asp Asn Asn Ile Glu Gln Ile Ser Ser Tyr
1 5 10 15

Lys

<210> SEQ ID NO 470
<211> LENGTH: 31
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 470

Gly Gly Gly Gly Gly Gly Tyr Gly Ser Gly Gly Ser Ser Tyr Gly Ser
1 5 10 15

Gly Gly Gly Ser Tyr Gly Ser Gly Gly Gly Gly Gly Gly Gly Arg
20 25 30

<210> SEQ ID NO 471
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 471

Val Gln Ala Leu Glu Glu Ala Asn Asn Asp Leu Glu Asn Lys
1 5 10

<210> SEQ ID NO 472
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 472

Glu Ile Glu Thr Tyr His Asn Leu Leu Glu Gly Gly Gln Glu Asp Phe
1 5 10 15

Glu Ser Ser Gly Ala Gly Lys
20

<210> SEQ ID NO 473
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 473

Ser Leu Asn Asn Gln Phe Ala Ser Phe Ile Asp Lys
1 5 10

<210> SEQ ID NO 474
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 474

Gly Ser Leu Gly Gly Gly Phe Ser Ser Gly Gly Phe Ser Gly Gly Ser
1 5 10 15

Phe Ser Arg

<210> SEQ ID NO 475
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 475

Ala Leu Glu Glu Ser Asn Tyr Glu Leu Glu Gly Lys
1 5 10

<210> SEQ ID NO 476
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 476

Leu Asn Asp Leu Glu Asp Ala Leu Gln Gln Ala Lys
1 5 10

<210> SEQ ID NO 477
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 477

His Gly Val Gln Glu Leu Glu Ile Glu Leu Gln Ser Gln Leu Ser Lys
1 5 10 15

<210> SEQ ID NO 478
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 478

Tyr Glu Glu Leu Gln Ile Thr Ala Gly Arg
1 5 10

<210> SEQ ID NO 479
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 479

Ser Leu Asp Leu Asp Ser Ile Ile Ala Glu Val Lys
1 5 10

<210> SEQ ID NO 480
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 480

Thr Ser Gln Asn Ser Glu Leu Asn Asn Met Gln Asp Leu Val Glu Asp
1 5 10 15

Tyr Lys Lys

<210> SEQ ID NO 481

<211> LENGTH: 32
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 481

Gly Gly Gly Gly Ser Phe Gly Tyr Ser Tyr Gly Gly Gly Ser Gly Gly
1 5 10 15

Gly Phe Ser Ala Ser Ser Leu Gly Gly Gly Phe Gly Gly Gly Ser Arg
20 25 30

<210> SEQ ID NO 482
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 482

Ser Gly Gly Gly Phe Ser Ser Gly Ser Ala Gly Ile Ile Asn Tyr Gln
1 5 10 15

Arg

<210> SEQ ID NO 483
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 483

Ser Asp Leu Glu Met Gln Tyr Glu Thr Leu Gln Glu Glu Leu Met Ala
1 5 10 15

Leu Lys

<210> SEQ ID NO 484
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 484

Asn Gln Ile Leu Asn Leu Thr Thr Asp Asn Ala Asn Ile Leu Leu Gln
1 5 10 15

Ile Asp Asn Ala Arg
20

<210> SEQ ID NO 485
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 485

Thr Leu Asn Asp Met Arg Gln Glu Tyr Glu Gln Leu Ile Ala Lys
1 5 10 15

<210> SEQ ID NO 486
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 486

Thr His Asn Leu Glu Pro Tyr Phe Glu Ser Phe Ile Asn Asn Leu Arg
1 5 10 15

<210> SEQ ID NO 487
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 487

Thr Asn Ala Glu Asn Glu Phe Val Thr Ile Lys Lys
1 5 10

<210> SEQ ID NO 488
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 488

Asn Val Ser Thr Gly Asp Val Asn Val Glu Met Asn Ala Ala Pro Gly
1 5 10 15

Val Asp Leu Thr Gln Leu Leu Asn Asn Met Arg
20 25

<210> SEQ ID NO 489
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 489

Gln Ser Val Glu Ala Asp Ile Asn Gly Leu Arg Arg
1 5 10

<210> SEQ ID NO 490
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 490

Ser Leu Asn Asn Gln Phe Ala Ser Phe Ile Asp Lys Val Arg
1 5 10

<210> SEQ ID NO 491
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 491

Asn Val Gln Ala Leu Glu Ile Glu Leu Gln Ser Gln Leu Ala Leu Lys
1 5 10 15

<210> SEQ ID NO 492
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 492

Gln Ser Leu Glu Ala Ser Leu Ala Glu Thr Glu Gly Arg
1 5 10

<210> SEQ ID NO 493
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 493

Asn Tyr Ser Pro Tyr Tyr Asn Thr Ile Asp Asp Leu Lys Asp Gln Ile
1 5 10 15

Val Asp Leu Thr Val Gly Asn Asn Lys
20 25

<210> SEQ ID NO 494
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 494

Thr Asn Ala Glu Asn Glu Phe Val Thr Ile Lys
1 5 10

<210> SEQ ID NO 495
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 495

Ile Arg Leu Glu Asn Glu Ile Gln Thr Tyr Arg
1 5 10

<210> SEQ ID NO 496
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 496

Ser Lys Glu Leu Thr Thr Glu Ile Asp Asn Asn Ile Glu Gln Ile Ser
1 5 10 15

Ser Tyr Lys

<210> SEQ ID NO 497
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 497

Leu Lys Tyr Glu Asn Glu Val Ala Leu Arg
1 5 10

<210> SEQ ID NO 498
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 498

Ala Asp Leu Glu Met Gln Ile Glu Ser Leu Thr Glu Glu Leu Ala Tyr
1 5 10 15

Leu Lys

<210> SEQ ID NO 499
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 499

Ile Glu Ile Ser Glu Leu Asn Arg
1 5

<210> SEQ ID NO 500
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 500

Ser Leu Val Asn Leu Gly Gly Ser Lys Ser Ile Ser Ile Ser Val Ala
1 5 10 15

Arg

<210> SEQ ID NO 501
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 501

Met Ser Gly Glu Cys Ala Pro Asn Val Ser Val Ser Val Ser Thr Ser
1 5 10 15

His Thr Thr Ile Ser Gly Gly Gly Ser Arg
20 25

<210> SEQ ID NO 502
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 502

Phe Ser Ser Ser Gly Gly Gly Gly Gly Ser Phe Gly Ala Gly Gly Gly
1 5 10 15

Phe Gly Ser Arg
20

<210> SEQ ID NO 503
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 503

Leu Ala Leu Asp Leu Glu Ile Ala Thr Tyr Arg
1 5 10

<210> SEQ ID NO 504
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 504

Val Leu Tyr Asp Ala Glu Ile Ser Gln Ile His Gln Ser Val Thr Asp
1 5 10 15

Thr Asn Val Ile Leu Ser Met Asp Asn Ser Arg
20 25

<210> SEQ ID NO 505
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 505

Leu Ala Ser Tyr Leu Asp Lys Val Gln Ala Leu Glu Glu Ala Asn Asn
1 5 10 15

Asp Leu Glu Asn Lys
20

<210> SEQ ID NO 506
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 506

Gln Gly Val Asp Ala Asp Ile Asn Gly Leu Arg
1 5 10

<210> SEQ ID NO 507
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 507

Thr Ile Asp Asp Leu Lys Asn Gln Ile Leu Asn Leu Thr Thr Asp Asn
1 5 10 15

Ala Asn Ile Leu Leu Gln Ile Asp Asn Ala Arg
20 25

<210> SEQ ID NO 508
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 508

Ala Glu Thr Glu Cys Gln Asn Thr Glu Tyr Gln Gln Leu Leu Asp Ile
1 5 10 15

Lys

<210> SEQ ID NO 509
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 509

Gly Gly Ser Gly Gly Ser Tyr Gly Gly Gly Gly Ser Gly Gly Gly Tyr
1 5 10 15

Gly Gly Gly Ser Gly Ser Arg
20

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 510

Tyr Leu Asp Gly Leu Thr Ala Glu Arg
1 5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 511

Asp Ala Glu Ala Trp Phe Asn Glu Lys
1 5

```
<210> SEQ ID NO 512
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Asn Met Gln Asp Met Val Glu Asp Tyr Arg
1               5                   10


<210> SEQ ID NO 513
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Val Asp Leu Leu Asn Gln Glu Ile Glu Phe Leu Lys
1               5                   10


<210> SEQ ID NO 514
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Gly Gly Gly Phe Gly Gly Gly Ser Ser Phe Gly Gly Gly Ser Gly Phe
1               5                   10                  15

Ser Gly Gly Gly Phe Gly Gly Gly Gly Phe Gly Gly Gly Arg
            20                  25                  30


<210> SEQ ID NO 515
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Leu Glu Asn Glu Ile Gln Thr Tyr Arg
1               5


<210> SEQ ID NO 516
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Gln Glu Tyr Glu Gln Leu Ile Ala Lys
1               5


<210> SEQ ID NO 517
<211> LENGTH: 9
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 517

Thr Leu Leu Asp Ile Asp Asn Thr Arg
1 5

<210> SEQ ID NO 518
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 518

Asn Lys Leu Asn Asp Leu Glu Asp Ala Leu Gln Gln Ala Lys
1 5 10

<210> SEQ ID NO 519
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 519

Asn Leu Asp Leu Asp Ser Ile Ile Ala Glu Val Lys
1 5 10

<210> SEQ ID NO 520
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 520

Asn Val Gln Asp Ala Ile Ala Asp Ala Glu Gln Arg
1 5 10

<210> SEQ ID NO 521
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 521

Gln Val Leu Asp Asn Leu Thr Met Glu Lys
1 5 10

<210> SEQ ID NO 522
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 522

Gln Ser Val Glu Ala Asp Ile Asn Gly Leu Arg
1 5 10

<210> SEQ ID NO 523
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 523

Ser Gln Tyr Glu Gln Leu Ala Glu Gln Asn Arg
1 5 10

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 524

Leu Ala Ser Tyr Leu Asp Lys Val Arg
1 5

<210> SEQ ID NO 525
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 525

Ala Glu Ala Glu Ser Leu Tyr Gln Ser Lys Tyr Glu Glu Leu Gln Ile
1 5 10 15

Thr Ala Gly Arg
20

<210> SEQ ID NO 526
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 526

Gly Ser Gly Gly Gly Ser Ser Gly Gly Ser Ile Gly Gly Arg
1 5 10

<210> SEQ ID NO 527
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 527

Ser Gly Gly Gly Gly Gly Gly Gly Leu Gly Ser Gly Gly Ser Ile Arg
1 5 10 15

<210> SEQ ID NO 528
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 528

Thr Ala Ala Glu Asn Asp Phe Val Thr Leu Lys Lys
1 5 10

<210> SEQ ID NO 529
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 529

Ser Lys Ala Glu Ala Glu Ser Leu Tyr Gln Ser Lys Tyr Glu Glu Leu
1 5 10 15

Gln Ile Thr Ala Gly Arg
20

<210> SEQ ID NO 530
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 530

Ala Asp Leu Glu Met Gln Ile Glu Ser Leu Thr Glu Glu Leu Ala Tyr
1 5 10 15

Leu Lys Lys

<210> SEQ ID NO 531
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 531

Leu Asn Asp Leu Glu Asp Ala Leu Gln Gln Ala Lys Glu Asp Leu Ala
1 5 10 15

Arg

<210> SEQ ID NO 532
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 532

His Gly Gly Gly Gly Gly Gly Phe Gly Gly Gly Gly Phe Gly Ser Arg
1 5 10 15

<210> SEQ ID NO 533
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 533

Ala Glu Ala Glu Ser Leu Tyr Gln Ser Lys
1 5 10

<210> SEQ ID NO 534
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 534

Asp Tyr Gln Glu Leu Met Asn Thr Lys
1 5

<210> SEQ ID NO 535
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 535

Phe Ala Ser Phe Ile Asp Lys Val Arg
1 5

<210> SEQ ID NO 536
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 536

Gly Phe Ser Ser Gly Ser Ala Val Val Ser Gly Gly Ser Arg
1 5 10

<210> SEQ ID NO 537
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 537

Gly Gly Ser Gly Gly Gly Gly Gly Gly Ser Ser Gly Gly Arg Gly Ser
1 5 10 15

Gly Gly Gly Ser Ser Gly Gly Ser Ile Gly Gly Arg
20 25

<210> SEQ ID NO 538
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 538

Gly Ser Ser Gly Gly Gly Cys Phe Gly Gly Ser Ser Gly Gly Tyr Gly
1 5 10 15

Gly Leu Gly Gly Phe Gly Gly Gly Ser Phe Arg 20 25

<210> SEQ ID NO 539
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 539

His Gly Val Gln Glu Leu Glu Ile Glu Leu Gln Ser Gln Leu Ser Lys
1 5 10 15

Lys

<210> SEQ ID NO 540
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 540

Ile Ser Ser Ser Lys Gly Ser Leu Gly Gly Gly Phe Ser Ser Gly Gly
1 5 10 15

Phe Ser Gly Gly Ser Phe Ser Arg
20

<210> SEQ ID NO 541
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 541

Met Ser Cys Arg Gln Phe Ser Ser Ser Tyr Leu Thr Ser Gly Gly Gly
1 5 10 15

Gly Gly Gly Gly Leu Gly Ser Gly Gly Ser Ile Arg
20 25

<210> SEQ ID NO 542
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 542

Met Ser Gly Asp Leu Ser Ser Asn Val Thr Val Ser Val Thr Ser Ser
1 5 10 15

Thr Ile Ser Ser Asn Val Ala Ser Lys
20 25

<210> SEQ ID NO 543
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 543

Met Thr Leu Asp Asp Phe Arg
1 5

<210> SEQ ID NO 544
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 544

Asn Lys Leu Asn Asp Leu Glu Glu Ala Leu Gln Gln Ala Lys
1 5 10

<210> SEQ ID NO 545
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 545

Gln Ser Gly Ser Arg Gly Gly Ser Gly Gly Gly Gly Ser Ile Ser Gly
1 5 10 15

Gly Gly Tyr Gly Ser Gly Gly Gly Ser Gly Gly Arg
20 25

<210> SEQ ID NO 546
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 546

Ser Gly Gly Gly Gly Gly Gly Gly Gly Cys Gly Gly Gly Gly Gly Val
1 5 10 15

Ser Ser Leu Arg
20

<210> SEQ ID NO 547
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 547

Ser Ile Ser Ile Ser Val Ala Gly Gly Gly Gly Gly Phe Gly Ala Ala
1 5 10 15

Gly Gly Phe Gly Gly Arg
20

<210> SEQ ID NO 548
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 548

```
Thr Leu Leu Glu Gly Glu Glu Ser Arg
1               5


<210> SEQ ID NO 549
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Val Leu Asp Glu Leu Thr Leu Thr Lys
1               5


<210> SEQ ID NO 550
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Glu Glu Met Ser Gln Leu Thr Gly Gln Asn Ser Gly Asp Val Asn Val
1               5                   10                  15

Glu Ile Asn Val Ala Pro Gly Lys
            20


<210> SEQ ID NO 551
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Met Ser Cys Val Ala Arg Ser Gly Gly Ala Gly Gly Gly Ala Cys Gly
1               5                   10                  15

Phe Arg


<210> SEQ ID NO 552
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Asn His Lys Glu Glu Met Ser Gln Leu Thr Gly Gln Asn Ser Gly Asp
1               5                   10                  15

Val Asn Val Glu Ile Asn Val Ala Pro Gly Lys
            20                  25


<210> SEQ ID NO 553
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553
```

Phe Ser Ser Cys Gly Gly Gly Gly Gly Ser Phe Gly Ala Gly Gly Gly
1 5 10 15

Phe Gly Ser Arg Ser Leu Val Asn Leu Gly Gly Ser Lys
20 25

<210> SEQ ID NO 554
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 554

Phe Ser Ser Ser Gly Gly Gly Gly Gly Gly Gly Arg Phe Ser Ser Ser
1 5 10 15

Ser Gly Tyr Gly Gly Gly Ser Ser Arg
20 25

<210> SEQ ID NO 555
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 555

Gly Gly Ser Gly Gly Gly Gly Gly Gly Ser Ser Gly Gly Arg
1 5 10

<210> SEQ ID NO 556
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 556

Gly Gly Ser Gly Gly Gly Tyr Gly Ser Gly Cys Gly Gly Gly Gly Gly
1 5 10 15

Ser Tyr Gly Gly Ser Gly Arg Ser Gly Arg
20 25

<210> SEQ ID NO 557
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 557

Gly Gly Ser Ile Ser Gly Gly Gly Tyr Gly Ser Gly Gly Gly Lys
1 5 10 15

<210> SEQ ID NO 558
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 558

Gly Gly Ser Ile Ser Gly Gly Gly Tyr Gly Ser Gly Gly Gly Lys His
1 5 10 15

Ser Ser Gly Gly Gly Ser Arg
20

<210> SEQ ID NO 559
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 559

Gly Ser Ser Ser Gly Gly Val Lys Ser Ser Gly Gly Ser Ser Ser Val
1 5 10 15

Arg

<210> SEQ ID NO 560
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 560

His Tyr Ser Ser Ser Arg
1 5

<210> SEQ ID NO 561
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 561

Ile Gly Leu Gly Gly Arg Gly Gly Ser Gly Gly Ser Tyr Gly Arg Gly
1 5 10 15

Ser Arg

<210> SEQ ID NO 562
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 562

Leu Asp Ser Glu Leu Lys Asn Met Gln Asp Met Val Glu Asp Tyr Arg
1 5 10 15

<210> SEQ ID NO 563
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 563

Leu Asn Asp Leu Glu Glu Ala Leu Gln Gln Ala Lys
1 5 10

<210> SEQ ID NO 564
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 564

Leu Asn Val Glu Val Asp Ala Ala Pro Thr Val Asp Leu Asn Arg
1 5 10 15

<210> SEQ ID NO 565
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 565

Leu Val Val Gln Ile Asp Asn Ala Lys
1 5

<210> SEQ ID NO 566
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 566

Asn Tyr Ser Pro Tyr Tyr Asn Thr Ile Asp Asp Leu Lys
1 5 10

<210> SEQ ID NO 567
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 567

Gln Glu Ile Glu Cys Gln Asn Gln Glu Tyr Ser Leu Leu Leu Ser Ile
1 5 10 15

Lys

<210> SEQ ID NO 568
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 568

Gln Phe Ser Ser Ser Tyr Leu Ser Arg
1 5

<210> SEQ ID NO 569
<211> LENGTH: 17
<212> TYPE: PRT
<213> ORGANISM: Artificial Sequence
<220> FEATURE:

<223> OTHER INFORMATION: Description of Artificial Sequence: Synthetic peptide

<400> SEQUENCE: 569

Gln Leu Asp Ser Leu Leu Gly Glu Arg Gly Asn Leu Glu Gly Glu Leu
1 5 10 15

Lys

<210> SEQ ID NO 570
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 570

Arg Ser Gly Gly Gly Gly Gly Arg Phe Ser Ser Cys Gly Gly Gly Gly
1 5 10 15

Gly Ser Phe Gly Ala Gly Gly Gly Phe Gly Ser Arg
20 25

<210> SEQ ID NO 571
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 571

Arg Val Leu Asp Glu Leu Thr Leu Thr Lys
1 5 10

<210> SEQ ID NO 572
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 572

Ser Asp Leu Glu Ala Gln Val Glu Ser Leu Lys
1 5 10

<210> SEQ ID NO 573
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 573

Ser Glu Ile Thr Glu Leu Arg Arg
1 5

<210> SEQ ID NO 574
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 574

Ser Gly Gly Gly Gly Gly Gly Gly Gly Cys Gly Gly Gly Gly Gly Val
1 5 10 15

Ser Ser Leu Arg Ile Ser Ser Ser Lys
20 25

<210> SEQ ID NO 575
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 575

Ser Met Gln Asp Val Val Glu Asp Tyr Lys
1 5 10

<210> SEQ ID NO 576
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 576

Ser Thr Ser Ser Phe Ser Cys Leu Ser Arg
1 5 10

<210> SEQ ID NO 577
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 577

Thr Ala Ala Glu Asn Asp Phe Val Thr Leu Lys
1 5 10

<210> SEQ ID NO 578
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 578

Thr Gly Ser Glu Asn Asp Phe Val Val Leu Lys Lys
1 5 10

<210> SEQ ID NO 579
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 579

Val Thr Met Gln Asn Leu Asn Asp Arg
1 5

<210> SEQ ID NO 580

<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 580

Ala Leu Val Leu Ile Ala Phe Ala Gln Tyr Leu Gln Gln Cys Pro Phe
1 5 10 15

Glu Asp His Val Lys
20

<210> SEQ ID NO 581
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 581

Ala Val Met Asp Asp Phe Ala Ala Phe Val Glu Lys
1 5 10

<210> SEQ ID NO 582
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 582

Asp Val Phe Leu Gly Met Phe Leu Tyr Glu Tyr Ala Arg
1 5 10

<210> SEQ ID NO 583
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 583

Glu Thr Tyr Gly Glu Met Ala Asp Cys Cys Ala Lys
1 5 10

<210> SEQ ID NO 584
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 584

Phe Gln Asn Ala Leu Leu Val Arg
1 5

<210> SEQ ID NO 585
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 585

His Pro Tyr Phe Tyr Ala Pro Glu Leu Leu Phe Phe Ala Lys
1 5 10

<210> SEQ ID NO 586
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 586

Lys Gln Thr Ala Leu Val Glu Leu Val Lys
1 5 10

<210> SEQ ID NO 587
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 587

Lys Val Pro Gln Val Ser Thr Pro Thr Leu Val Glu Val Ser Arg
1 5 10 15

<210> SEQ ID NO 588
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 588

Leu Asp Glu Leu Arg Asp Glu Gly Lys
1 5

<210> SEQ ID NO 589
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 589

Leu Val Asn Glu Val Thr Glu Phe Ala Lys
1 5 10

<210> SEQ ID NO 590
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 590

Arg His Pro Asp Tyr Ser Val Val Leu Leu Leu Arg
1 5 10

<210> SEQ ID NO 591
<211> LENGTH: 15

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 591

Arg His Pro Tyr Phe Tyr Ala Pro Glu Leu Leu Phe Phe Ala Lys
1 5 10 15

<210> SEQ ID NO 592
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 592

Arg Pro Cys Phe Ser Ala Leu Glu Val Asp Glu Thr Tyr Val Pro Lys
1 5 10 15

<210> SEQ ID NO 593
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 593

Val Phe Asp Glu Phe Lys Pro Leu Val Glu Glu Pro Gln Asn Leu Ile
1 5 10 15

Lys

<210> SEQ ID NO 594
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 594

Val Pro Gln Val Ser Thr Pro Thr Leu Val Glu Val Ser Arg
1 5 10

<210> SEQ ID NO 595
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 595

Tyr Ile Cys Glu Asn Gln Asp Ser Ile Ser Ser Lys
1 5 10

<210> SEQ ID NO 596
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 596

Tyr Leu Tyr Glu Ile Ala Arg
1 5

<210> SEQ ID NO 597
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 597

Ala Val Leu Asp Val Phe Glu Glu Gly Thr Glu Ala Ser Ala Ala Thr
1 5 10 15

Ala Val Lys

<210> SEQ ID NO 598
<211> LENGTH: 30
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 598

Ala Val Leu Thr Ile Asp Glu Lys Gly Thr Glu Ala Ala Gly Ala Met
1 5 10 15

Phe Leu Glu Ala Ile Pro Met Ser Ile Pro Pro Glu Val Lys
20 25 30

<210> SEQ ID NO 599
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 599

Asp Leu Asp Ser Gln Thr Met Met Val Leu Val Asn Tyr Ile Phe Phe
1 5 10 15

Lys

<210> SEQ ID NO 600
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 600

Asp Thr Glu Glu Glu Asp Phe His Val Asp Gln Ala Thr Thr Val Lys
1 5 10 15

<210> SEQ ID NO 601
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 601

Asp Thr Glu Glu Glu Asp Phe His Val Asp Gln Val Thr Thr Val Lys 1 5 10 15

<210> SEQ ID NO 602
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 602

Asp Tyr Asn Leu Asn Asp Ile Leu Leu Gln Leu Gly Ile Glu Glu Ala
1 5 10 15

Phe Thr Ser Lys
20

<210> SEQ ID NO 603
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 603

Glu Leu Asp Arg Asp Thr Val Phe Ala Leu Val Asn Tyr Ile Phe Phe
1 5 10 15

Lys

<210> SEQ ID NO 604
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 604

Phe Asn Lys Pro Phe Val Phe Leu Met Ile Glu Gln Asn Thr Lys
1 5 10 15

<210> SEQ ID NO 605
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 605

Phe Asn Lys Pro Phe Val Phe Leu Met Ile Glu Gln Asn Thr Lys Ser
1 5 10 15

Pro Leu Phe Met Gly Lys
20

<210> SEQ ID NO 606
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 606

Phe Asn Arg Pro Phe Leu Met Ile Ile Val Pro Thr Asp Thr Gln Asn
1 5 10 15

Ile Phe Phe Met Ser Lys
20

<210> SEQ ID NO 607
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 607

Gly Thr Glu Ala Ala Gly Ala Met Phe Leu Glu Ala Ile Pro Met Ser
1 5 10 15

Ile Pro Pro Glu Val Lys
20

<210> SEQ ID NO 608
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 608

Gly Thr His Val Asp Leu Gly Leu Ala Ser Ala Asn Val Asp Phe Ala
1 5 10 15

Phe Ser Leu Tyr Lys
20

<210> SEQ ID NO 609
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 609

Ile Thr Pro Asn Leu Ala Glu Phe Ala Phe Ser Leu Tyr Arg
1 5 10

<210> SEQ ID NO 610
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 610

Leu Gln His Leu Glu Asn Glu Leu Thr His Asp Ile Ile Thr Lys
1 5 10 15

<210> SEQ ID NO 611
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 611

Leu Gln His Leu Val Asn Glu Leu Thr His Asp Ile Ile Thr Lys
1 5 10 15

<210> SEQ ID NO 612
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 612

Leu Ser Ile Thr Gly Thr Tyr Asp Leu Lys
1 5 10

<210> SEQ ID NO 613
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 613

Leu Ser Ile Thr Gly Thr Tyr Asp Leu Lys Ser Val Leu Gly Gln Leu
1 5 10 15

Gly Ile Thr Lys
20

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 614

Leu Ser Ser Trp Val Leu Leu Met Lys
1 5

<210> SEQ ID NO 615
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 615

Leu Tyr Gly Ser Glu Ala Phe Ala Thr Asp Phe Gln Asp Ser Ala Ala
1 5 10 15

Ala Lys

<210> SEQ ID NO 616
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 616

Leu Tyr His Ser Glu Ala Phe Thr Val Asn Phe Gly Asp Thr Glu Glu
1 5 10 15

Ala Lys

<210> SEQ ID NO 617
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

```
Leu Tyr His Ser Glu Ala Phe Thr Val Asn Phe Gly Asp Thr Glu Glu
1               5                   10                  15

Ala Lys Lys
```

<210> SEQ ID NO 618
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

```
Ser Ala Ser Leu His Leu Pro Lys Leu Ser Ile Thr Gly Thr Tyr Asp
1               5                   10                  15

Leu Lys Ser Val Leu Gly Gln Leu Gly Ile Thr Lys
            20                  25
```

<210> SEQ ID NO 619
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

```
Ser Pro Leu Phe Met Gly Lys
1               5
```

<210> SEQ ID NO 620
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

```
Ser Val Leu Gly Gln Leu Gly Ile Thr Lys
1               5                   10
```

<210> SEQ ID NO 621
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

```
Ser Val Leu Gly Gln Leu Gly Ile Thr Lys Val Phe Ser Asn Gly Ala
1               5                   10                  15

Asp Leu Ser Gly Val Thr Glu Glu Ala Pro Leu Lys
            20                  25
```

<210> SEQ ID NO 622

<211> LENGTH: 31
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 622

Ser Val Leu Gly Gln Leu Gly Ile Thr Lys Val Phe Ser Asn Gly Ala
1 5 10 15

Asp Leu Ser Gly Val Thr Glu Glu Ala Pro Leu Lys Leu Ser Lys
20 25 30

<210> SEQ ID NO 623
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 623

Thr Leu Asn Gln Pro Asp Ser Gln Leu Gln Leu Thr Thr Gly Asn Gly
1 5 10 15

Leu Phe Leu Ser Glu Gly Leu Lys
20

<210> SEQ ID NO 624
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 624

Val Phe Ser Asn Gly Ala Asp Leu Ser Gly Val Thr Glu Glu Ala Pro
1 5 10 15

Leu Lys

<210> SEQ ID NO 625
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 625

Val Phe Ser Asn Gly Ala Asp Leu Ser Gly Val Thr Glu Glu Ala Pro
1 5 10 15

Leu Lys Leu Ser Lys
20

<210> SEQ ID NO 626
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 626

Trp Glu Arg Pro Phe Glu Val Lys
1 5

<210> SEQ ID NO 627
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 627

Ala Glu Leu Gln Glu Gly Ala Arg
1 5

<210> SEQ ID NO 628
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 628

Ala Lys Pro Ala Leu Glu Asp Leu Arg
1 5

<210> SEQ ID NO 629
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 629

Asp Leu Ala Thr Val Tyr Val Asp Val Leu Lys
1 5 10

<210> SEQ ID NO 630
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 630

Asp Leu Ala Thr Val Tyr Val Asp Val Leu Lys Asp Ser Gly Arg
1 5 10 15

<210> SEQ ID NO 631
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 631

Asp Leu Ala Thr Val Tyr Val Asp Val Leu Lys Asp Ser Gly Arg Asp
1 5 10 15

Tyr Val Ser Gln Phe Glu Gly Ser Ala Leu Gly Lys
20 25

<210> SEQ ID NO 632
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 632

Asp Ser Gly Arg Asp Tyr Val Ser Gln Phe Glu Gly Ser Ala Leu Gly
1               5                   10                  15

Lys

<210> SEQ ID NO 633
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Asp Tyr Val Ser Gln Phe Glu Gly Ser Ala Leu Gly Lys
1               5                   10

<210> SEQ ID NO 634
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Glu Gln Leu Gly Pro Val Thr Gln Glu Phe Trp Asp Asn Leu Glu Lys
1               5                   10                  15

<210> SEQ ID NO 635
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Glu Gln Leu Gly Pro Val Thr Gln Glu Phe Trp Asp Asn Leu Glu Lys
1               5                   10                  15

Glu Thr Glu Gly Leu Arg
            20

<210> SEQ ID NO 636
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Glu Gln Leu Gly Pro Val Thr Gln Glu Phe Trp Asp Asn Leu Glu Lys
1               5                   10                  15

Glu Thr Glu Gly Leu Arg Gln Glu Met Ser Lys
            20                  25

<210> SEQ ID NO 637
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 637

Lys Trp Gln Glu Glu Met Glu Leu Tyr Arg
1 5 10

<210> SEQ ID NO 638
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 638

Leu Glu Ala Leu Lys Glu Asn Gly Gly Ala Arg
1 5 10

<210> SEQ ID NO 639
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 639

Leu His Glu Leu Gln Glu Lys
1 5

<210> SEQ ID NO 640
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 640

Leu Leu Asp Asn Trp Asp Ser Val Thr Ser Thr Phe Ser Lys
1 5 10

<210> SEQ ID NO 641
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 641

Leu Arg Glu Gln Leu Gly Pro Val Thr Gln Glu Phe Trp Asp Asn Leu
1 5 10 15

Glu Lys

<210> SEQ ID NO 642
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 642

Leu Arg Glu Gln Leu Gly Pro Val Thr Gln Glu Phe Trp Asp Asn Leu
1 5 10 15

Glu Lys Glu Thr Glu Gly Leu Arg
            20

<210> SEQ ID NO 643
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Leu Ser Pro Leu Gly Glu Glu Met Arg
1               5

<210> SEQ ID NO 644
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Gln Gly Leu Leu Pro Val Leu Glu Ser Phe Lys
1               5                   10

<210> SEQ ID NO 645
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Gln Leu Asn Leu Lys Leu Leu Asp Asn Trp Asp Ser Val Thr Ser Thr
1               5                   10                  15

Phe Ser Lys

<210> SEQ ID NO 646
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Thr His Leu Ala Pro Tyr Ser Asp Glu Leu Arg
1               5                   10

<210> SEQ ID NO 647
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Val Glu Pro Leu Arg Ala Glu Leu Gln Glu Gly Ala Arg
1               5                   10

<210> SEQ ID NO 648
<211> LENGTH: 13
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 648

Val Lys Asp Leu Ala Thr Val Tyr Val Asp Val Leu Lys
1 5 10

<210> SEQ ID NO 649
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 649

Val Lys Asp Leu Ala Thr Val Tyr Val Asp Val Leu Lys Asp Ser Gly
1 5 10 15

Arg

<210> SEQ ID NO 650
<211> LENGTH: 30
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 650

Val Lys Asp Leu Ala Thr Val Tyr Val Asp Val Leu Lys Asp Ser Gly
1 5 10 15

Arg Asp Tyr Val Ser Gln Phe Glu Gly Ser Ala Leu Gly Lys
20 25 30

<210> SEQ ID NO 651
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 651

Val Gln Pro Tyr Leu Asp Asp Phe Gln Lys
1 5 10

<210> SEQ ID NO 652
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 652

Val Gln Pro Tyr Leu Asp Asp Phe Gln Lys Lys
1 5 10

<210> SEQ ID NO 653
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 653

Val Gln Pro Tyr Leu Asp Asp Phe Gln Lys Lys Trp Gln Glu Glu Met
1               5                   10                  15

Glu Leu Tyr Arg
            20

<210> SEQ ID NO 654
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Val Ser Phe Leu Ser Ala Leu Glu Glu Tyr Thr Lys
1               5                   10

<210> SEQ ID NO 655
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Val Ser Phe Leu Ser Ala Leu Glu Glu Tyr Thr Lys Lys
1               5                   10

<210> SEQ ID NO 656
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Trp Gln Glu Glu Met Glu Leu Tyr Arg
1               5

<210> SEQ ID NO 657
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Glu Pro Cys Val Glu Ser Leu Val Ser Gln Tyr Phe Gln Thr Val Thr
1               5                   10                  15

Asp Tyr Gly Lys
            20

<210> SEQ ID NO 658
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

```
Ser Lys Glu Gln Leu Thr Pro Leu Ile Lys
1               5                   10


<210> SEQ ID NO 659
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Ile Leu Leu Gln Gly Thr Pro Val Ala Gln Met Thr Glu Asp Ala Val
1               5                   10                  15

Asp Ala Glu Arg
            20


<210> SEQ ID NO 660
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Asp Ile Ala Pro Thr Leu Thr Leu Tyr Val Gly Lys
1               5                   10


<210> SEQ ID NO 661
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Gly Ser Phe Pro Trp Gln Ala Lys
1               5


<210> SEQ ID NO 662
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Ile Leu Gly Gly His Leu Asp Ala Lys
1               5


<210> SEQ ID NO 663
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Val Gly Tyr Val Ser Gly Trp Gly Arg
1               5


<210> SEQ ID NO 664
<211> LENGTH: 10
```

<212> TYPE: PRT
<213> ORGANISM: Artificial Sequence
<220> FEATURE:
<223> OTHER INFORMATION: Description of Artificial Sequence: Synthetic peptide

<400> SEQUENCE: 664

Val Thr Ser Ile Gln Asp Trp Val Gln Lys
1 5 10

<210> SEQ ID NO 665
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 665

Val Val Leu His Pro Asn Tyr Ser Gln Val Asp Ile Gly Leu Ile Lys
1 5 10 15

<210> SEQ ID NO 666
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 666

Ala Pro Asn His Ala Val Val Thr Arg
1 5

<210> SEQ ID NO 667
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 667

Cys Leu Lys Asp Gly Ala Gly Asp Val Ala Phe Val Lys
1 5 10

<210> SEQ ID NO 668
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 668

Glu Asp Pro Gln Thr Phe Tyr Tyr Ala Val Ala Val Val Lys
1 5 10

<210> SEQ ID NO 669
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 669

Ile Met Asn Gly Glu Ala Asp Ala Met Ser Leu Asp Gly Gly Phe Val

```
1               5                   10                  15

Tyr Ile Ala Gly Lys
            20


<210> SEQ ID NO 670
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Ser Lys Glu Phe Gln Leu Phe Ser Ser Pro His Gly Lys
1               5                   10


<210> SEQ ID NO 671
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Ser Met Gly Gly Lys Glu Asp Leu Ile Trp Glu Leu Leu Asn Gln Ala
1               5                   10                  15

Gln Glu His Phe Gly Lys
            20


<210> SEQ ID NO 672
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Thr Ala Gly Trp Asn Ile Pro Met Gly Leu Leu Tyr Asn Lys
1               5                   10


<210> SEQ ID NO 673
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Ala Leu Gly Ile Ser Pro Phe His Glu His Ala Glu Val Val Phe Thr
1               5                   10                  15

Ala Asn Asp Ser Gly Pro Arg
            20


<210> SEQ ID NO 674
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Arg Tyr Thr Ile Ala Ala Leu Leu Ser Pro Tyr Ser Tyr Ser Thr Thr
```

1 5 10 15

Ala Val Val Thr Asn Pro Lys Glu
20

<210> SEQ ID NO 675
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 675

Thr Ser Glu Ser Gly Glu Leu His Gly Leu Thr Thr Glu Glu Glu Phe
1 5 10 15

Val Glu Gly Ile Tyr Lys
20

<210> SEQ ID NO 676
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 676

Thr Ser Glu Ser Gly Glu Leu His Gly Leu Thr Thr Glu Glu Glu Phe
1 5 10 15

Val Glu Gly Ile Tyr Lys Val Glu Ile Asp Thr Lys
20 25

<210> SEQ ID NO 677
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 677

Tyr Thr Ile Ala Ala Leu Leu Ser Pro Tyr Ser Tyr Ser Thr Thr Ala
1 5 10 15

Val Val Thr Asn Pro Lys Glu
20

<210> SEQ ID NO 678
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 678

Val Phe Asp Glu Phe Lys Pro Leu Val Glu Glu Pro Gln Asn Leu Ile
1 5 10 15

Lys

<210> SEQ ID NO 679
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 679

Arg His Pro Tyr Phe Tyr Ala Pro Glu Leu Leu Phe Phe Ala Lys
1 5 10 15

<210> SEQ ID NO 680
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 680

Lys Val Pro Gln Val Ser Thr Pro Thr Leu Val Glu Val Ser Arg
1 5 10 15

<210> SEQ ID NO 681
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 681

Ala Val Met Asp Asp Phe Ala Ala Phe Val Glu Lys
1 5 10

<210> SEQ ID NO 682
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 682

Asp Thr Glu Glu Glu Asp Phe His Val Asp Gln Val Thr Thr Val Lys
1 5 10 15

<210> SEQ ID NO 683
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 683

Ile Thr Pro Asn Leu Ala Glu Phe Ala Phe Ser Leu Tyr Arg
1 5 10

<210> SEQ ID NO 684
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 684

Gly Thr Glu Ala Ala Gly Ala Met Phe Leu Glu Ala Ile Pro Met Ser
1 5 10 15

Ile Pro Pro Glu Val Lys
20

<210> SEQ ID NO 685
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 685

Thr Leu Asn Gln Pro Asp Ser Gln Leu Gln Leu Thr Thr Gly Asn Gly
1 5 10 15

Leu Phe Leu Ser Glu Gly Leu Lys
20

<210> SEQ ID NO 686
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 686

Val Phe Ser Asn Gly Ala Asp Leu Ser Gly Val Thr Glu Glu Ala Pro
1 5 10 15

Leu Lys

<210> SEQ ID NO 687
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 687

Gln Gly Leu Leu Pro Val Leu Glu Ser Phe Lys
1 5 10

<210> SEQ ID NO 688
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 688

Val Ser Phe Leu Ser Ala Leu Glu Glu Tyr Thr Lys
1 5 10

<210> SEQ ID NO 689
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 689

Asp Tyr Val Ser Gln Phe Glu Gly Ser Ala Leu Gly Lys
1 5 10

<210> SEQ ID NO 690
<211> LENGTH: 16

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 690

Glu Gln Leu Gly Pro Val Thr Gln Glu Phe Trp Asp Asn Leu Glu Lys
1 5 10 15

<210> SEQ ID NO 691
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 691

Leu Leu Asp Asn Trp Asp Ser Val Thr Ser Thr Phe Ser Lys
1 5 10

<210> SEQ ID NO 692
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 692

Glu Pro Cys Val Glu Ser Leu Val Ser Gln Tyr Phe Gln Thr Val Thr
1 5 10 15

Asp Tyr Gly Lys
20

<210> SEQ ID NO 693
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 693

Ser Lys Glu Gln Leu Thr Pro Leu Ile Lys
1 5 10

<210> SEQ ID NO 694
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 694

Ile Leu Leu Gln Gly Thr Pro Val Ala Gln Met Thr Glu Asp Ala Val
1 5 10 15

Asp Ala Glu Arg
20

<210> SEQ ID NO 695
<211> LENGTH: 9
<212> TYPE: PRT
<213> ORGANISM: Artificial Sequence
<220> FEATURE:

<223> OTHER INFORMATION: Description of Artificial Sequence: Synthetic peptide

<400> SEQUENCE: 695

Val Gly Tyr Val Ser Gly Trp Gly Arg
1 5

<210> SEQ ID NO 696
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 696

Val Val Leu His Pro Asn Tyr Ser Gln Val Asp Ile Gly Leu Ile Lys
1 5 10 15

<210> SEQ ID NO 697
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 697

Ser Met Gly Gly Lys Glu Asp Leu Ile Trp Glu Leu Leu Asn Gln Ala
1 5 10 15

Gln Glu His Phe Gly Lys
20

<210> SEQ ID NO 698
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 698

Glu Asp Pro Gln Thr Phe Tyr Tyr Ala Val Ala Val Val Lys
1 5 10

<210> SEQ ID NO 699
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 699

Ile Met Asn Gly Glu Ala Asp Ala Met Ser Leu Asp Gly Gly Phe Val
1 5 10 15

Tyr Ile Ala Gly Lys
20

<210> SEQ ID NO 700
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 700

Thr Ser Glu Ser Gly Glu Leu His Gly Leu Thr Thr Glu Glu Glu Phe
1 5 10 15

Val Glu Gly Ile Tyr Lys
20

<210> SEQ ID NO 701
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 701

Ala Leu Gly Ile Ser Pro Phe His Glu His Ala Glu Val Val Phe Thr
1 5 10 15

Ala Asn Asp Ser Gly Pro Arg
20

<210> SEQ ID NO 702
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 702

Thr Ser Glu Ser Gly Glu Leu His Gly Leu Thr Thr Glu Glu Glu Phe
1 5 10 15

Val Glu Gly Ile Tyr Lys Val Glu Ile Asp Thr Lys
20 25

<210> SEQ ID NO 703
<211> LENGTH: 6
<212> TYPE: PRT
<213> ORGANISM: Artificial Sequence
<220> FEATURE:
<223> OTHER INFORMATION: Description of Artificial Sequence: Synthetic 6x His tag

<400> SEQUENCE: 703

His His His His His His
1 5

<210> SEQ ID NO 704
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 704

Cys Ser Ile Ser Asp Ala Glu Gln Arg Gly Glu Asn Ala Leu Lys
1 5 10 15

<210> SEQ ID NO 705
<211> LENGTH: 11
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 705

```
Glu Leu Leu Gln Gln Val Asp Thr Ser Thr Arg
1               5                   10
```

PEPTIDE ANTIBODY DEPLETION AND ITS APPLICATION TO MASS SPECTROMETRY SAMPLE PREPARATION

CROSS-REFERENCE TO RELATED APPLICATIONS

This application is a continuation of U.S. patent application Ser. No. 12/307,510, filed Jan. 5, 2009, issued as U.S. Pat. No. 8,232,066 on Jul. 31, 2013, which is the U.S. national phase application pursuant to 35 U.S.C. §371 U.S. of PCT International Application PCT/US2007/015390, having an international filing date of Jul. 3, 2007, which claims the benefit of U.S. Provisional Application No. 60/818,363, filed Jul. 3, 2006, the contents of each of the aforementioned applications are herein incorporated by reference in their entireties.

FIELD OF THE INVENTION

The present invention relates, e.g., to a method to prepare samples for mass spectral analysis.

BACKGROUND INFORMATION

In mass spectrometry (MS), the ability to detect all analytes present in a sample depends on a number of parameters, including the complexity of the sample mixture. Ideally, the goal in any MS experiment is to detect 100% of the analytes present. However, as sample complexity increases, the ability to detect all species present markedly decreases. This is due to several factors, including: (1) ionization suppression (seen in MALDI (matrix-assisted laser desorption/ionization spectroscopy), (2) differences in ionization potential (seen in MALDI and ESI (electrospray ionization mass spectroscopy) and (3) the fact that higher abundance species can drown out the lower abundance species due to the limited dynamic range of common detectors (seen in MALDI and ESI). In MS, an analyte (e.g. peptide, protein, lipid, etc) must become ionized in the sample source region in order for it to reach the detector. The potential for any analyte to become ionized (ionization potential) is related to the sequence of the peptide (e.g. number of charged residues) as well as the presence of other components in the sample mixture, since other peptides may compete for ionization and contaminant adducts (e.g. Na, K) can adversely affect the ionization efficiency. These challenges are problematic in the field of proteomics, where any one sample may contain hundreds of proteins present in concentrations that span the dynamic range of $10^9$ orders of magnitude (i.e. $10^8$ log difference in abundance from the lowest abundance protein to the highest abundance protein). When these samples are subjected to enzymatic or chemical digestion, the resulting peptide mixtures are considerably more complicated than the original protein mixtures. Consequently, the presence of high abundance proteins in a proteomics mixture can present challenges for the detection of lesser abundant proteins due to resulting dynamic range issues and competition for ionization.

In addition to the adverse effects of high abundance peptides on the ionization efficiency and detection of other peptides, the presence of peptides from contaminating proteins in a proteomics study can affect the random match probability for peptide mass fingerprinting (PMF). In PMF, the peptide masses from an enzymatic or chemical digestion of the protein are compared to the masses from an in silico digest of protein in a database, for the purpose of protein identification. Consequently, when contaminant peptide masses (from keratin or trypsin, for example) are present, they may cause random matching of experimental masses to the theoretical masses in the database if they are combined with peptide analyte masses in a single search. Thus, the presence of peptides from both high abundance proteins and contaminant proteins can have an adverse affect on (1) the ability to obtain complete sequence coverage of the protein(s) of interest and (2) can interfere with the ability to correctly identify the analyte of interest.

In proteomics, two approaches are commonly used to overcome complications from high abundance proteins or interference from contaminant proteins. These include (1) removal of peptide masses attributed to contaminant/high abundance proteins from the peptide peak list prior to database searching, or alternatively, filtering out peptides attributed to the contaminant/high abundance proteins after the database search and (2) removal of high abundance proteins as a whole, by affinity depletion (or other) methods prior to enzymatic/chemical digestion. Unfortunately, the removal of peptide masses from the peak lists, either prior to or after database searching, does not address the fundamental issues of ionization suppression or saturation of the detector that occur during data acquisition. While this approach may simplify the database search and data analysis, it does not lead to an ability to actually detect any more peptides. Additionally, the removal of intact proteins prior to digestion is plagued by the problem that protein depletion methods can non-specifically remove other proteins in low abundance (or high abundance proteins if there are high affinity interactions). Therefore, the removal of intact higher abundance proteins is disadvantageous for studies that aim to identify as many proteins as possible in the original sample.

In diagnostic assays for proteins of interest, the primary limitation is the detection capabilities of the target of interest. The most sensitive assays currently in use are generally those employing Enzyme Linked Immuno-Sorbant Assay (ELISA), which uses an antibody to capture a target and then a secondary antibody coupled to an enzyme to allow for amplification of the detection signal. These assays typically allow for up to low picogram levels of detection.

DETAILED DESCRIPTION

Figure 1:
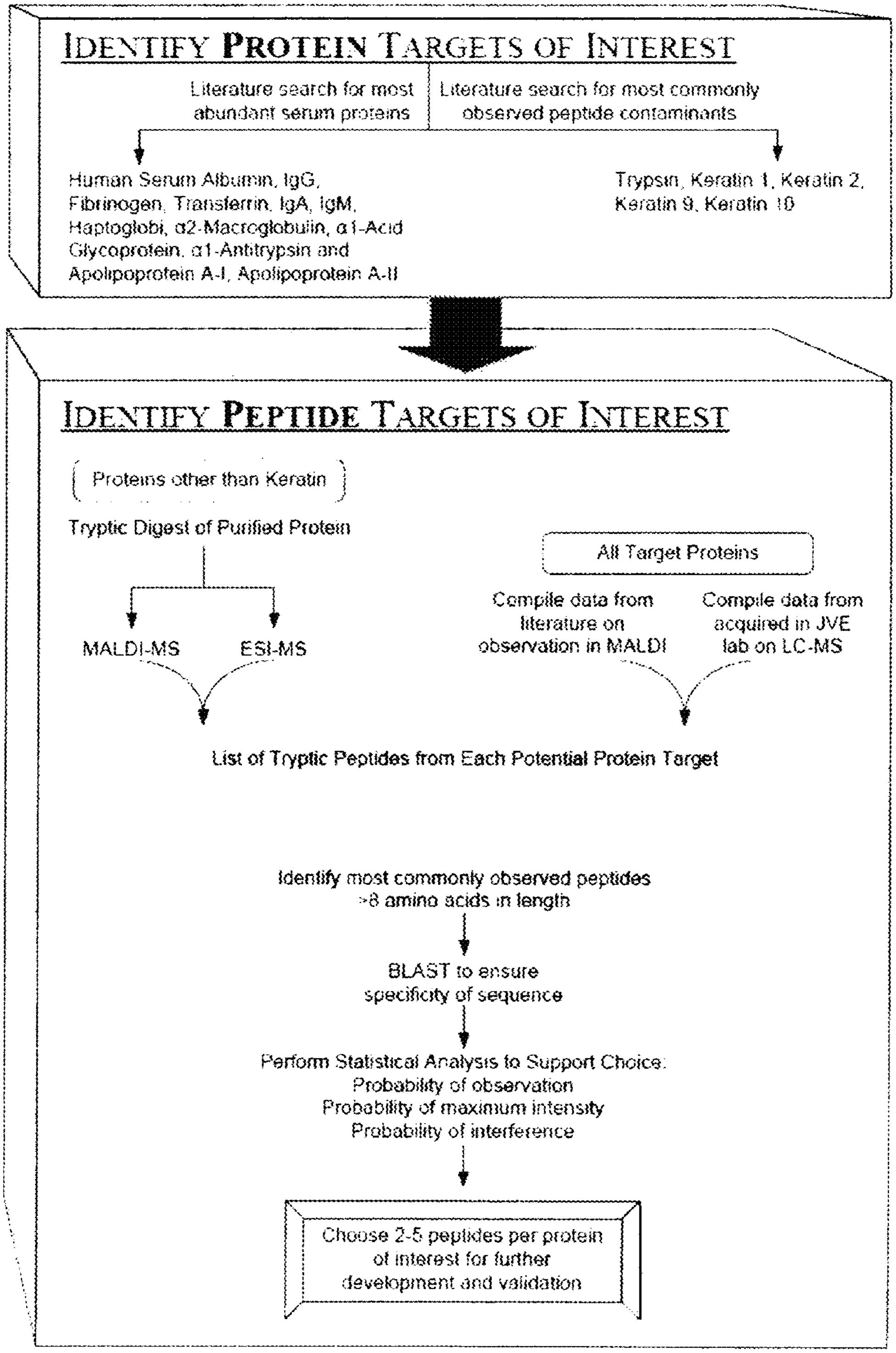
FIG. 1 shows diagrammatically Part II of the PAD development workflow.

The present inventors have recognized that an efficient, reproducible method for pre-processing protein-containing samples for mass spectral analysis (sometimes referred to herein as mass spec, mass spectrometry or mass spectroscopy) is to physically remove undesirable highly abundant and/or well-ionizing peptides from the samples before the analysis (data acquisition) is conducted. In one embodiment of the method, the peptides which are removed have been previously identified as being common contaminants in preparations for mass spec analysis. In another embodiment, peptides that are well-ionizing (either from highly abundant proteins, or from proteins that are lower in abundance, but wherein certain peptides are particularly well-ionizing and thus potentially problematic for MS analysis) are identified by a method as follows: one or more potentially contaminating proteins are cleaved to peptides with a protease or chemical method; the resulting peptides are subjected to MS; the peptides observed in the MS analysis are ranked in order with respect to ionization or ionizing potential (e.g., beginning with the most highly ionizing peptide); and, optionally, a suitable number of peptides (e.g. about 3-8 of the most well-ionized peptides for each protein) are selected, e.g. as targets for removal.

A variety of methods for physical removal of the highly abundant and/or well-ionizing peptides can be employed in a method of the invention. In one method, the peptides are immunodepleted from the sample to be analyzed. In such an embodiment, antibodies are generated against the peptides to be removed and, optionally, are attached to a surface (e.g. a chip, beads, pipette tips, etc.); the sample that is to be subjected to MS is contacted with the antibodies under conditions that are effective for the antibodies to bind to their cognate peptides; and the bound peptides are removed from the sample.

Advantages of this method include that, by removing peptides (e.g., well-ionizing peptides) derived from high abundance and/or common contaminating proteins, rather than by removing the full-length proteins, themselves, one can reduce or eliminate the removal of desirable peptides, such as peptides that are present in the sample in low amounts (low abundance peptides). Without wishing to be bound by any particular mechanism, it is suggested that, because protein: protein interactions are stabilized by secondary, tertiary and quaternary structure, by working at the peptide level, one can eliminate these higher order structures that could cause non-specific (or even specific) depletion of other proteins. Furthermore, by targeting peptides that are particularly well-ionizable, one can remove a source of many of the problems that limit MS analysis (e.g., ionization suppression and differences in ionization potential). By removing contaminating peptides from a sample destined for MS analysis, methods of the invention can impart a beneficial effect on the resulting spectrum, and can allow for efficient detection (coverage) of proteins/peptides, including of low abundance proteins/peptides. Such a method is particularly useful when analyzing peptide mixtures generated in proteomics analyses.

In another embodiment of the invention, antibodies are generated against highly ionizable peptides derived from a protein of interest (e.g. a protein from a pathogen of interest or a disease marker), by a method as described herein, but instead of using the antibodies to eliminate these peptides from a sample being processed for MS, the antibodies are used in order to isolate or concentrate the peptides and, subsequently, to detect the protein from which the highly ionized peptides were derived. For example, a sample suspected of containing a protein of interest (e.g., from a pathogen or disease marker) is cleaved to peptides and then contacted with one or more antibodies specific for highly ionizable peptides of the protein, under conditions that are effective to bind the highly ionizable peptides specifically to the antibodies, if the highly ionizable peptides are present in the mixture of cleaved proteins. Bound peptides are then separated from the mixture of peptides and are thus concentrated (enriched); and the concentrated peptides are eluted and analyzed by MS. The presence of the highly ionizable peptides in the readout indicates that the sample contained the protein of interest.

Advantages of such a detection method include, e.g., that, by focusing on the detection of highly ionizable peptides, one can attain a much higher sensitivity and specificity of detection by MS than by detecting less highly ionizable peptides. It is expected that the detection level will be essentially at the level of detection of the mass spectrometer (e.g. at the femtomolar level, or even at the attomolar level).

In addition to the methods discussed above, described herein are compositions comprising peptides of interest or antibodies specific for the peptides, and platforms (e.g., devices) comprising such compositions, bound to a solid surface (such as a bead, column, chip, etc.). Such compositions and devices can be used in methods of the invention. For example, such a device (sometimes referred to herein as a peptide antibody depletion device, or PAD) can be used to remove peptides from common protein contaminants, including proteins that are in high abundance in particular samples, such as serum proteins.

One aspect of the present invention is a method for preprocessing a sample for mass spectral analysis, comprising cleaving proteins in the sample to peptides and immunodepleting highly abundant and/or well-ionizing and/or proteotypic peptides from the sample.

The immunodepletion may be carried out, for example, by (a) contacting the peptides resulting from cleavage of the protein(s) with one or more antibodies that are specific for highly abundant and/or well-ionizing and/or proteotypic peptides in the sample, under conditions that are effective for the antibodies to bind specifically to their cognate peptides, and (b) removing the bound abundant and/or well-ionizing and/or proteotypic peptides from the sample.

Another aspect of the invention is a method for identifying highly ionizing peptides of a protein, comprising (a) cleaving the protein with a protease or a chemical method; (b) subjecting the resulting peptides to mass spectrometry; (c) ranking the peptides in order with respect to their ionization potential (e.g., beginning with the most highly ionizing peptides); and, optionally, (d) selecting about 3-8 of the most highly ionizing peptides from each protein.

As used herein, the singular forms “a,” “an,” and “the” include plural referents unless the context clearly dictates otherwise. For example, “a” protein, as used above, means one or more proteins, which can be the same or different.

In one embodiment of this method, the protein for which highly ionizing peptides are identified is a known or suspected contaminant, which can interfere with mass spectrophotometric analysis of a protein of interest in a sample. For example, this identification method allows an investigator to identify which (highly ionizable) peptides from a high abundant protein that is present in a sample (e.g., in serum) would be most valuable to remove. The identified, highly ionizable peptides can then be removed (e.g. by immunodepletion) from such a sample prior to MS analysis of a protein of interest.

In another embodiment of this method, the protein for which highly ionizing peptides are identified is found in a pathogen of interest or is produced by the pathogen. In this embodiment, a protein-containing sample from a subject that is suspected of being infected by the pathogen is treated to cleave proteins in the sample, and the resulting peptides are contacted with antibodies specific for the highly ionizable, pathogen-related, peptides. Highly ionizable peptides that are present in the sample are collected (concentrated, enriched), eluted, and subjected to MS. The presence of the highly ionizable peptides in the read-out (e.g., in a significantly increased amount compared to a baseline value, such as a comparable sample from a subject known not to be infected by the pathogen, or a suitable reference standard) indicates that the subject is infected with the pathogen. A similar analysis can be carried out to determine the presence of an organism, such as a pathogen, in a sample that is not from a subject (e.g., patient), such as an environmental sample.

In another embodiment of this method, the protein for which highly ionizing peptides are identified is a marker for a disease or disorder. In this embodiment, a sample from a subject suspected of having the disease or disorder is treated as above. The presence of the highly ionizable peptides in the MS read-out (e.g., in a significantly increased amount compared to a baseline value, such as a comparable sample from a subject known not to have the disease or disorder, or a suitable reference standard) indicates that the subject has or is likely to have the disease or disorder (is indicative of the presence of the disease or disorder). The predictive value of the individual peptides will vary according to the particular peptide and the disease or disorder, and should be able to be determined by those of skill in the art without undue experimentation.

Another aspect of the invention is a composition comprising one or more antibodies (e.g., polyclonal or monoclonal antibodies, active fragments of antibodies, such as Fab fragments, etc.) that are specific for one or more of the highly abundant and/or well-ionizing and/or proteotypic peptides of the invention. In one embodiment, the antibodies are attached (bound) to a surface, such as a bead, column material, pipette tip, etc. They may be arranged in an array, such as on a "chip." One aspect of the invention is a device comprising antibodies of the invention which are bound to a surface of the device. The device can be used, e.g., to pre-process samples for spectral analysis, or to collect and/or concentrate peptides to be analyzed by MS in a detection (e.g., diagnostic) assay.

Another aspect of the invention is a kit for performing one of the methods of the invention. The kit can comprise, e.g., a collection of antibodies that are specific for highly abundant and/or ionizable and/or proteotypic peptides and, optionally, packaging materials and/or instructions (e.g., written instructions) for use. The antibodies may be bound to a surface. A kit of the invention can be used, e.g., for pre-processing a sample for mass spectral analysis. In another embodiment, a kit of the invention can be used to isolate peptides, such as proteotypic peptides, e.g., for the detection of a protein of interest, such as a protein that is present in, or produced by, a pathogen, or a disease marker.

In one embodiment of the invention, proteins are identified whose presence in a sample is suspected of being detrimental during MS analysis of the sample. Representative peptides of those proteins are then identified for removal, e.g. by immunodepletion using antibodies that are specific for these peptides. The identification of these peptides as targets for antibody development is supported by conventional statistical analyses on the value of those targets and the predicted effect that their removal will have upon improvement in spectral quality. Upon identification of these peptide targets, antibodies for them are developed and purified, and solid-phase devices containing these antibodies are tested and validated for their ability to enhance the detection of lower abundance and other peptides in a complex mixture.

A method for identifying proteins (and peptides thereof) to be removed from a sample destined for MS analysis is illustrated herein for proteomics analysis of serum/plasma samples. Part I of the method—the identification of suitable protein targets for removal—is illustrated in the upper part of FIG. 1. Similar methods can be employed for samples from other tissue, organelle or cell sources, and for other types of analysis. Tables 5 and 2 shows representative lists of suitable protein (Table 5) and peptide (Table 2) targets for serum/plasma samples. These proteins have been identified through literature searches of the most abundant proteins in serum (Anderson et al. (2002) *Proteomics* 1, 845-867), and for commonly observed contaminant peaks (Ding et al. (2003)) in, e.g., MALDI and ESI MS. It is noted that multiple types or isoforms of keratin are included, as they are commonly observed in MS data.

Part II of the method—the identification of suitable peptides of the proteins identified in Part I of the method—is illustrated in the bottom portion of FIG. 1. Selected protein targets are cleaved by an enzymatic or chemical method. In this illustration, trypsin is used to digest the proteins. However, as discussed elsewhere herein, a variety of other enzymes or chemical methods can also be used. In this step, peptides are identified which, when removed from the peptide mixture, allow for the most beneficial improvement in the spectra, thereby resulting in enhanced detection of other peptides. Data from previously published reports, PRIDE database [EBI], and any database archiving peptide/protein data that includes peptide ionization potentials, can be employed, and can be combined with the number of observations of the peptides counted by the investigator, to create a database of potential peptide targets. The identification of peptide targets is initiated by pooling data obtained from both in vitro tryptic digestions of purified proteins, and the mining of database search results. The potential peptide target database preferably contains peptides that are amenable to antibody development (e.g. consisting of about 5-20, or more, amino acids, e.g., about 8-15 amino acids in length). Generally, an alignment search (e.g. a BLAST search) is performed to ensure that each peptide is specific to the protein, or class of proteins (e.g. all keratins, all immunoglobulins, etc.) that is targeted for removal. Following these filters, conventional bioinformatics and statistical analyses are employed to further define the peptide targets, to ensure specificity and maximum potential for spectral enhancement, etc. Such analyses include, e.g., assessment of the most commonly observed peptides, probability of observation, probability that the peptide will be observed at maximum (or near maximum) relative intensity, and probability that the peptide interferes with the ability to detect other peptides. In general, for each target protein, about 2-8 (e.g., about 3-5) peptides are identified that fit these criteria and are selected for further processing in Part III of the method.

Part III of the method (illustrated in the top portion of FIG. 2) comprises the development and purification (e.g. affinity purification) of antibodies (e.g., polyclonal antisera and/or monoclonal antibodies) that are specific for the selected target peptides. These antibodies are then coupled to a solid phase, such as a matrix, bead or other column material, which can then be used in spin-column, chromatography column, pipette tip, or other device format.

Figure 2:
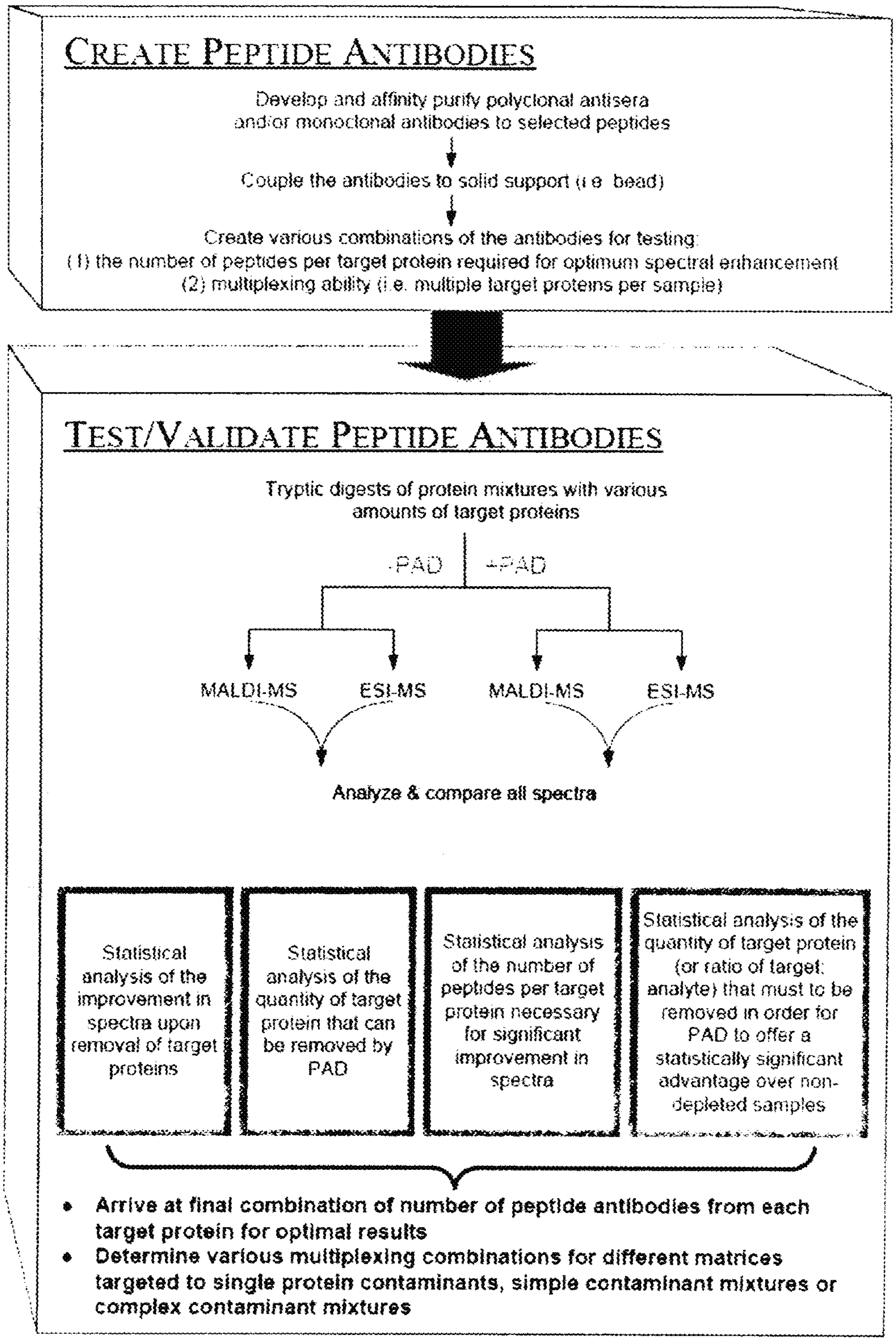
FIG. 2 shows diagrammatically Part III of the PAD development workflow.

Part IV of the method (PAD development workflow) is shown in the bottom portion of FIG. 2: the peptide antibodies and resulting device(s) are validated, using a number of different peptide mixtures. For both MALDI and ESI MS, the number and combination of peptide antibodies required for a statistically significant improvement in spectra and detection of low abundance and other peptides is evaluated. This evaluation includes a determination of the amount of high abundance/contaminant peptides that can be removed by PAD, the number of peptides per protein required for desired enhancement of spectra, and the amount of target peptides (or ratio of target to analyte) that must be removed for desired enhancement of spectra. In embodiments of the invention, a device so defined contains one or more (e.g. a mixture of) antibodies to peptides, so that multiple target peptides from multiple proteins can be removed with a single device. In other embodiments, the device contains one or more (e.g. multiple) antibodies to peptides for the removal of peptides from a single protein target.

Example I describes a procedure in which immunodepletion of samples with antibodies against keratins was shown to improve spectral quality during mass spectrometry of the samples.

Example II describes a procedure in which immunodepletion of about 25 peptides (about 1-5 peptides from each of about eight proteins) is shown to improve spectral quality during mass spectrometry of the samples.

A number of highly abundant proteins (sometimes referred to herein as "high abundant" or "high abundance" proteins) and/or common contaminating proteins, or peptides of those proteins, have been identified that are desirably removed from samples destined for mass spectrometry (sometimes referred to here in as mass spectroscopy or mass spectral analysis).

Among such high abundance proteins are the 14 serum/plasma proteins which have been targeted for removal by commercially available columns. These are listed in Table 5.

TABLE 5

Highly abundant serum/plasma proteins removed by the MARS (Agilent Technologies) and ProteomeLab IgY 12 (Beckman-Coulter) immunoaffinity columns.

| Protein | Removed by MARS | Removed by IgY 12 |
|---|---|---|
| Albumin | X | X |
| Alpha-1-acid glycoprotein | X | X |
| Alpha-1-antitrypsin | X | X |
| Alpha-2-macroglobulin | X | X |
| Apolipoprotein AI | X | X |
| Apolipoprotein AII | X | X |
| Complement C3 | X | |
| Fibrinogen | X | X |

TABLE 5-continued

Highly abundant serum/plasma proteins removed by the MARS (Agilent Technologies) and ProteomeLab IgY 12 (Beckman-Coulter) immunoaffinity columns.

| Protein | Removed by MARS | Removed by IgY 12 |
|---|---|---|
| Haptoglobin | X | X |
| IgA | X | X |
| IgG | X | X |
| IgM | X | X |
| Transferrin | X | X |
| Transthyretin | X | |

As indicated in the Table, 12 of these high abundance serum proteins are targeted by the commercially available column manufactured by Beckman-Coulter (ProteomeLab™ IgY-12), and all 14 of them by the column manufactured by Agilent (MARS column). Other abundant tissue or subproteome proteins whose removal can be beneficial for MS analysis include, e.g., actin isoforms, tropomyosin, and other cytoskeletal proteins, collagen and glycolytic proteins. Other potentially contaminating proteins include enzymes (e.g., proteases, such as trypsin or chymotrypsin) that have been used to digest the proteins in a sample to peptides.

In addition to these high abundance protein targets, several previously published studies on the observation of common contaminant peptide masses in PMF (peptide mass fingerprinting) data provide a useful database of common contaminant masses. For example, a report by Ding et al. (2003) *Proteomics* 3, 1313-1317 examined 3764 masses from 118 experimental PMF spectra and sorted out the 100 most frequently occurring contaminant masses. Table 2 lists 42 of these peptides, which are the most commonly observed peptides from keratins and typsin using MALDI-MS (as opposed to ESI-MS as used in Table 4).

TABLE 2

Interference probability, protein source, and peptide sequence of 42 commonly observed contaminant masses in MALD1 as compiled by Ding, et al. (2003, supra)

| Interference probability | Protein | Peptide Sequence |
|---|---|---|
| 85 | Trypsin | LGEHNIDVLEGNEQFINAAK (SEQ ID NO: 1) |
| 73 | Trypsin | IITHPNFNGNTLDNDIMLIK (SEQ ID NO: 2) |
| 64 | Trypsin | VATVSLPR (SEQ ID NO: 3) |
| 56 | Keratin 9 | GGGGSFGYSYGGGSGGGFSA SSLGGGFGGGSR (SEQ ID NO 4) |
| 47 | Keratin 10 | NVSTGDVNVEMNAAPGVDLT QLLNNMR (SEQ ID NO 5) |
| 43 | Keratin 10 | GSLGGGFSSGGFSGGSFSR (SEQ ID NO: 6) |
| 43 | Keratin 1 | LALDLEIATYR (SEQ ID NO: 7) |
| 42 | Keratin 1 | THNLEPYFESFINNLR (SEQ ID NO: 8) |
| 40 | Keratin 1 | YEELQITAGR (SEQ ID NO: 9) |
| 37 | Keratin 9 | MSCRQFSSSYLSRSGGGGGG GLGSGGSIR (SEQ ID NO: 10) |
| 36 | Keratin 1 | WELLQQVDTSTR (SEQ ID NO: 11) |
| 30 | Keratin 1 | GSYGSGGSSYGSGGGSYGSGGGGGGHGSYGSGSSSGGYR (SEQ ID NO: 12) |
| 29 | Keratin 10 | NQILNLITDNANILLQIDNA R (SEQ ID NO 13) |

TABLE 2-continued

Interference probability, protein source, and peptide sequence of 42 commonly observed contaminant masses in MALD1 as compiled by Ding, et al. (2003, supra)

| Interference probability | Protein | Peptide Sequence |
|---|---|---|
| 29 | Keratin 10 | SGGGGGGGGGCGGGGGVSSLR (SEQ ID NO 14) |
| 24 | Keratin 9 | FEMEQNLR (SEQ ID NO 15) |
| 20 | Keratin 1 | NMQDMVEDYR (SEQ ID NO: 16) |
| 20 | Keratin 10 | SQYEQLAEQNR (SEQ ID NO: 17) |
| 19 | Keratin 1 | IEISELNR (SEQ ID NO: 18) |
| 19 | Keratin 1 | QISNLQQSISDAEQR (SEQ ID NO: 19) |
| 19 | Keratin 9 | SDLEMQYETLQEELMALKK (SEQ ID NO: 20) |
| 16 | Keratin 10 | LENEIQTYR (SEQ ID NO: 21) |
| 15 | Keratin 9 | GGSGGSYGGGGSGGGYGGGS GSR (SEQ ID NO: 22) |
| 12 | Keratin 1 | GGGGGGYGSGGSSYGSGGGSYGSGGGGGGGR (SEQ ID NO 23) |
| 12 | Keratin 1 | SGGGFSSGSAGIINYQR (SEQ ID NO 24) |
| 10 | Trypsin | NKPGVYTK (SEQ ID NO: 25) |
| 10 | Keratin 1 | SLNNQFASFIDK (SEQ ID NO: 26) |
| 9 | Keratin 10 | AETECQNTEYQQLLDIK (SEQ ID NO: 27) |
| 9 | Keratin 10 | VTMQNLNDR (SEQ ID NO 28) |
| 8 | Keratin 10 | HGNSHQGEPR (SEQ ID NO: 29) |
| 8 | Keratin 9 | HGVQELEIELQSQLSK (SEQ ID NO: 30) |
| 8 | Keratin 10 | NVQALEIELQSQLALK (SEQ ID NO: 31) |
| 8 | Keratin 10 | SLLEGEGSSGGGGR (SEQ ID NO 32) |
| 6 | Keratin 9 | QEIECQNQEYSLLLSIK (SEQ ID NO: 33) |
| 4 | Keratin 1 | FSSCGGGGGSFGAGGGFGSR (SEQ ID NO: 34) |
| 4 | Keratin 9 | NYSPYYNTIDDLK (SEQ ID NO: 35) |
| 4 | Keratin 1 | SEIDNVK (SEQ ID NO: 36) |
| 4 | Keratin 1 | SISISVAR (SEQ ID NO: 37) |
| 4 | Keratin 1 | TLLEGEESR (SEQ ID NO: 38) |
| 3 | Keratin 9 | GPAAIQK (SEQ ID NO: 39) |
| 3 | Keratin 10 | LAADDFR (SEQ ID NO: 40) |
| 3 | Keratin 1 | MSGECAPNVSVSVSTSHTTI SGGGSR (SEQ ID NO: 41) |
| 3 | Keratin 9 | MTLDDFR (SEQ ID NO: 42) |

As can be seen from this Table, trypsin and several keratins are the source of the most commonly observed contaminant masses from these spectra. Consistent with the observation of Ding et al. (2003, supra), Schmidt et al. (2003) *J Am Soc Mass Spectrum* 14, 943-956 also reports that peptides from keratins and trypsin were observed in >5% of 480 PMF spectra. Furthermore, a similar report by Parker et al. (1998) *Electrophoresis* 19, 1920-1032 also lists keratins and trypsin as common contaminant peaks. See also Zolotarjova et al. (2005) *Proteomics* 5, 3304-3313, for a review of the proteins targeted for removal by commercially available methods.

Potentially contaminating peptides of some of the most abundant proteins in human serum/plasma are listed in Table 3. This table lists the predicted peptides following an in silico tryptic digest of 11 of the 14 most abundant proteins in human serum/plasma (listed in table 5). This table is not meant to be all inclusive of all of the potential peptides that could be observed, as sometimes trypsin may miss a site and thus lead to 'missed cleaveage'. Thus, this table provides an example of the types of data one would expect to observe after a tryptic digest of these proteins in serum/plasma. The list of proteins is independent of the type of mass spectrometer that is being used to acquire the data.

TABLE 3

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 2917.32 | SHCIAEVENDEMPADLPSLA ADFVESK | Albumin |
| 2593.24 | LVRPEVDVMCTAFHDNEETF LK | Albumin |
| 2433.26 | ALVLIAFAQYLQQCPFEDHV K | Albumin |
| 2404.17 | MPCAEDYLSVVLNQLCVLHE K | Albumin |
| 2203.00 | EFNAETFTFHADICTLSEK | Albumin |
| 2045.10 | VFDEFKPLVEEPQNLIK | Albumin |
| 1915.77 | VHTECCHGDLLECADDR | Albumin |
| 1853.91 | RPCFSALEVDETYVPK | Albumin |
| 1742.89 | HPYFYAPELLFFAK | Albumin |
| 1623.79 | DVFLGMFLYEYAR | Albumin |
| 1600.73 | QNCELFEQLGEYK | Albumin |
| 1511.84 | VPQVSTPTLVEVSR | Albumin |
| 1386.62 | YICENQDSISSK | Albumin |
| 1384.54 | TCVADESAENCDK | Albumin |
| 1381.53 | CCAAADPHECYAK | Albumin |
| 1342.63 | AVMDDFAAFVEK | Albumin |
| 1320.49 | ETYGEMADCCAK | Albumin |
| 1311.74 | HPDYSVVLLLR | Albumin |
| 1257.52 | AAFTECCQAADK | Albumin |
| 1191.57 | ECCEKPLLEK | Albumin |
| 1149.62 | LVNEVTEFAK | Albumin |
| 1024.46 | CCTESLVNR | Albumin |
| 1018.48 | NECFLQHK | Albumin |
| 1017.54 | SLHTLFGDK | Albumin |
| 1013.60 | LVAASQAALGL | Albumin |
| 1013.42 | ETCFAEEGK | Albumin |
| 1000.60 | QTALVELVK | Albumin |
| 984.49 | TYETTLEK | Albumin |
| 960.56 | FQNALLVR | Albumin |
| 951.44 | DLGEENFK | Albumin |
| 940.45 | DDNPNLPR | Albumin |
| 927.49 | YLYEIAR | Albumin |
| 880.44 | AEFAEVSK | Albumin |
| 876.50 | LCTVATLR | Albumin |
| 789.47 | LVTDLTK | Albumin |
| 715.42 | AACLLPK | Albumin |
| 698.36 | SEVAHR | Albumin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 695.34 | NYAEAK | Albumin |
| 674.35 | TPVSDR | Albumin |
| 673.38 | AWAVAR | Albumin |
| 658.32 | QEPER | Albumin |
| 2519.39 | QIPLCANLVPVPITNATLDQ ITGK | Alpha-1-acid glycoprotein |
| 1919.95 | SVQEIQATFFYFTPNK | Alpha-1-acid glycoprotein |
| 1858.88 | QDQCIYNTTYLNVQR | Alpha-1-acid glycoprotein |
| 1752.95 | YVGGQEHFAHLLILR | Alpha-1-acid glycoprotein |
| 1708.85 | NWGLSVYADKPETTK | Alpha-1-acid glycoprotein |
| 1685.78 | EQLGEFYEALDCLR | Alpha-1-acid glycoprotein |
| 1445.66 | TYMLAFDVNDEK | Alpha-1-acid glycoprotein |
| 1160.59 | WFYIASAFR | Alpha-1-acid glycoprotein |
| 1112.53 | SDVVYTDWK | Alpha-1-acid glycoprotein |
| 994.52 | TEDTIFLR | Alpha-1-acid glycoprotein |
| 796.35 | NEEYNK | Alpha-1-acid glycoprotein |
| 776.39 | ENGTISR | Alpha-1-acid glycoprotein |
| 718.34 | CEPLEK | Alpha-1-acid glycoprotein |
| 696.33 | EYQTR | Alpha-1-acid glycoprotein |
| 678.26 | QEEGES | Alpha-1-acid glycoprotein |
| 3691.82 | ADTHDEILEGLNFNLTEIPE AQIHEGFQELLR | Alpha-1-antitrypsin |
| 3161.64 | QLAHQSNSTNIFFSPVSIAT AFAMLSLGTK | Alpha-1-antitrypsin |
| 2574.34 | TLNQPDSQLQLTTGNGLFLS EGLK | Alpha-1-antitrypsin |
| 2259.14 | GTEAAGAMFLEAIPMSIPPE VK | Alpha-1-antitrypsin |
| 2057.95 | LYHSEAFTVNFGDTEEAK | Alpha-1-antitrypsin |
| 1891.86 | DTEEEDFHVDQVTTVK | Alpha-1-antitrypsin |
| 1855.98 | FNKPFVFLMIEQNTK | Alpha-1-antitrypsin |
| 1833.92 | VFSNGADLSGVTEEAPLK | Alpha-1-antitrypsin |
| 1803.96 | LQHLENELTHDIITK | Alpha-1-antitrypsin |
| 1779.77 | TDTSHHDQDHPTFNK | Alpha-1-antitrypsin |
| 1755.90 | YLGNATAIFFLPDEGK | Alpha-1-antitrypsin |
| 1641.86 | ITPNLAEFAFSLYR | Alpha-1-antitrypsin |
| 1576.84 | DTVFALVNYIFFK | Alpha-1-antitrypsin |
| 1190.58 | LGMFNIQHCK | Alpha-1-antitrypsin |
| 1110.60 | LSITGTYDLK | Alpha-1-antitrypsin |
| 1090.57 | WERPFEVK | Alpha-1-antitrypsin |
| 1076.62 | LSSVVVLLMK | Alpha-1-antitrypsin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 1058.47 | EDPQGDAAQK | Alpha-1-antitrypsin |
| 1015.61 | SVLGQLGITK | Alpha-1-antitrypsin |
| 1008.50 | QINDYVEK | Alpha-1-antitrypsin |
| 922.43 | FLENEDR | Alpha-1-antitrypsin |
| 888.50 | AVLTIDEK | Alpha-1-antitrypsin |
| 852.49 | SASLHLPK | Alpha-1-antitrypsin |
| 785.45 | VVNPTQK | Alpha-1-antitrypsin |
| 779.41 | SPLFMGK | Alpha-1-antitrypsin |
| 750.40 | FLEDVK | Alpha-1-antitrypsin |
| 686.44 | IVDLVK | Alpha-1-antitrypsin |
| 3827.94 | SFVHLEPMSHELPCGHTQTV QAHYILNGGTLLGLK | Alpha-2-macroglobulin |
| 3804.78 | GNEANYYSNATTDEHGLVQF SINTTNVMGTSLTVR | Alpha-2-macroglobulin |
| 3720.88 | YFPETWIWDLVVVNSAGVAE VGVTVPDTITEWK | Alpha-2-macroglobulin |
| 3620.85 | IITILEEEMNVSVCGLYTYG KPVPGHVTVSICR | Alpha-2-macroglobulin |
| 3356.61 | SLGNVNFTVSAEALESQELC GTEVPSVPEHGR | Alpha-2-macroglobulin |
| 3281.46 | SPCYGYQWVSEEHEEAHHTA YLVFSPSK | Alpha-2-macroglobulin |
| 3205.77 | GGVEDEVTLSAYITIALLEI PLTVTHPWR | Alpha-2-macroglobulin |
| 2917.52 | AVDQSVLLMKPDAELSASSV YNLLPEK | Alpha-2-macroglobulin |
| 2810.44 | VVSMDENFHPLNELIPLVYI QDPK | Alpha-2-macroglobulin |
| 2544.34 | SVSGKPQYMVLVPSLLHTET TEK | Alpha-2-macroglobulin |
| 2491.06 | VYDYYETDEFAIAEYNAPCS K | Alpha-2-macroglobulin |
| 2418.20 | SLFTDLEAENDVLHCVAFAV PK | Alpha-2-macroglobulin |
| 2388.27 | AYIFIDEAHITQALIWLSQR | Alpha-2-macroglobulin |
| 2387.19 | QQNAQGGESSTQDTVVALHA LSK | Alpha-2-macroglobulin |
| 2340.21 | GCVLLSYLNETVTVSASLES VR | Alpha-2-macroglobulin |
| 2340.13 | ETTENSLLCPSGGEVSEELS LK | Alpha-2-macroglobulin |
| 2249.08 | EEFPFALGVQTLPQTCDEPK | Alpha-2-macroglobulin |
| 2233.97 | DLTGFPGPLNDQDDEDCINR | Alpha-2-macroglobulin |
| 2163.18 | VSNQTLSLFFTVLQDVPVR | Alpha-2-macroglobulin |
| 2137.06 | HNVYINGITYTPVSSTNEK | Alpha-2-macroglobulin |
| 2110.08 | LHTEAQIQEEGTVVELTGR | Alpha-2-macroglobulin |
| 2049.05 | VDLSFSPSQSLPASHAHLR | Alpha-2-macroglobulin |
| 2045.10 | LLLQQVSLPELPGEYSMK | Alpha-2-macroglobulin |
| 2045.06 | AFQPFFVELTMPYSVIR | Alpha-2-macroglobulin |
| 2025.99 | AGAFCLSEDAGLGISSTASL R | Alpha-2-macroglobulin |
| 2016.91 | MCPQLQQYEMHGPEGLR | Alpha-2-macroglobulin |
| 1991.74 | YSDASDCHGEDSQAFCEK | Alpha-2-macroglobulin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 1884.05 | VSVQLEASPAFLAVPVEK | Alpha-2-macroglobulin |
| 1848.88 | QFSFPLSSEPFQGSYK | Alpha-2-macroglobulin |
| 1845.04 | LLIYAVLPTGDVIGDSAK | Alpha-2-macroglobulin |
| 1842.86 | FSGQLNSHGCFYQQVK | Alpha-2-macroglobulin |
| 1840.92 | AHTSFQISLSVSYTGSR | Alpha-2-macroglobulin |
| 1780.01 | DTVIKPLLVEPEGLEK | Alpha-2-macroglobulin |
| 1697.84 | SSSNEEVMFLTVQVK | Alpha-2-macroglobulin |
| 1672.86 | TEHPFTVEEFVLPK | Alpha-2-macroglobulin |
| 1620.82 | DNSVHWERPQKPK | Alpha-2-macroglobulin |
| 1617.85 | TEVSSNHVLIYLDK | Alpha-2-macroglobulin |
| 1604.84 | IAQWQSFQLEGGLK | Alpha-2-macroglobulin |
| 1565.83 | ALLAYAFALAGNQDK | Alpha-2-macroglobulin |
| 1545.80 | LVHVEEPHTETVR | Alpha-2-macroglobulin |
| 1529.70 | TAQEGDHGSHVYTK | Alpha-2-macroglobulin |
| 1511.77 | AAQVTIQSSGTFSSK | Alpha-2-macroglobulin |
| 1497.76 | VTGEGCVYLQTSLK | Alpha-2-macroglobulin |
| 1491.80 | NQGNTWLTAFVLK | Alpha-2-macroglobulin |
| 1448.64 | DMYSFLEDMGLK | Alpha-2-macroglobulin |
| 1418.60 | HYDGSYSTFGER | Alpha-2-macroglobulin |
| 1416.83 | MVSGFIPLKPTVK | Alpha-2-macroglobulin |
| 1394.68 | NEDSLVFVQTDK | Alpha-2-macroglobulin |
| 1298.57 | EQAPHCICANGR | Alpha-2-macroglobulin |
| 1281.63 | NALFCLESAWK | Alpha-2-macroglobulin |
| 1259.57 | VGFYESDVMGR | Alpha-2-macroglobulin |
| 1255.64 | AIGYLNTGYQR | Alpha-2-macroglobulin |
| 1248.67 | LSFYYLIMAK | Alpha-2-macroglobulin |
| 1215.65 | VTAAPQSVCALR | Alpha-2-macroglobulin |
| 1210.64 | LPPNVVEESAR | Alpha-2-macroglobulin |
| 1168.53 | YDVENCLANK | Alpha-2-macroglobulin |
| 1148.62 | QGIPFFGQVR | Alpha-2-macroglobulin |
| 1134.58 | SASNMAIVDVK | Alpha-2-macroglobulin |
| 1120.64 | SIYKPGQTVK | Alpha-2-macroglobulin |
| 1116.60 | QTVSWAVTPK | Alpha-2-macroglobulin |
| 1103.61 | SSGSLLNNAIK | Alpha-2-macroglobulin |
| 1084.61 | GHFSISIPVK | Alpha-2-macroglobulin |
| 1046.59 | FEVQVTVPK | Alpha-2-macroglobulin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 1018.59 | ATVLNYLPK | Alpha-2-macroglobulin |
| 1006.47 | FQVDNNNR | Alpha-2-macroglobulin |
| 925.55 | TGTHGLLVK | Alpha-2-macroglobulin |
| 889.46 | SLNEEAVK | Alpha-2-macroglobulin |
| 886.44 | YGAATFTR | Alpha-2-macroglobulin |
| 883.56 | DLKPAIVK | Alpha-2-macroglobulin |
| 876.48 | YNILPEK | Alpha-2-macroglobulin |
| 828.46 | SDIAPVAR | Alpha-2-macroglobulin |
| 820.42 | QSSEITR | Alpha-2-macroglobulin |
| 806.40 | GPTQEFK | Alpha-2-macroglobulin |
| 765.41 | GEAFTLK | Alpha-2-macroglobulin |
| 760.37 | VDSHFR | Alpha-2-macroglobulin |
| 724.44 | GVPIPNK | Alpha-2-macroglobulin |
| 711.29 | DNGCFR | Alpha-2-macroglobulin |
| 699.35 | SNHVSR | Alpha-2-macroglobulin |
| 699.30 | EYEMK | Alpha-2-macroglobulin |
| 693.37 | TFAQAR | Alpha-2-macroglobulin |
| 678.39 | TTVMVK | Alpha-2-macroglobulin |
| 667.34 | AFTNSK | Alpha-2-macroglobulin |
| 665.36 | QLNYK | Alpha-2-macroglobulin |
| 650.28 | QEDMK | Alpha-2-macroglobulin |
| 1932.93 | EQLGPVTQEFWDNLEK | Apolipoprotein Al |
| 1612.79 | LLDNWDSVTSTFSK | Apolipoprotein Al |
| 1400.67 | DYVSQFEGSALGK | Apolipoprotein Al |
| 1386.72 | VSFLSALEEYTK | Apolipoprotein Al |
| 1301.65 | THLAPYSDELR | Apolipoprotein Al |
| 1283.57 | WQEEMELYR | Apolipoprotein AI |
| 1252.62 | VQPYLDDFQK | Apolipoprotein Al |
| 1235.69 | DLATVYVDVLK | Apolipoprotein Al |
| 1230.71 | QGLLPVLESFK | Apolipoprotein Al |
| 1226.54 | DEPPQSPWDR | Apolipoprotein Al |
| 1215.62 | ATEHLSTLSEK | Apolipoprotein Al |
| 1031.52 | LSPLGEEMR | Apolipoprotein AI |
| 1012.58 | AKPALEDLR | Apolipoprotein Al |
| 896.48 | LHELQEK | Apolipoprotein Al |
| 873.44 | AELQEGAR | Apolipoprotein Al |
| 831.44 | LAEYHAK | Apolipoprotein Al |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 781.43 | AHVDALR | Apolipoprotein A1 |
| 732.38 | DLEEVK | Apolipoprotein A1 |
| 704.36 | ETEGLR | Apolipoprotein A1 |
| 2385.20 | AGTELVNFLSYFVELGTQPA TQ | Apolipoprotein All |
| 2293.07 | EPCVESLVSQYFQTVTDYGK | Apolipoprotein All |
| 972.50 | SPELQAEAK | Apolipoprotein All |
| 941.57 | EQLTPLIK | Apolipoprotein All |
| 673.32 | SYFEK | Apolipoprotein All |
| 3926.88 | HLIVTPSGCGEQNMIGMTPT VIAVHYLDETEQWEK | Complement C3 |
| 3282.65 | QDSLSSQNQLGVLPLSWDIP ELVNMGQWK | Complement C3 |
| 3250.56 | LESEETMVLEAHDAQGDVPV TVTVHDFPGK | Complement C3 |
| 2841.41 | HYLMWGLSSDFWGEKPNLSY IIGK | Complement C3 |
| 2788.24 | GDQDATMSILDISMMTGFAP DTDDLK | Complement C3 |
| 2749.32 | YFKPGMPFDLMVFVTNPDGS PAYR | Complement C3 |
| 2679.25 | YYGGGYGSTQATFMVFQALA QYQK | Complement C3 |
| 2578.31 | TMQALPYSTVGNSNNYLHLS VLR | Complement C3 |
| 2564.29 | QKPDGVFQEDAPVIHQEMIG GLR | Complement C3 |
| 2546.00 | DTWVEHVVPEEDECQDEENQK | Complement C3 |
| 2494.15 | DYAGVFSDAGLTFTSSSGQQ TAQR | Complement C3 |
| 2444.31 | EPGQDLVVLPLSITTDFIPS FR | Complement C3 |
| 2415.17 | GICVADPFEVTVMQDFFIDL R | Complement C3 |
| 2263.14 | SLYVSATVILHSGSDMVQAE R | Complement C3 |
| 2257.11 | VQLSNDFDEYIMAIEQTIK | Complement C3 |
| 2255.16 | TVLTPATNHMGNVTFTIPAN R | Complement C3 |
| 2214.00 | EDIPPADLSDQVPDTESETR | Complement C3 |
| 2198.13 | VPVAVQGEDTVQSLTQGDGV AK | Complement C3 |
| 2166.00 | AYYENSPQQVFSTEFEVK | Complement C3 |
| 2160.21 | VFSLAVNLIAIDSQVLCGAV K | Complement C3 |
| 2157.09 | ILLQGTPVAQMTEDAVDAER | Complement C3 |
| 2151.21 | QLYNVEATSYALLALLQLK | Complement C3 |
| 2147.07 | DAPDHQELNLDVSLQLPSR | Complement C3 |
| 2045.88 | QCQDLGAFTESMVVFGCPN | Complement C3 |
| 1910.06 | VVLVSLQSGYLFIQTDK | Complement C3 |
| 1891.08 | LSINTHPSQKPLSITVR | Complement C3 |
| 1878.97 | EYVLPSFEVIVEPTEK | Complement C3 |
| 1878.89 | SEFPESWLWNVEDLK | Complement C3 |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 1872.03 | TELRPGETLNVNFLLR | Complement C3 |
| 1865.94 | VEGTAFVIFGIQDGEQR | Complement C3 |
| 1841.99 | VHQYFNVELIQPGAVK | Complement C3 |
| 1816.89 | SNLDEDIIAEENIVSR | Complement C3 |
| 1795.88 | DSITTWEILAVSMSDK | Complement C3 |
| 1787.97 | SGIPIVTSPYQIHFTK | Complement C3 |
| 1749.95 | DMALTAFVLISLQEAK | Complement C3 |
| 1743.91 | VELLHNPAFCSLATTK | Complement C3 |
| 1732.84 | DICEEQVNSLPGSITK | Complement C3 |
| 1671.85 | SYTVAIAGYALAQMGR | Complement C3 |
| 1653.88 | FVTVQATFGTQVVEK | Complement C3 |
| 1641.77 | AGDFLEANYMNLQR | Complement C3 |
| 1639.87 | TVMVNIENPEGIPVK | Complement C3 |
| 1610.72 | VYAYYNLEESCTR | Complement C3 |
| 1588.75 | VFLDCCNYITELR | Complement C3 |
| 1511.82 | LVAYYTLIGASGQR | Complement C3 |
| 1504.82 | SPMYSIITPNILR | Complement C3 |
| 1491.76 | GQGTLSVVTMYHAK | Complement C3 |
| 1471.74 | AAVYHHFISDGVR | Complement C3 |
| 1470.78 | IPIEDGSGEVVLSR | Complement C3 |
| 1401.84 | SSLSVPYVIVPLK | Complement C3 |
| 1370.73 | TIYTPGSTVLYR | Complement C3 |
| 1350.60 | VSHSEDDCLAFK | Complement C3 |
| 1345.70 | EVVADSVWVDVK | Complement C3 |
| 1335.73 | APSTWLTAYVVK | Complement C3 |
| 1289.61 | SGSDEVQVGQQR | Complement C3 |
| 1281.60 | ENEGFTVTAEGK | Complement C3 |
| 1261.60 | QELSEAEQATR | Complement C3 |
| 1243.57 | ACEPGVDYVYK | Complement C3 |
| 1226.66 | QPVPGQQMTLK | Complement C3 |
| 1212.68 | VTIKPAPETEK | Complement C3 |
| 1211.65 | IHWESASLLR | Complement C3 |
| 1208.60 | YYTYLIMNK | Complement C3 |
| 1193.60 | NTMILEICTR | Complement C3 |
| 1190.62 | DFDFVPPVVR | Complement C3 |
| 1184.51 | CAEENCFIQK | Complement C3 |
| 1183.59 | AELQCPQPAAR | Complement C3 |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 1152.60 | QPSSAFAAFVK | Complement C3 |
| 1148.64 | HQQTVTIPPK | Complement C3 |
| 1139.54 | FYYIYNEK | Complement C3 |
| 1110.63 | VLLDGVQNPR | Complement C3 |
| 1092.63 | NTLIIYLDK | Complement C3 |
| 1083.56 | GYTQQLAFR | Complement C3 |
| 1006.52 | DSCVGSLVVK | Complement C3 |
| 1005.47 | ADIGCTPGSGK | Complement C3 |
| 1002.55 | TGLQEVEVK | Complement C3 |
| 967.49 | FISLGEACK | Complement C3 |
| 959.55 | GLEVTITAR | Complement C3 |
| 898.48 | AVLYNYR | Complement C3 |
| 888.48 | IWDVVEK | Complement C3 |
| 887.46 | NEQVEIR | Complement C3 |
| 886.52 | ISLPESLK | Complement C3 |
| 878.52 | LMNIFLK | Complement C3 |
| 872.46 | QLANGVDR | Complement C3 |
| 871.52 | QGALELIK | Complement C3 |
| 858.48 | IFTVNHK | Complement C3 |
| 854.41 | IEGDHGAR | Complement C3 |
| 845.43 | WLNEQR | Complement C3 |
| 842.53 | VVLVAVDK | Complement C3 |
| 833.49 | LPYSVVR | Complement C3 |
| 824.47 | ASHLGLAR | Complement C3 |
| 821.38 | DQLTCNK | Complement C3 |
| 820.40 | FYHPEK | Complement C3 |
| 813.27 | CCEDGMR | Complement C3 |
| 805.48 | TFISPIK | Complement C3 |
| 804.45 | SVQLTEK | Complement C3 |
| 801.49 | WLILEK | Complement C3 |
| 778.33 | SGQSEDR | Complement C3 |
| 776.47 | GVFVLNK | Complement C3 |
| 775.46 | LVLSSEK | Complement C3 |
| 769.46 | VVPEGIR | Complement C3 |
| 759.40 | QNQELK | Complement C3 |
| 746.40 | VTLEER | Complement C3 |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 731.39 | AEDLVGK | Complement C3 |
| 731.34 | WEDPGK | Complement C3 |
| 730.37 | TLDPER | Complement C3 |
| 714.39 | RPQDAK | Complement C3 |
| 680.40 | FLTTAK | Complement C3 |
| 667.33 | YELDK | Complement C3 |
| 654.43 | LLPVGR | Complement C3 |
| 3071.38 | EVVTSEDGSDCPEAMDLGTL SGIGTLDGFR | Fibrinogen |
| 2967.39 | GEGSLNDEGEGEFWLGNDYL HLLTQR | Fibrinogen |
| 2456.23 | IFSVYCDQETSLGGWLLIQQ R | Fibrinogen |
| 2275.07 | DCDDVLQTHPSGTQSGIFNI K | Fibrinogen |
| 2265.05 | TFPGFFSPMLGEFVSETESR | Fibrinogen |
| 2198.98 | VELEDWAGNEAYAEYHFR | Fibrinogen |
| 2009.97 | NNSPYEIENGVVWVSFR | Fibrinogen |
| 1963.85 | NPSSAGSWNSGSSGPGSTGN R | Fibrinogen |
| 1906.72 | DSDWPFCSDEDWNYK | Fibrinogen |
| 1872.77 | MADEAGSEADHEGTHSTK | Fibrinogen |
| 1637.77 | ESSSHHPGIAEFPSR | Fibrinogen |
| 1629.83 | DSHSLTTNIMEILR | Fibrinogen |
| 1593.72 | HPDEAAFFDTASTGK | Fibrinogen |
| 1572.68 | GGSTSYGTGSETESPR | Fibrinogen |
| 1520.73 | GLIDEVNQDFTNR | Fibrinogen |
| 1501.74 | MELERPGGNEITR | Fibrinogen |
| 1441.79 | MKPVPDLVPGNFK | Fibrinogen |
| 1190.54 | QFTSSTSYNR | Fibrinogen |
| 1140.55 | GSESGIFTNTK | Fibrinogen |
| 1106.67 | VQHIQLLQK | Fibrinogen |
| 1062.51 | ALTDMPQMR | Fibrinogen |
| 1053.48 | MDGSLNFNR | Fibrinogen |
| 1028.50 | NSLFEYQK | Fibrinogen |
| 1010.51 | VTSGSTTTTR | Fibrinogen |
| 967.42 | GDFSSANNR | Fibrinogen |
| 944.53 | LEVDIDIK | Fibrinogen |
| 928.55 | QLEQVIAK | Fibrinogen |
| 925.39 | DYEDQQK | Fibrinogen |
| 923.49 | TVIGPDGHK | Fibrinogen |
| 870.38 | GDSTFESK | Fibrinogen |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 848.54 | QHLPLIK | Fibrinogen |
| 840.39 | TWQDYK | Fibrinogen |
| 826.51 | IRPLVTQ | Fibrinogen |
| 806.37 | EYHTEK | Fibrinogen |
| 804.43 | AQLVDMK | Fibrinogen |
| 782.34 | DNTYNR | Fibrinogen |
| 781.38 | GADYSLR | Fibrinogen |
| 755.41 | VPPEWK | Fibrinogen |
| 718.37 | VSEDLR | Fibrinogen |
| 700.40 | DLLPSR | Fibrinogen |
| 673.31 | HQSACK | Fibrinogen |
| 658.30 | SSSYSK | Fibrinogen |
| 3817.65 | YQEDTCYGDAGSAFAVHDLE EDTWYATGILSFDK | Haptoglobin |
| 3292.52 | VDSGNDVTDIADDGCPKPPE IAHGYVEHSVR | Haptoglobin |
| 2848.30 | LPECEADDGCPKPPEIAHGY VEHSVR | Haptoglobin |
| 2679.39 | MVSHHNLTTGATLINEQWLL TTAK | Haptoglobin |
| 2115.04 | SPVGVQPILNEHTFCAGMSK | Haptoglobin |
| 1795.01 | VVLHPNYSQVDIGLIK | Haptoglobin |
| 1650.80 | YVMLPVADQDQCIR | Haptoglobin |
| 1458.73 | NLFLNHSENATAK | Haptoglobin |
| 1439.66 | TEGDGVYTLNNEK | Haptoglobin |
| 1311.61 | TEGDGVYTLNDK | Haptoglobin |
| 1290.73 | DIAPTLTLYVGK | Haptoglobin |
| 1288.62 | SCAVAEYGVYVK | Haptoglobin |
| 1273.63 | LPECEAVCGKPK | Haptoglobin |
| 1203.64 | VISIQDWVQK | Haptoglobin |
| 1146.54 | HYEGSTVPEK | Haptoglobin |
| 987.54 | VMPICLPSK | Haptoglobin |
| 980.49 | VGYVSGWGR | Haptoglobin |
| 923.53 | ILGGHLDAK | Haptoglobin |
| 920.46 | GSFPWQAK | Haptoglobin |
| 895.47 | NPANPVQR | Haptoglobin |
| 858.49 | QLVEIEK | Haptoglobin |
| 809.38 | DYAEVGR | Haptoglobin |
| 760.40 | FTDHLK | Haptoglobin |
| 703.37 | VSVNER | Haptoglobin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 688.38 | QWINK | Haptoglobin |
| 688.38 | QWINK | Haptoglobin |
| 3954.02 | AIAANEADAVTLDAGLVYDA YLAPNNLKPWAEFYGSK | Transferrin |
| 2401.08 | QQQHLFGSNVTDCSGNFCLF R | Transferrin |
| 2159.01 | IMNGEADAMSLDGGFVYIAG K | Transferrin |
| 2114.07 | SAGWNIPIGLLYCDLPEPR | Transferrin |
| 2070.03 | EDLIWELLNQAQEHFGK | Transferrin |
| 2014.91 | SDNCEDTPEAGYFAVAVVK | Transferrin |
| 1703.76 | EGTCPEAPTDECKPVK | Transferrin |
| 1632.83 | DCHLAQVPSHTVVAR | Transferrin |
| 1629.82 | EDPQTFYYAVAVVK | Transferrin |
| 1611.72 | IECVSAETTEDCIAK | Transferrin |
| 1592.72 | LCMGSGLNLCEPNNK | Transferrin |
| 1577.81 | TAGWNIPMGLLYNK | Transferrin |
| 1529.75 | KPVEEYANCHLAR | Transferrin |
| 1520.64 | FDEFFSEGCAPGSK | Transferrin |
| 1482.69 | DQYELLCLDNTR | Transferrin |
| 1478.73 | MYLGYEYVTAIR | Transferrin |
| 1419.73 | CGLVPVLAENYNK | Transferrin |
| 1417.65 | CSTSSLLEACTFR | Transferrin |
| 1358.70 | SVIPSDGPSVACVK | Transferrin |
| 1297.61 | DYELLCLDGTR | Transferrin |
| 1283.57 | EGYYGYTGAFR | Transferrin |
| 1276.63 | EFQLFSSPHGK | Transferrin |
| 1273.65 | HSTIFENLANK | Transferrin |
| 1260.57 | WCAVSEHEATK | Transferrin |
| 1249.61 | SASDLTWDNLK | Transferrin |
| 1223.54 | CDEWSVNSVGK | Transferrin |
| 1195.55 | DSGFQMNQLR | Transferrin |
| 1166.59 | HQTVPQNTGGK | Transferrin |
| 1138.52 | WCALSHHER | Transferrin |
| 1000.50 | YLGEEYVK | Transferrin |
| 978.49 | DGAGDVAFVK | Transferrin |
| 964.53 | APNHAVVTR | Transferrin |
| 940.46 | ASYLDCIR | Transferrin |
| 878.46 | KPVDEYK | Transferrin |
| 874.44 | DSAHGFLK | Transferrin |

TABLE 3-continued

Potential target peptides expected from the mass spectral analysis (650-4000 Da) of tryptic digestion 11 of the highly abundant human serum proteins listed in table 5.

| Mass (Da) | Peptide Sequence (SEQ ID NOS 43-462 disclosed respectively in order of appearance) | Protein |
|---|---|---|
| 864.41 | DDTVCLAK | Transferrin |
| 830.39 | SCHTGLGR | Transferrin |
| 830.39 | SCHTAVGR | Transfenin |
| 827.40 | NPDPWAK | Transferrin |
| 735.40 | GDVAFVK | Transferrin |
| 686.33 | EACVHK | Transferrin |
| 663.38 | DLLFR | Transferrin |
| 654.31 | NTYEK | Transferrin |
| 652.30 | DSSLCK | Transferrin |
| 2455.15 | TSESGELHGLTTEEEFVEGI YK | Transthyretin |
| 2451.21 | ALGISPFHEHAEVVFTANDS GPR | Transthyretin |
| 2360.24 | YTIAALLSPYSYSTTAVVTN PK | Transthyretin |
| 1394.62 | AADDTWEPFASGK | Transthyretin |
| 1366.76 | GSPAINVAVHVFR | Transthyretin |
| 833.40 | GPTGTGESK | Transthyretin |
| 704.38 | VEIDTK | Transthyretin |
| 690.37 | CPLMVK | Transthyretin |
| 672.40 | VLDAVR | Transthyretin |

Other potentially contaminating peptides are the peptides listed in Table 4. These peptides, which can be attributed to various human keratins, were observed in the inventors' laboratory. The data were compiled from a total of 201 separate experiments using an ESI-LC-MS/MS system. Listed are the protein name, sequence, and number of experiments in which the peptide was observed, as well as how many total observations of the peptide were made. The number of observations listed is the sum of the number of times each peptide was observed at a charge state of +1H, +2H, and +3H combined for all experiments. In evaluating potential peptide targets, we take into account the number of times a peptide is observed within an experiment (which provides information about ionization efficiency and abundance) and how many times a peptide is observed among experiments (which indicates how a peptide is observed from experiment to experiment and reflects how enzyme cleavage is reproducible). The frequencies of observation in this table were used to generate the list of target peptides and subsequent antibodies used in Example I. From these results, we observed 118 total peptides. In the study shown in Example I, we've chosen a subset of these for the production of antibodies, starting with most observed peptides.

TABLE 4

All keratin peptides observed in 201 separate experiments in the inventor's laboratory using ESI-LC-MS/MS.

| Protein | Peptide Sequence (SEQ ID NOS 463-579 disclosed respectively in order of appearance) | Number of Experiments | Total Number of Observations |
|---|---|---|---|
| Keratin 2 | FLEQQNQVLQTK | 65 | 117 |
| Keratin 1 | QISNLQQSISDAEQR | 37 | 75 |
| Keratin 9 | DIENQYETQITQIEHEVSSSGQEVQSSAK | 29 | 67 |
| Keratin 1 | GSYGSGGSSYGSGGGSYGSGGGGGGHGSYGSGSSSGGYR | 29 | 57 |
| Keratin 9 | GGSGGSHGGGSGFGGESGGSYGGGEEASGSGGGYGGGSGK | 26 | 52 |

TABLE 4-continued

All keratin peptides observed in 201 separate experiments in the inventor's laboratory using ESI-LC-MS/MS.

| Protein | Peptide Sequence (SEQ ID NOS 463-579 disclosed respectively in order of appearance) | Number of Experiments | Total Number of Observations |
|---|---|---|---|
| Keratin 1 | WELLQQVDTSTR | 25 | 51 |
| Keratin 10 | ELTTEIDNNIEQISSYK | 23 | 66 |
| Keratin 1 | GGGGGGYGSGGSSYGSGGGSYGSGGGGGGGR | 23 | 40 |
| Keratin 9 | VQALEEANNDLENK | 22 | 34 |
| Keratin 9 | EIETYHNLLEGGQEDFESSGAGK | 21 | 43 |
| Keratin 1 | SLNNQFASFIDK | 21 | 36 |
| Keratin 10 | GSLGGGFSSGGFSGGSFSR | 21 | 35 |
| Keratin 10 | ALEESNYELEGK | 21 | 25 |
| Keratin 1 | LNDLEDALQQAK | 20 | 39 |
| Keratin 9 | HGVQELEIELQSQLSK | 20 | 28 |
| Keratin 2 | YEELQITAGR | 20 | 21 |
| Keratin 1 | SLDLDSIIAEVK | 19 | 25 |
| Keratin 2 | TSQNSELNNMQDLVEDYKK | 17 | 19 |
| Keratin 9 | GGGGSFGYSYGGGSGGGFSASSLGGGFGGGSR | 16 | 20 |
| Keratin 1 | SGGGFSSGSAGIINYQR | 16 | 19 |
| Keratin 9 | SDLEMQYETLQEELMALK | 14 | 60 |
| Keratin 10 | NQILNLTTDNANILLQIDNAR | 14 | 25 |
| Keratin 9 | TLNDMRQEYEQLIAK | 14 | 17 |
| Keratin 1 | THNLEPYFESFINNLR | 12 | 19 |
| Keratin 1 | TNAENEFVTIKK | 12 | 14 |
| Keratin 10 | NVSTGDVNVEMNAAPGVDLTQLLNNMR | 11 | 21 |
| Keratin 10 | QSVEADINGLRR | 10 | 18 |
| Keratin 1 | SLNNQFASFIDKVR | 10 | 12 |
| Keratin 10 | NVQALEIELQSQLALK | 9 | 13 |
| Keratin 10 | QSLEASLAETEGR | 9 | 12 |
| Keratin 9 | NYSPYYNTIDDLKDQIVDLTVGNNK | 9 | 11 |
| Keratin 1 | TNAENEFVTIK | 9 | 9 |
| Keratin 10 | IRLENEIQTYR | 8 | 10 |
| Keratin 10 | SKELTTEIDNNIEQISSYK | 8 | 10 |
| Keratin 10 | LKYENEVALR | 8 | 9 |
| Keratin 10 | ADLEMQIESLTEELAYLK | 7 | 17 |
| Keratin 2 | IEISELNR | 7 | 7 |
| Keratin 1 | SLVNLGGSKSISISVAR | 7 | 7 |
| Keratin 1 | MSGECAPNVSVSVSTSHTTISGGGSR | 6 | 9 |
| Keratin 1 | FSSSGGGGGSFGAGGGFGSR | 6 | 8 |
| Keratin 1 | LALDLEIATYR | 6 | 8 |

TABLE 4-continued

All keratin peptides observed in 201 separate experiments in the inventor's laboratory using ESI-LC-MS/MS.

| Protein | Peptide Sequence (SEQ ID NOS 463-579 disclosed respectively in order of appearance) | Number of Experiments | Total Number of Observations |
|---|---|---|---|
| Keratin 2 | VLYDAEISQIHQSVTDTNVILSMDNSR | 6 | 8 |
| Keratin 9 | LASYLDKVQALEEANNDLENK | 6 | 7 |
| Keratin 9 | QGVDADINGLR | 6 | 7 |
| Keratin 10 | TIDDLKNQILNLTTDNANILLQIDNAR | 6 | 7 |
| Keratin 10 | AETECQNTEYQQLLDIK | 6 | 6 |
| Keratin 9 | GGSGGSYGGGGSGGGYGGGSGSR | 6 | 6 |
| Keratin 2 | YLDGLTAER | 6 | 6 |
| Keratin 10 | DAEAWFNEK | 5 | 6 |
| Keratin 1 | NMQDMVEDYR | 5 | 6 |
| Keratin 2 | VDLLNQEIEFLK | 5 | 6 |
| Keratin 2 | GGGFGGGSSFGGGSGFSGGGFGGGGFGGGR | 5 | 5 |
| Keratin 10 | LENEIQTYR | 5 | 5 |
| Keratin 9 | QEYEQLIAK | 5 | 5 |
| Keratin 9 | TLLDIDNTR | 5 | 5 |
| Keratin 1 | NKLNDLEDALQQAK | 4 | 5 |
| Keratin 2 | NLDLDSIIAEVK | 4 | 5 |
| Keratin 2 | NVQDAIADAEQR | 4 | 5 |
| Keratin 9 | QVLDNLTMEK | 4 | 5 |
| Keratin 10 | QSVEADINGLR | 4 | 4 |
| Keratin 10 | SQYEQLAEQNR | 4 | 4 |
| Keratin 10 | LASYLDKVR | 3 | 4 |
| Keratin 1 | AEAESLYQSKYEELQITAGR | 3 | 3 |
| Keratin 1 | GSGGGSSGGSIGGR | 3 | 3 |
| Keratin 9 | SGGGGGGGLGSGGSIR | 3 | 3 |
| Keratin 2 | TAAENDFVTLKK | 3 | 3 |
| Keratin 1 | SKAEAESLYQSKYEELQITAGR | 3 | |
| Keratin 10 | ADLEMQIESLTEELAYLKK | 2 | 5 |
| Keratin 1 | LNDLEDALQQAKEDLAR | 2 | 4 |
| Keratin 2 | HGGGGGGFGGGGFGSR | 2 | 3 |
| Keratin 1 | AEAESLYQSK | 2 | 2 |
| Keratin 1 | DYQELMNTK | 2 | 2 |
| Keratin 2 | FASFIDKVR | 2 | 2 |
| Keratin 2 | GFSSGSAVVSGGSR | 2 | 2 |
| Keratin 1 | GGSGGGGGSSGGRGSGGGSSGGSIGGR | 2 | 2 |
| Keratin 10 | GSSGGGCFGGSSGGYGGLGGFGGGSFR | 2 | 2 |
| Keratin 9 | HGVQELEIELQSQLSKK | 2 | 2 |
| Keratin 10 | ISSSKGSLGGGFSSGGFSGGSFSR | 2 | 2 |

TABLE 4-continued

All keratin peptides observed in 201 separate experiments in the inventor's laboratory using ESI-LC-MS/MS.

| Protein | Peptide Sequence (SEQ ID NOS 463-579 disclosed respectively in order of appearance) | Number of Experiments | Total Number of Observations |
|---|---|---|---|
| Keratin 9 | MSCRQFSSSYLTSGGGGGGGLGSGGSIR | 2 | 2 |
| Keratin 2 | MSGDLSSNVTVSVTSSTISSNVASK | 2 | 2 |
| Keratin 9 | MTLDDFR | 2 | 2 |
| Keratin 2 | NKLNDLEEALQQAK | 2 | 2 |
| Keratin 2 | QSGSRGGSGGGGSISGGGYGSGGGSGGR | 2 | 2 |
| Keratin 10 | SGGGGGGGGCGGGGGVSSLR | 2 | 2 |
| Keratin 2 | SISISVAGGGGGFGAAGGFGGR | 2 | 2 |
| Keratin 1 | TLLEGEESR | 2 | 2 |
| Keratin 10 | VLDELTLTK | 2 | 2 |
| Keratin 9 | EEMSQLTGQNSGDVNVEINVAPGK | 1 | 2 |
| Keratin 2 | MSCVARSGGAGGGACGFR | 1 | 2 |
| Keratin 9 | NHKEEMSQLTGQNSGDVNVEINVAPGK | 1 | 2 |
| Keratin 1 | FSSCGGGGGSFGAGGGFGSRSLVNLGGSK | 1 | 1 |
| Keratin 9 | FSSSGGGGGGGRFSSSSGYGGGSSR | 1 | 1 |
| Keratin 1 | GGSGGGGGGSSGGR | 1 | 1 |
| Keratin 1 | GGSGGGYGSGCGGGGGSYGGSGRSGR | 1 | 1 |
| Keratin 2 | GGSISGGGYGSGGGK | 1 | 1 |
| Keratin 2 | GGSISGGGYGSGGGKHSSGGGSR | 1 | 1 |
| Keratin 1 | GSSSGGVKSSGGSSSVR | 1 | 1 |
| Keratin 10 | HYSSSR | 1 | 1 |
| Keratin 9 | IGLGGRGGSGGSYGRGSR | 1 | 1 |
| Keratin 1 | LDSELKNMODMVEDYR | 1 | 1 |
| Keratin 2 | LNDLEEALQQAK | 1 | 1 |
| Keratin 1 | LNVEVDAAPTVDLNR | 1 | 1 |
| Keratin 1 | LVVQIDNAK | 1 | 1 |
| Keratin 9 | NYSPYYNTIDDLK | 1 | 1 |
| Keratin 9 | QEIECQNQEYSLLLSIK | 1 | 1 |
| Keratin 9 | QFSSSYLSR | 1 | 1 |
| Keratin 2 | QLDSLLGERGNLEGELK | 1 | 1 |
| Keratin 1 | RSGGGGGRFSSCGGGGGSFGAGGGFGSR | 1 | 1 |
| Keratin 10 | RVLDELTLTK | 1 | 1 |
| Keratin 1 | SDLEAQVESLK | 1 | 1 |
| Keratin 10 | SEITELRR | 1 | 1 |
| Keratin 10 | SGGGGGGGGCGGGGGVSSLRISSSK | 1 | 1 |
| Keratin 1 | SMQDVVEDYK | 1 | 1 |
| Keratin 2 | STSSFSCLSR | 1 | 1 |

TABLE 4-continued

All keratin peptides observed in 201 separate experiments in the inventor's laboratory using ESI-LC-MS/MS.

| Protein | Peptide Sequence (SEQ ID NOS 463-579 disclosed respectively in order of appearance) | Number of Experiments | Total Number of Observations |
|---|---|---|---|
| Keratin 2 | TAAENDFVTLK | 1 | 1 |
| Keratin 1 | TGSENDFVVLKK | 1 | 1 |
| Keratin 10 | VTMQNLNDR | 1 | 1 |

In addition to the list of hypothetical tryptic peptides from abundant serum proteins that is shown in Table 5, the inventors have conducted experiments to identify peptides that are observed twice or more following actual tryptic digests of serum. Table 6 shows results from 29 separate experiments of tryptic digests of proteins from various sub-fractions of human serum run on ESI-LC-MS/MS.

TABLE 6

Commonly observed peptides from the most abundant serum proteins. Most common peptides observed among 29 separate experiments of tryptic digests of sub-fractions of human serum acquired by LC-MS/MS

| Protein name | Peptide sequence (SEQ ID NOS 580-677 disclosed respectively in order of appearance) | Number of Experiments | Number of Total Observations |
|---|---|---|---|
| Albumin | ALVLIAFAQYLQQCPFEDHVK | 3 | 3 |
| Albumin | AVMDDFAAFVEK | 14 | 17 |
| Albumin | DVFLGMFLYEYAR | 3 | 5 |
| Albumin | ETYGEMADCCAK | 2 | 2 |
| Albumin | FQNALLVR | 3 | 3 |
| Albumin | HPYFYAPELLFFAK | 2 | 3 |
| Albumin | KQTALVELVK | 2 | 2 |
| Albumin | KVPQVSTPTLVEVSR | 6 | 10 |
| Albumin | LDELRDEGK | 2 | 2 |
| Albumin | LVNEVTEFAK | 5 | 5 |
| Albumin | RHPDYSVVLLLR | 6 | 6 |
| Albumin | RHPYFYAPELLFFAK | 5 | 9 |
| Albumin | RPCFSALEVDETYVPK | 2 | 2 |
| Albumin | VFDEFKPLVEEPQNLIK | 4 | 15 |
| Albumin | VPQVSTPTLVEVSR | 3 | 4 |
| Albumin | YICENQDSISSK | 3 | 3 |
| Albumin | YLYEIAR | 5 | 5 |
| Alpha-1-antitrypsin | AVLDVFEEGTEASAATAVK | 1 | 2 |
| Alpha-1-antitrypsin | AVLTIDEKGTEAAGAMFLEAIPMSIPPEVK | 1 | 10 |
| Alpha-1-antitrypsin | DLDSQTMMVLVNYIFFK | 1 | 2 |
| Alpha-1-antitrypsin | DTEEEDFHVDQATTVK | 5 | 5 |
| Alpha-1-antitrypsin | DTEEEDFHVDQVTTVK | 7 | 160 |
| Alpha-1-antitrypsin | DYNLNDILLQLGIEEAFTSK | 1 | 2 |

TABLE 6-continued

Commonly observed peptides from the most abundant serum proteins. Most common peptides observed among 29 separate experiments of tryptic digests of sub-fractions of human serum acquired by LC-MS/MS

| Protein name | Peptide sequence (SEQ ID NOS 580-677 disclosed respectively in order of appearance) | Number of Experiments | Number of Total Observations |
|---|---|---|---|
| Alpha-1-antitrypsin | ELDRDTVFALVNYIFFK | 3 | 3 |
| Alpha-1-antitrypsin | FNKPFVFLMIEQNTK | 3 | 9 |
| Alpha-1-antitrypsin | FNKPFVFLMIEQNTKSPLFMGK | 1 | 3 |
| Alpha-1-antitrypsin | FNRPFLMIIVPTDTQNIFFMSK | 2 | 8 |
| Alpha-1-antitrypsin | GTEAAGAMFLEAIPMSIPPEVK | 9 | 108 |
| Alpha-1-antitrypsin | GTHVDLGLASANVDFAFSLYK | 3 | 4 |
| Alpha-1-antitrypsin | ITPNLAEFAFSLYR | 8 | 24 |
| Alpha-1-antitrypsin | LQHLENELTHDIITK | 6 | 22 |
| Alpha-1-antitrypsin | LQHLVNELTHDIITK | 2 | 2 |
| Alpha-1-antitrypsin | LSITGTYDLK | 7 | 18 |
| Alpha-1-antitrypsin | LSITGTYDLKSVLGQLGITK | 2 | 2 |
| Alpha-1-antitrypsin | LSSWVLLMK | 2 | 6 |
| Alpha-1-antitrypsin | LYGSEAFATDFQDSAAAK | 3 | 4 |
| Alpha-1-antitrypsin | LYHSEAFTVNFGDTEEAK | 4 | 16 |
| Alpha-1-antitrypsin | LYHSEAFTVNFGDTEEAKK | 5 | 13 |
| Alpha-1-antitrypsin | SASLHLPKLSITGTYDLKSVLGQLGITK | 3 | 3 |
| Alpha-1-antitrypsin | SPLFMGK | 2 | 8 |
| Alpha-1-antitrypsin | SVLGQLGITK | 7 | 22 |
| Alpha-1-antitrypsin | SVLGQLGITKVFSNGADLSGVTEEAPLK | 2 | 2 |
| Alpha-1-antitrypsin | SVLGQLGITKVFSNGADLSGVTEEAPLKLSK | 2 | 2 |
| Alpha-1-antitrypsin | TLNQPDSQLQLTTGNGLFLSEGLK | 10 | 72 |
| Alpha-1-antitrypsin | VFSNGADLSGVTEEAPLK | 15 | 123 |
| Alpha-1-antitrypsin | VFSNGADLSGVTEEAPLKLSK | 4 | 17 |
| Alpha-1-antitrypsin | WERPFEVK | 2 | 2 |
| Apolipoprotein Al | AELQEGAR | 2 | 3 |
| Apolipoprotein Al | AKPALEDLR | 2 | 2 |
| Apolipoprotein Al | DLATVYVDVLK | 5 | 5 |
| Apolipoprotein Al | DLATVYVDVLKDSGR | 2 | 2 |
| Apolipoprotein Al | DLATVYVDVLKDSGRDYVSQFEGSALGK | 5 | 7 |
| Apolipoprotein Al | DSGRDYVSQFEGSALGK | 9 | 29 |
| Apolipoprotein Al | DYVSQFEGSALGK | 16 | 73 |
| Apolipoprotein Al | EQLGPVTQEFWDNLEK | 16 | 168 |
| Apolipoprotein Al | EQLGPVTQEFWDNLEKETEGLR | 4 | 10 |
| Apolipoprotein Al | EQLGPVTQEFWDNLEKETEGLRQEMSK | 3 | 6 |
| Apolipoprotein Al | KWQEEMELYR | 1 | 4 |
| Apolipoprotein Al | LEALKENGGAR | 3 | 4 |

TABLE 6-continued

Commonly observed peptides from the most abundant serum proteins. Most common peptides observed among 29 separate experiments of tryptic digests of sub-fractions of human serum acquired by LC-MS/MS

| Protein name | Peptide sequence (SEQ ID NOS 580-677 disclosed respectively in order of appearance) | Number of Experiments | Number of Total Observations |
|---|---|---|---|
| Apolipoprotein Al | LHELQEK | 3 | 4 |
| Apolipoprotein Al | LLDNWDSVTSTFSK | 18 | 177 |
| Apolipoprotein Al | LREQLGPVTQEFWDNLEK | 7 | 20 |
| Apolipoprotein Al | LREQLGPVTQEFWDNLEKETEGLR | 5 | 17 |
| Apolipoprotein Al | LSPLGEEMR | 6 | 13 |
| Apolipoprotein Al | QGLLPVLESFK | 14 | 128 |
| Apolipoprotein Al | QLNLKLLDNWDSVTSTFSK | 2 | 2 |
| Apolipoprotein Al | THLAPYSDELR | 12 | 27 |
| Apolipoprotein Al | VEPLRAELQEGAR | 3 | 8 |
| Apolipoprotein Al | VKDLATVYVDVLK | 6 | 12 |
| Apolipoprotein Al | VKDLATVYVDVLKDSGR | 3 | 3 |
| Apolipoprotein Al | VKDLATVYVDVLKDSGRDYVSQFEGSALGK | 3 | 4 |
| Apolipoprotein Al | VQPYLDDFQK | 5 | 9 |
| Apolipoprotein Al | VQPYLDDFQKK | 2 | 4 |
| Apolipoprotein Al | VQPYLDDFQKKWQEEMELYR | 2 | 2 |
| Apolipoprotein Al | VSFLSALEEYTK | 15 | 169 |
| Apolipoprotein Al | VSFLSALEEYTKK | 4 | 7 |
| Apolipoprotein AI | WQEEMELYR | 12 | 29 |
| Apolipoprotein All | EPCVESLVSQYFQTVTDYGK | 1 | 2 |
| Apolipoprotein All | SKEQLTPLIK | 1 | 2 |
| Complement C3 | ILLQGTPVAQMTEDAVDAER | 1 | 3 |
| Haptoglobin | DIAPTLTLYVGK | 2 | 2 |
| Haptoglobin | GSFPWQAK | 3 | 3 |
| Haptoglobin | ILGGHLDAK | 1 | 3 |
| Haptoglobin | VGYVSGWGR | 3 | 4 |
| Haptoglobin | VTSIQDWVQK | 3 | 3 |
| Haptoglobin | VVLHPNYSQVDIGLIK | 3 | 4 |
| Transferrin | APNHAVVTR | 2 | 2 |
| Transferrin | CLKDGAGDVAFVK | 2 | 2 |
| Transferrin | EDPQTFYYAVAVVK | 3 | 3 |
| Transferrin | IMNGEADAMSLDGGFVYIAGK | 3 | 3 |
| Transferrin | SKEFQLFSSPHGK | 2 | 2 |
| Transferrin | SMGGKEDLIWELLNQAQEHFGK | 1 | 3 |
| Transferrin | TAGWNIPMGLLYNK | 2 | 2 |
| Transthyretin | ALGISPFHEHAEVVFTANDSGPR | 5 | 6 |
| Transthyretin | RYTIAALLSPYSYSTTAVVTNPKE | 3 | 3 |

TABLE 6-continued

Commonly observed peptides from the most abundant serum proteins. Most common peptides observed among 29 separate experiments of tryptic digests of sub-fractions of human serum acquired by LC-MS/MS

| Protein name | Peptide sequence (SEQ ID NOS 580-677 disclosed respectively in order of appearance) | Number of Experiments | Number of Total Observations |
|---|---|---|---|
| Transthyretin | TSESGELHGLTTEEEFVEGIYK | 4 | 5 |
| Transthyretin | TSESGELHGLTTEEEFVEGIYKVEIDTK | 5 | 5 |
| Transthyretin | YTIAALLSPYSYSTTAVVTNPKE | 3 | 4 |

Any highly abundant and/or highly ionizable peptide derived from any of the mentioned high abundant/contaminating proteins and/or highly abundant serum proteins, or others, can be removed by a method of the invention. Such peptides include any of the peptides discussed herein. In addition, a skilled worker will recognize that suitable fragments or variants of these peptides can also be used to generate antibodies for the removal of highly abundant and/or ionizing peptides from a preparation for MS analysis, provided that the fragments or variants retain the epitope(s) of the starting peptides. Suitable fragments may lack between about 1-5 amino acids from one or both ends of the peptide. Suitable variants include, e.g., peptides having small substitutions, additions, deletions, etc. Peptides that exhibit at least about 90% (e.g., at least about 95%, or at least about 98%) sequence identity to one of the peptides are also included. Methods for determining if a peptide exhibits a particular percent identity to another peptide are conventional.

In one embodiment of the invention, a single antibody is designed that can bind specifically to two highly abundant and/or ionizing peptides. For example, if two of the peptides identified by a method of the invention map to adjacent positions in a protein, one can design an antigen that encompasses portions of each sequence for the generation of antibodies. At least some of the resulting antibodies will thus bind specifically to each of the two peptides.

It should be noted that a variety of methods of mass spectral analysis can be performed, using different forms of ionization. These include, e.g., electron ionization, chemical ionization (CI), electrospray ionization (ESI), matrix-assisted laser desorption/ionization (MALDI), inductively coupled plasma (ICP), glow discharge, fast atom bombardment (FAB), thermospray, desorption/ionization on silicon (DIOS), direct analysis in real time (DART), atmospheric pressure chemical ionization (APCI), secondary ion mass spectrometry (SIMS), thermal ionization, nanospray, corona discharge, atmospheric pressure MALDI (AP-MALDI), desorption electrospray ionization (DESI), and chemical ionization (CI).

Different sources of ionization can give rise to analytes (e.g. peptides) having different charges. For example, in ESI, peptides often exhibit multiple charges (e.g. +2H, +3H); whereas in MALDI, peptides almost exclusively have only a single charge. The manner in which analytes (e.g. peptides) receive their charge has an effect on the peptides that are observed. Some peptides ionize better by one method than the other, and vice versa. There is not 100% overlap between what is observed in MALDI vs. what is observed in ESI. In some cases, a peptide identified as being highly ionizing by one of these methods may not be observed with the other method. Therefore, it may be necessary in some cases to use antibodies against different peptides for MALDI as for ESI applications. However, because there is some overlap between targets identified by the ESI and MALDI methods, it may in some cases be possible to use the same antibodies for both MALDI and ESI applications. A skilled worker can readily determine which peptides (and antibodies thereto) are suitable for use for which type of ionization procedure. A method of the invention can be used to identify highly abundant and/or highly ionizable peptides for a variety of types of ionization, and a variety of types of mass spectrometry.

Samples from any biological source can be used for preprocessing a sample destined for MS analysis or for concentrating a peptide of interest, including humans or other animals, plants, viruses, etc., as well as non-biological materials that can be recognized by antibodies. A variety of types of cells, tissues, organelles etc. can serve as sources for samples for a method of the invention. These include, e.g., serum/plasma, cerebral spinal fluid, urine, cardiac tissue, tears, saliva, biopsy tissues or the like.

A skilled worker will recognize suitable highly abundant proteins whose removal would be beneficial for MS analysis from a given type of sample. For example:

For cardiac tissue, it would be beneficial to remove the component proteins of myofibrils and mitochondria.

For brain, spleen, liver, pancreas, glands and kidney, it would be beneficial to remove tubulin and cytoskeleton proteins and nuclear proteins.

For lung, stomach, intestines, esophagus, trachea, arteries, veins and bladder, it would be beneficial to remove connective tissue proteins (elastins, cytokeratins, extracellular matrix proteins and fibrin) in addition to tubulin, cytoskeletal proteins and nuclear lamins.

A "highly abundant" peptide, as used herein, is a peptide that is present at more than about 10% of total peptides/proteins in a digested sample, or in the case of peptides, peptides that are detected above about 20% relative intensity to other peptides within the spectrum of the same purified protein. In some embodiments of the invention, it may be desirable to remove a peptide that is present in a lower amount, but which is highly ionizable.

By "highly ionizable" is meant that the species is observed in the mass spectrometer at greater than about 20% relative signal intensity than other peptides. In one embodiment of the invention, the peptide is a proteotypic peptide. "Proteotypic peptides," as used herein, refers to peptides in a protein sequence that are most likely to be confidently observed by current MS-based proteomics methods, and are considered to be indicative of the presence of a particular protein. The terms "highly ionizable," "highly ionized," "highly ionizing," "high ionization efficiency," well-ionizing," etc. are used interchangeably herein. It is important to note that it is the unique combination of enzyme accessibility, the ionization method, and the specific amino acid residues which determine what peptides (e.g. highly ionized or proteotypic peptides) are observed. This can be instrument specific.

In peptide mixtures, especially those that are complex, peptides compete for ionization. While there is no 'absolute' measure of the ionization efficiency of a peptide used in this invention, a measure of the 'relative' ionization efficiency of one peptide vs. another peptide within a sample can be determined. Thus, when evaluating whether a particular peptide is highly ionizable or has a high ionization efficiency, and thus, should be a target of depletion by the current invention, the relative intensity as well as total number of observations of a peptide compared to others in a sample is recorded. In this invention, a peptide with a greater than about 20% relative signal intensity over the other peptides in a sample can be used as a "rule of thumb" to indicate that the peptide is "highly ionizable" and thus is likely to be a "proteotypic peptide" or a peptide that is most likely to be observed when the protein is digested by a protease and analyzed by mass spectrometry. Relative abundance is a universal measure used in virtually all mass spectrometry methods.

Peptides that are to be removed from a sample, or concentrated, by a method of the invention, can be of any suitable size, depending on a variety of factors, which will be evident to a skilled worker. For example, peptides to be contacted with an antibody (either for immunodepletion or concentration) should be of a size that is amenable to antibody binding. Such peptides can be, e.g., at least about 5-8 amino acids in length, e.g. about 5-20, or more, amino acids, or about 8-15 amino acids. As used herein, the term "about" refers to plus or minus 10%. For example, "about 8 amino acids" is 7-9 amino acids. A "range" of values, as used herein, includes the end points of the range. Thus, 5-8 includes both 5 and 8.

Although much of the present discussion is directed to the removal of protein or peptide contaminants before the analysis of a protein/peptide sample by MS, other potential types of contaminants can also be removed from such samples, provided that specific antibodies can be generated against the potential contaminants. Examples of highly ionizable contaminants that can be removed from samples prior to analysis of the samples by MS include, e.g., various polymers (such as detergents or preparation contaminants), lipids (e.g., highly negatively charged lipids), glycoproteins, carbohydrates, small molecules, peptoids, or metabolites.

Any of a variety of proteases (proteolytic enzymes, peptidases) can be used to digest a protein-containing sample in preparation for mass spectral analysis and/or for identifying highly abundant, well-ionizing and/or proteotypic peptides whose removal from a sample preparation for mass spectral analysis would be desirable. Generally, the protease is a site-specific protease that results in peptide fragments in an observable mass range for tandem MS mass spectrometers (about 500-about 7000 DA). The proteases can be selected from, e.g., serine proteases, threonine proteases. cysteine proteases, aspartic acid proteases (e.g., plasmepsis), inetalloproteases, glutarnic acid proteases, or combinations thereof. Suitable proteases include, e.g., the proteases shown in Table 1.

TABLE 1

| |
|---|
| Achromopeptidase |
| Aminopeptidase |
| Ancrod |
| Angiotensin Converting Enzyme |
| Bromelain |
| Calpain |
| Calpain I |
| Calpain II |
| Carboxypeptidase A |
| Carboxypeptidase B |
| Carboxypeptidase G |
| Carboxypeptidase P |
| Carboxypeptidase W |
| Carboxypeptidase Y |
| Caspase |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 13 |
| Cathepsin B |
| Cathepsin C |
| Cathepsin D |
| Cathepsin G |
| Cathepsin H |
| Cathepsin L |
| Chymopapain |
| Chymase |
| Chymotrypsin, a- |
| Clostripain |
| Collagenase |
| Complement C1r |
| Complement C1s |
| Complement Factor D |
| Complement factor I |
| Cucumisin |
| Dipeptidyl Peptidase IV |
| Elastase, leukocyte |
| Elastase, pancreatic |
| Endoproteinase Arg-C |
| Endoproteinase Asp-N |
| Endoproteinase Glu-C |
| Endoproteinase Lys-C |
| Enterokinase |
| Factor Xa |
| Ficin |
| Furin |
| Granzyme A |
| Granzyme B |
| HIV Protease |
| IGase |
| Kallikrein tissue |
| Leucine Aminopeptidase (General) |
| Leucine aminopeptidase, cytosol |
| Leucine aminopeptidase, microsomal |
| Matrix metalloprotease |
| Methionine Aminopeptidase |
| Neutrase |
| Papain |
| Pepsin |
| Plasmin |
| Prolidase |
| Pronase E |
| Prostate Specific Antigen |
| Protease, Alkalophilic from *Streptomyces griseus* |
| Protease from *Aspergillus* |
| Protease from *Aspergillus saitoi* |
| Protease from *Aspergillus sojae* |
| Protease (*B. licheniformis*) (Alkaline) |
| Protease (*B. licheniformis*) (Alcalase) |
| Protease from *Bacillus polymyxa* |
| Protease from *Bacillus* sp |
| Protease from *Bacillus* sp (Esperase) |
| Protease from *Rhizopus* sp. |
| Protease S |
| Proteasomes |
| Proteinase from *Aspergillus oryzae* |
| Proteinase 3 |
| Proteinase A |

TABLE 1-continued

| |
|---|
| Proteinase K |
| Protein C |
| Pyroglutamate aminopeptidase |
| Renin |
| Rennin |
| Streptokinase |
| Subtilisin |
| Thermolysin |
| Thrombin |
| Tissue Plasminogen Activator |
| Trypsin |
| Tryptase |
| Urokinase |

Among the commonly used proteases are: Endoproteinase Asp-N from a *Pseudomonas fragi* mutant; Endoproteinase Glu-C from *Staphylococcus aureus* V8; Endoproteinase Glu-C from *Staphylococcus aureus* V8; Endoproteinase Lys-C from *Lysobacter enzymogenes*; Endoproteinase Pro-C from *E. coli* BioChemika; Endoproteinase Pro-Pro-Y-Pro; Papain; Pepsin; Proteinase A (e.g. from *S. cerevisiae*); Proteinase K; Proteinase from *Bacillus licheniformis* Type VIII; α-Chymotrypsin; and Trypsin. See, e.g., the Sigma-Aldrich catalogue.

In one embodiment, one or more (up to all) of the following proteases are used: trypsin, chymotrypsin, lys-C, or combinations thereof.

Antibodies specific for a peptide that is obtained by digesting a potentially contaminating protein by one method (e.g., trypsin digestion) may or may not recognize the same epitope(s) in peptides obtained by digesting the protein by another method (e.g., with a protease that recognizes a different cleavage site). Therefore, in one embodiment, in which highly abundant and/or ionizable and/or proteotypic peptides have been identified from a digest of a protein with an enzyme, that enzyme is also used to digest a sample for mass spectrometry (from which it is desirable to remove undesirable highly abundant and/or ionizable peptides).

In one embodiment, a protein target that has been selected for removal from a sample is cleaved to peptides by more than one method (e.g. digested, in separate reactions, with different proteases), and the presence of highly ionizable peptides is determined for peptides from each of the digests. Particularly desirable peptides may be obtained from one or more of the digests.

Chemical methods for cleaving proteins to peptides can also be used, and are well-known in the art. Suitable methods include, e.g., cleavage at aspartyl residues by formic acid; cyanogen bromide cleavage; 2-iodosobenzoic acid cleavage (IBA, e.g. using 2-Nitro-5-thiocyanatobenzoic acid powder), etc.

Once candidate peptides are identified (and verified) whose removal would be beneficial, these peptides can be physically removed from samples by any of a variety of conventional methods that involve agents (e.g. chemical agents) which are specific for the peptides. For example, peptoids, or small molecules with high affinities (e.g., clickity-click chemistries using highly functionalized peptoid oligomers, etc.) can be bound to agents that are specific for them and can thus be subsequently removed from the initial sample.

In one embodiment, the peptides are removed by immunodepletion, using antibodies that are specific for the peptides. For example, immunoprecipitation, or various forms of affinity products, including affinity chromatography, nanocolumns, spin columns, adsorption to antibody coated surfaces, such as pipette tips (e.g. disposable pipette tips), filters, membranes, etc. can be used.

An antibody that is "specific for" a peptide refers to an antibody that preferentially recognizes a defined sequence of amino acids, or epitope, that is present in the peptide, and not generally other peptides unintended for binding to the antibody. An antibody that "binds specifically" to ("is specific for"; binds "preferentially" to) a peptide of the invention interacts with the antibody, or forms or undergoes a physical association with it, in an amount and for a sufficient time to allow the peptide to be removed from the solution, or to be captured from the solution, by a method of the invention. By "specifically" or "preferentially" is meant that the antibody has a higher affinity, e.g. a higher degree of selectivity, for such a peptide than for other peptides in a sample. For example, the antibody can have an affinity for the peptide of at least about 5-fold higher than for other peptides in the sample. Typically this is application specific. For example, it does not matter if the antibody cross-reacts with peptides from proteins of different samples, if those peptides are not present in the sample of interest. The affinity or degree of specificity can be determined by a variety of routine procedures, including, e.g., competitive binding studies. A "cognate" peptide, as used herein, is a peptide for which an antibody is specific.

Methods for producing specific antibodies against a peptide of interest and for purifying the peptides are conventional. The peptides used for generation of the antibodies can be produced by a variety of methods, including isolating them from purified proteins that have been cleaved with a suitable enzymatic or chemical method. Alternatively, the peptides can be produced using conventional chemical synthesis techniques, such as those described, e.g., in G. Barony et al., The Peptides: Analysis, Synthesis & Biology, Academic Press, pp. 3-285 (1980). Some chemically synthesized peptides can be obtained from commercial suppliers. Alternatively, a peptide of the invention can be produced recombinantly following conventional genetic engineering techniques.

Generally, a peptide against which antibodies are to be produced is isolated or substantially purified before it is used to stimulate antibody formation. The term "substantially purified," as used herein refers to a molecule, such as a peptide, that is substantially free of other proteins, peptides, lipids, carbohydrates, nucleic acids and other biological materials with which it is naturally associated. For example, a substantially pure compound, such as a peptide, can be at least about 60%, by dry weight, preferably at least about 70%, 80%, 90%, 95%, or 99% the molecule of interest. Methods for isolating (purifying) proteins or peptides are conventional.

An "antibody," as used herein, can be, e.g., polyclonal, monoclonal (mAb), recombinant, humanized or partially humanized, chimeric, single chain, Fab, or fragments of such antibodies. Other specific binding partners, such as aptamers, can also be used. The antibody can be of any isotype, e.g., IgM, various IgG isotypes such as $IgG_1$. $IgG_{2a}$, etc., and it can be from any animal species that produces antibodies, including goat, rabbit, mouse, chicken or the like. A mixture of antibody types can be used. It is noted that antibodies raised against purified peptides, even polyclonal antibodies, will exhibit high degrees of specificity for a cognate peptide.

Antibodies can be prepared according to conventional methods, which are well known in the art. See, e.g. Green et al., Production of Polyclonal Antisera, in *Immunochemical Protocols* (Manson, ed.), (Humana Press 1992); Coligan et al., in *Current Protocols in Immunology*, Sec. 2.4.1 (1992); Kohler & Milstein (1975), *Nature* 256, 495; Coligan et al., sections 2.5.1-2.6.7; and Harlow et al., Antibodies: A Laboratory Manual, page 726 (Cold Spring Harbor Laboratory Pub. 1988). Methods of preparing humanized or partially humanized antibodies, antibody fragments, etc. and methods of purifying antibodies, are conventional.

In one embodiment, a mixture of antibodies is used which, in total, are specific for most, if not all, of the potentially contaminating peptides whose removal will bring about a significantly reduced amount of background. The number of proteins/peptides to be removed can be determined empirically, e.g. using methods as described herein. Generally, the removal of peptides from about 1-20 (e.g., about 8-12) proteins from a sample results in a significantly reduced amount of background. The removal of about 2-8 (e.g. about 3-5) peptides from each of the proteins is generally sufficient. In one embodiment, in a sample that contains keratin as a contaminant, the removal of about 2-6 keratin peptides (e.g., about 2-3 or about 4-6 such peptides) results in a significantly reduced amount of background. In another embodiment, in a sample from serum and/or plasma, the removal of peptides from about 2-14 highly abundant proteins (e.g., from about 10-14 such proteins, or about 2-7 such proteins, can result in a beneficial effect. In one embodiment, the removal of even one peptide from even one portion of the chromatograph can achieve a beneficial effect, allowing other species to be observed.

In general, immunodepletion of peptides according to the invention is carried out by contacting the peptides in a sample with specific antibodies under conditions that are effective for the antibodies to bind specifically to the peptides (to form specific antigen (peptide)-antibody complexes). "Effective conditions" vary according to a variety of factors, including the affinity of the antibodies for the peptides, components of the binding mixture, etc. Effective conditions can be optimized empirically, by conventional, routine procedures, as set forth, e.g., in Current Protocols in Immunology (Coligan et al., editors, John Wiley & Sons, Inc).

The antibodies may be free floating in the sample solution. After binding specifically to its cognate peptide, such an antibody can be separated from the sample solution by a variety of methods, which will be evident to a skilled worker. For example, the complexes may be allowed to bind to secondary antibodies which, in turn, are attached to a solid surface, to a magnetic bead, etc., so that the complex can be readily removed from the sample. Other separation techniques include, e.g., precipitation, centrifugation, filtration, chromatography, or the use of magnetism.

In another embodiment of the invention, an antibody that is specific for a peptide of interest is attached to (immobilized on) a surface; and the surface provides a mechanism by which peptides bound to antibodies thereon can be separated from the sample solution.

Any of a variety of suitable, compatible surfaces can be used in conjunction with this invention. The surface (usually a solid, preferably a suitable rigid or semi-rigid support) can be any of a variety of organic or inorganic materials or combinations thereof, including, merely by way of example, plastics such as polypropylene or polystyrene; ceramic; silicon; (fused) silica, quartz or glass, which can have the thickness of, for example, a glass microscope slide or a glass cover slip; paper, such as filter paper; diazotized cellulose; nitrocellulose filters; nylon membrane; or polyacrylamide gel pad. Suitable surfaces include membranes, filters, chips, slides, wafers, fibers, magnetic or nonmagnetic beads, gels, tubing, plates, polymers, microparticles, capillaries, or the like. The substrate can have a variety of surface forms, such as wells, trenches, pins, channels and pores, to which the nucleic acid probes are bound. The shape of the surface is not critical. It can, for example, be a flat surface such as a square, rectangle, or circle; a curved surface; or a three dimensional surface such as a bead, particle, strand, precipitate, tube, sphere, etc. Microfluidic devices are also encompassed by the invention.

In embodiments of the invention, the solid or semi-solid surface or carrier is the floor or wall in a microtiter well; a filter surface or membrane (e.g. a nitrocellulose membrane or a PVDF (polyvinylidene fluoride) membrane, such as an Immobilon membrane); a hollow fiber; a beaded chromatographic medium (e.g. an agarose or polyacrylamide gel); a magnetic bead; a fibrous cellulose matrix; an HPLC matrix; an FPLC matrix; a substance having molecules of such a size that the molecules with the antibody bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

Solid phase devices that can be used in conjunction with methods of the invention include a variety of affinity products, e.g., microtiter plates; flow-through assay devices; dipsticks; immunocapillary or immunochromatographic devices; disposable pipette tips for specific target(s), in either single or multiplex format; spin columns; filter plates or membranes; chromatography columns; affinity columns/plates; nanocolumns; online filters for online or offline chromatography; dedicated sample processing instrumentation; pre-columns for HPLC and nano-HPLC instrumentation that are coupled directly to mass spectrometers; etc.

In one embodiment, the antibodies are in the form of an array. The term "array" as used herein means an ordered arrangement of addressable, accessible, spatially discrete or identifiable, molecules (e.g., antibodies) disposed on a surface. Arrays can comprise any number of sites that comprise probes, from about 5 to, in the case of a microarray (sometimes referred to herein as a "chip"), tens to hundreds of thousands or more.

Immobilization of an antibody of the invention on a surface can be either covalent or non-covalent, and the non-covalent immobilization can be non-specific (e.g. non-specific binding to a polystyrene surface in e.g. a microtiter well). Specific or semi-specific binding to a solid or semi-solid carrier, support or surface, can be achieved by the antibody having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the antibody, such as 6-aminohexanoic acid, and the component is then avidin, streptavidin or an analogue thereof. An alternative is a situation in which the moiety has the amino acid sequence His-His-His-His-His-His (SEQ ID NO:703) and the carrier comprises a Nitrilotriacetic Acid derivative (NTA) charged with $Ni^{++}$ ions.

Procedures for separating peptides bound to antibodies on such surfaces from a sample will be evident to a skilled worker. For example, beads containing bound peptides can be spun out of a solution, or if they are magnetic, removed with a magnet. A sample can be placed on a chip and removed; and peptides bound to their cognate antibodies on the chip will remain behind. Samples can be passed through columns to which the antibodies are bound, spun through spin columns containing the antibodies, or passaged through pipette tips to which the antibodies are bound.

Antibodies of the invention can also be used with detectors if specific isoforms of proteins are desired to be observed.

As noted, another embodiment of the invention is a method to detect a protein of interest (e.g. a disease marker, a protein component of a pathogen, or a protein that is produced by a pathogen during infection or by the host in response to infection by the pathogen). In such a method, one or more highly ionizable peptides from the protein of interest are identified and purified, and antibodies specific for these peptides are generated, all as described elsewhere herein.

In one embodiment of the invention, the method comprises obtaining a sample (e.g. a bodily fluid or tissue suspected of containing a pathogen) from a subject; cleaving proteins in the sample to peptides; and contacting the resulting peptides with antibodies of the invention, under conditions effective for the formation of a specific antigen (peptide)-antibody reactions. Following the binding of the antibodies to the peptides (thereby isolating, concentrating, enriching, capturing the peptides), excess components of the sample are optionally removed (washed off); the bound peptides are eluted, using conventional procedures; and the eluted peptides are analyzed by mass spectrometry. The detection of peptides from organisms of interest can be used for medical diagnosis, monitoring the environment, analysis of samples suspected of being involved in bioterrorism, or a variety of other uses that will be evident to a skilled worker.

Another embodiment of the invention involves the detection of disease markers (proteins) that are present in low levels in a sample. Highly ionizable peptides from such markers are captured and eluted as described above for pathogen-specific peptides. By identifying highly ionizable peptides from these markers and capturing them with an antibody specific for the peptides, one can significantly increase the sensitivity of detection of the markers in an MS assay. It is thus possible to diagnose a disease (to detect the presence of such disease markers in a sample from a subject), in spite of low levels of the markers of the disease.

Another aspect of the invention is a composition comprising highly abundant and/or ionizable and/or proteotypic peptides of the invention. Such a composition can be used to generate antibodies that are specific for the peptides. Another aspect of the invention is a composition comprising antibodies that are specific for the highly abundant and/or ionizable and/or proteotypic peptides of the invention. The antibodies may be of any of the types discussed herein, or combinations thereof.

Another aspect of the invention is a kit for carrying out any of the methods of the invention. For example, one embodiment is a kit for immunodepleting undesired peptides from a sample destined to be subjected to MS analysis. Another embodiment is a kit for detecting (diagnosing) the presence of peptides of interest (e.g., highly ionizing peptides from proteins from one or more pathogens, or from a disease marker) in a sample. A kit of the invention may, for example, comprise one or more antibodies that are specific for such and, optionally, means for storing or packaging the antibodies. The antibodies may be in a lyophilized form or in liquid form; they may be stabilized.

The components of the kit will vary according to which method is being performed. Optionally, the kits comprise instructions (e.g., written instructions) for performing the method. Other optional elements of a kit of the invention include suitable buffers, media components, or the like; containers; or packaging materials. The reagents of the kit may be in containers in which the reagents are stable, e.g., in lyophilized form or stabilized liquids. The reagents may also be in single use form, e.g., in amounts for depleting peptides from a single sample, or for carrying out a single diagnostic test. Other components of a kit can easily be determined by one of skill in the art. Such components may include suitable controls or standards, buffers or other reagents appropriate for constituting a reaction medium allowing the formation of a peptide-antibody omplex, etc.

Another aspect of the invention is a device to which one or more antibodies of the invention are attached. Such a device can be used to immunodeplete one or more (e.g. about 5 or more) peptides from a sample, or to isolate/concentrate one or more (e.g. about 5 or more) peptides of interest. Any of the types of devices discussed herein are included.

A skilled worker will recognize that the methods, compositions and devices of the invention can be applied to a wide range of uses, including, e.g., diagnostics, clinical assays, toxicology, glycomics, lipidomics, etc.

In the foregoing and in the following examples, all temperatures are set forth in uncorrected degrees Celsius; and, unless otherwise indicated, all parts and percentages are by weight.

EXAMPLES

Example I

Immunodepletion of Keratin Peptides from a Sample

Antibodies against two keratin-specific peptides were used to immunodeplete a sample containing a mixture of purified peptides. The purified peptides used in the experiment were the same as the antigens used for antibody production and were designed to be representative of two distinct regions in the sequence of Keratin 1 and Keratin 2. The peptide named Keratin Peptide 1 (KP1), (CSISDAEQRGENALK, MW=1621 Da) (SEQ ID NO:704), was designed to represent amino acids 424-437 of Keratin 1 a nd 430-436 of Keratin 2. The peptide named Keratin Peptide 2 (KP2), (ELLQQVDTSTR, MW=1290 Da) (SEQ ID NO:705) was designed to represent amino acids 212-222 of Keratin 1 and 217-227 of Keratin 2.

The peptides were synthesized chemically and polyclonal antibodies were raised against each peptide, using conventional procedures. We conducted ELISA assays, using conventional procedures, which confirmed that the antisera raised against each of these peptides do, in fact, bind to their cognate peptides specifically. The disposable pipette tips used for this experiment were loaded with cellulose that was pretreated with potassium iodate (KIO3). The tips were washed with ammonium bicarbonate, 20 mM, pH 7.4, 20 mM Octyl-B-D-Glycopyranoside once. The antibody was chemically bound to the column in the same buffer, blocked with a protein-free blocker, then washed three times with the buffer. The peptide mixtures were prepared in the same buffer and then loaded onto the antibody-bound pipette tips. Samples were aspirated five times to bind the peptides. The unbound sample was then analyzed by MALDI-TOF MS, using conventional procedures.

Figure 3:
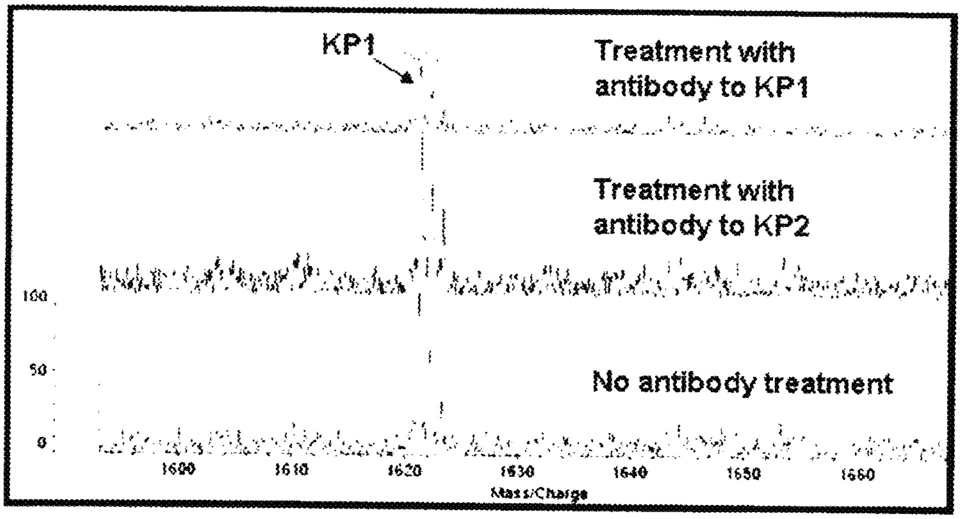
FIG. 3 shows MALDI spectra showing the specificity of antibodies against two peptides from keratin.

To demonstrate the specificity of the two antibodies for their cognate peptides, samples containing just KP1 were subjected to treatment with pipette tips loaded with antibodies against KP1 or KP2 and the unbound fraction was analyzed by MALDI-TOF MS. As shown in FIG. 3, each antibody exhibited the desired specificity. The bottom spectrum of the figure is a control showing 2 ng of KP1 loaded onto the sample plate. The middle spectrum shows the sample after treatment with an antibody tip to KP2. Note no loss in signal intensity of the KP1 peak, as the KP2 antibody does not bind to KP 1. The top spectrum shows the sample after treatment with the antibody to KP1. Note the loss in signal intensity of the KP1 peak due to the removal of KP1 from the sample by the antibody tip to KP1.

Figure 4:
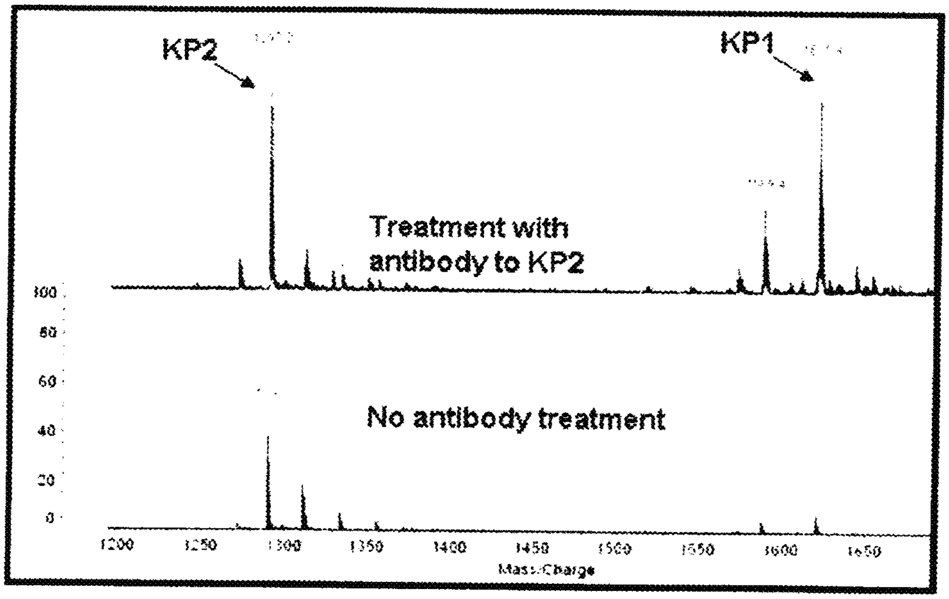
FIG. 4 shows MALDI spectra showing the benefits of immunodepletion of keratin peptides from a sample.

To demonstrate the beneficial effect of treating a sample with antibodies against keratin-specific peptides, samples containing both purified KP1 and KP2 were treated by a method of the invention, as above. FIG. 4 shows the beneficial effects of the method. The bottom spectrum shows a mixture of equal amounts (200 ng each) of the two keratin peptides (KP1 and KP2) without having been treated with the tips bound with antibodies. Note that when equal amounts of KP1 and KP2 are analyzed (bottom spectrum), KP2 is detected at a higher relative intensity. This is due to the fact that KP2 has a higher ionization efficiency than KP1. The top spectrum shows the result after treatment of the sample with an antibody tip against KP2. After treatment, as shown in the top spectrum, the relative intensity of KP1 is much higher than before treatment. This is attributed to the fact that there is less KP2 in the sample, thus allowing better detection of KP1.

Example II

Immunodepletion of Highly Abundant Peptides from a Serum Sample

To select suitable peptides for immunodepletion, we first identified the most highly abundant proteins in serum, as shown in Table 5. We then performed an "in silico" digest of these serum proteins, using cleavage specific sites for trypsin. This provided a total of all of the possible peptides from a tryptic digest. We then looked for these peptides using ESI—liquid chromatography mass spectrometry in samples derived from the tryptic digestion of sub-fractions of human serum. We determined how many times each peptide was observed experimentally, determined their ionizing efficiencies, and determined which peptides were proteotypic under these conditions. On the basis of these analyses, we selected the top 2-4 peptide sequences corresponding to the highest number of observations (Table 7). We will generate antibodies against these 24 peptides, combine the antibodies in a depletion column (an affinity column, using cellulose as the matrix material), pass tryptic digests of serum samples over the column, and collect the eluate (which will have been immunodepleted for the 24 peptides). All of these procedures will be carried out with conventional procedures. Following depletion of high-abundance peptides, we expect that novel peptides will be observed during MS as compared to undepleted control samples. Furthermore, peptides corresponding to proteins that are non-specifically depleted by whole-protein affinity column approaches (e.g. MARS, IgY12) will be observed by this peptide-based depletion method. Consequently, this method will eliminate the loss of peptides which are removed by the whole-protein removal approaches, either because they bind to the proteins that are targeted for removal or because they bind non-specifically to the affinity columns.

TABLE 7

| Protein name | Peptide sequence (SEQ ID NOS 678-702 disclosed respectively in order of appearance) | Number of Experiments | Number of Total Observations |
| --- | --- | --- | --- |
| Albumin | VFDEFKPLVEEPQNLIK | 4 | 15 |
| Albumin | RHPYFYAPELLFFAK | 5 | 9 |
| Albumin | KVPQVSTPTLVEVSR | 6 | 10 |
| Albumin | AVMDDFAAFVEK | 14 | 17 |
| Alpha-1-antitrypsin | DTEEEDFHVDQVTTVK | 7 | 160 |
| Alpha-1-antitrypsin | ITPNLAEFAFSLYR | 8 | 24 |
| Alpha-1-antitrypsin | GTEAAGAMFLEAIPMSIPPEVK | 9 | 108 |
| Alpha-1-antitrypsin | TLNQPDSQLQLTTGNGLFLSEGLK | 10 | 72 |
| Alpha-1-antitrypsin | VFSNGADLSGVTEEAPLK | 15 | 123 |
| Apolipoprotein Al | QGLLPVLESFK | 14 | 128 |
| Apolipoprotein Al | VSFLSALEEYTK | 15 | 169 |
| Apolipoprotein Al | DYVSQFEGSALGK | 16 | 73 |
| Apolipoprotein Al | EQLGPVTQEFWDNLEK | 16 | 168 |
| Apolipoprotein Al | LLDNWDSVTSTFSK | 18 | 177 |
| Apolipoprotein All | EPCVESLVSQYFQTVTDYGK | 1 | 2 |
| Apolipoprotein All | SKEQLTPLIK | 1 | 2 |
| Complement C3 | ILLQGTPVAQMTEDAVDAER | 1 | 3 |

TABLE 7-continued

| Protein name | Peptide sequence (SEQ ID NOS 678-702 disclosed respectively in order of appearance) | Number of Experiments | Number of Total Observations |
|---|---|---|---|
| Haptoglobin | VGYVSGWGR | 3 | 4 |
| Haptoglobin | VVLHPNYSQVDIGLIK | 3 | 4 |
| Transferrin | SMGGKEDLIWELLNQAQEHFGK | 1 | 3 |
| Transferrin | EDPQTFYYAVAVVK | 3 | 3 |
| Transferrin | IMNGEADAMSLDGGFVYIAGK | 3 | 3 |
| Transthyretin | TSESGELHGLTTEEEFVEGIYK | 4 | 5 |
| Transthyretin | ALGISPFHEHAEVVFTANDSGPR | 5 | 6 |
| Transthyretin | TSESGELHGLTTEEEFVEGIYKVEIDTK | 5 | 5 |

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above (including U.S. provisional application 60/818,363, filed Jul. 3, 20066) and in the figures, are hereby incorporated in their entirety by reference.

We claim:

1. A method for pre-processing a sample for electrospray ionization mass spectroscopy (ESI) analysis, comprising cleaving proteins in the sample to peptides and immunodepleting highly abundant and/or well-ionizing and/or proteotypic peptides from the sample.

2. The method of claim 1, wherein the cleaving comprises digesting the proteins with a protease.

3. The method of claim 2, wherein the protease is trypsin, chymotrypsin, and/or Lys-C.

4. The method of claim 1, wherein peptides from between about 1-20 proteins are removed from the sample.

5. The method of claim 1, wherein peptides from between about 8-12 proteins are removed from the sample.

6. The method of claim 1, wherein the sample is from plasma/serum, and the high abundant and/or well-ionizing and/or proteotypic peptides are from one or more of the proteins listed in Table 5.

7. The method of claim 1, wherein the highly abundant and/or well-ionizing and/or proteotypic peptides comprise one or more of the peptides listed in Table 3 and/or Table 6 and/or Table 7.

8. The method of claim 1, wherein the sample contains keratins and/or trypsin, and the high abundant and/or well-ionizing and/or proteotypic peptides are selected from one or more of the peptides listed in Table 2 and/or Table 4.

9. The method of claim 4, wherein about 3-5 peptides from each of the proteins are removed.

10. The method of claim 1, wherein the immunodepletion is carried out by contacting the sample comprising cleaved proteins with one or more antibodies that are specific for highly abundant and/or well-ionizing and/or proteotypic peptides in the sample, under conditions that are effective for the antibodies to bind specifically to their cognate peptides, and separating the resulting antibody/peptide complexes from the sample.

11. The method of claim 10, further wherein the well-ionizing peptides are identified by a) cleaving a protein known or suspected to be a contaminant with a protease;

b) subjecting the resulting peptides to mass spectrometry; and c) ranking the peptides in order of degree of ionization.

12. The method of claim 10, wherein one or more of the antibodies are monoclonal antibodies.

13. The method of claim 10, wherein all of the antibodies are monoclonal antibodies.

14. The method of claim 10, wherein one or more of the antibodies are polyclonal antibodies.

15. The method of claim 10, wherein all of the antibodies are polyclonal antibodies.

* * * * *